(12) United States Patent
Ervin et al.

(10) Patent No.: US 10,338,070 B2
(45) Date of Patent: Jul. 2, 2019

(54) CELL-FREE ASSAY DEVICE AND METHODS OF USE

(71) Applicant: ELECTRONIC BIO SCIENCES, INC., San Diego, CA (US)

(72) Inventors: Eric Ervin, Salt Lake City, UT (US); Anna E. P. Schibel, Snoqualmie, WA (US)

(73) Assignee: Electronic BioSciences, Inc., San Diego, CA (US)

(*) Notice: Subject to any disclaimer, the term of this patent is extended or adjusted under 35 U.S.C. 154(b) by 0 days.

(21) Appl. No.: 15/498,864

(22) Filed: Apr. 27, 2017

(65) Prior Publication Data

US 2017/0276678 A1   Sep. 28, 2017

Related U.S. Application Data

(63) Continuation of application No. 14/408,936, filed as application No. PCT/US2013/046318 on Jun. 18, 2013, now abandoned.

(60) Provisional application No. 61/661,318, filed on Jun. 18, 2012, provisional application No. 61/775,163, filed on Mar. 8, 2013.

(51) Int. Cl.
| | |
|---|---|
| *G01N 33/573* | (2006.01) |
| *G01N 33/487* | (2006.01) |
| *G01N 33/92* | (2006.01) |
| *G01N 33/68* | (2006.01) |

(52) U.S. Cl.
CPC ..... *G01N 33/573* (2013.01); *G01N 33/48721* (2013.01); *G01N 33/6872* (2013.01); *G01N 33/92* (2013.01); *G01N 2333/952* (2013.01); *G01N 2500/20* (2013.01); *G01N 2800/709* (2013.01)

(58) Field of Classification Search
CPC .......... G01N 33/573; G01N 33/48721; G01N 33/6872; G01N 33/92
See application file for complete search history.

(56) References Cited

U.S. PATENT DOCUMENTS

| | | | |
|---|---|---|---|
| 5,530,101 | A | 6/1996 | Queen et al. |
| 5,707,622 | A | 1/1998 | Fong et al. |
| 5,990,296 | A | 11/1999 | Pastan et al. |

(Continued)

FOREIGN PATENT DOCUMENTS

| | | |
|---|---|---|
| WO | WO 2006/130299 | 12/2006 |
| WO | WO 2008/060324 | 5/2008 |
| WO | WO 2012/142174 | 10/2012 |

OTHER PUBLICATIONS

Office Action dated Aug. 24, 2017 in U.S. Appl. No. 14/110,089, filed Dec. 30, 2013 and published as US 2014-0106472 on Apr. 17, 2014.

(Continued)

*Primary Examiner* — Melanie Brown
(74) *Attorney, Agent, or Firm* — Grant IP, Inc.

(57) ABSTRACT

Provided herein is a cell-free assay device, sometimes comprising a lipid bilayer and an endopeptidase assay component, for characterizing a pore forming protein. In some embodiments provided herein is an apparatus comprising a pressure system for characterizing an interaction. Also, provided herein are methods for using a cell-free assay device to characterize a pore forming protein and/or a test substance.

25 Claims, 11 Drawing Sheets

(56) References Cited

U.S. PATENT DOCUMENTS

| | | | |
|---|---|---|---|
| 5,994,524 | A | 11/1999 | Matsushima et al. |
| 6,099,842 | A | 8/2000 | Pastan et al. |
| 6,245,894 | B1 | 6/2001 | Matsushima et al. |
| 6,342,221 | B1 | 1/2002 | Thorpe et al. |
| 6,395,557 | B1 | 5/2002 | Fouillet et al. |
| 7,777,505 | B2 | 8/2010 | White et al. |
| 2002/0012843 | A1 | 1/2002 | Fowlkes et al. |
| 2002/0182627 | A1 | 12/2002 | Wang et al. |
| 2003/0146091 | A1 | 8/2003 | Vogel et al. |
| 2004/0120861 | A1 | 6/2004 | Petroff |
| 2005/0074778 | A1 | 4/2005 | Letant et al. |
| 2007/0116610 | A1 | 5/2007 | Cuppoletti |
| 2008/0025875 | A1* | 1/2008 | Martin ............... B01D 67/0032 422/82.01 |
| 2008/0121534 | A1 | 5/2008 | White |
| 2009/0205960 | A1* | 8/2009 | Schaffer ........... G01N 33/48721 204/452 |
| 2009/0258372 | A1 | 10/2009 | Lopez et al. |
| 2011/0036719 | A1* | 2/2011 | Neyts ................ G01N 15/1031 204/549 |
| 2011/0041978 | A1 | 2/2011 | Wallace |
| 2011/0121840 | A1 | 5/2011 | Sanghera et al. |
| 2011/0130312 | A1 | 6/2011 | Notte et al. |
| 2012/0190040 | A1 | 7/2012 | Talebpour |
| 2012/0193236 | A1* | 8/2012 | Peng ................ G01N 33/48721 204/603 |
| 2012/0222958 | A1 | 9/2012 | Pourmand |
| 2012/0255862 | A1 | 10/2012 | Dunnam et al. |
| 2014/0106472 | A1 | 4/2014 | Ervin et al. |
| 2014/0174927 | A1 | 6/2014 | Bashir |
| 2018/0321180 | A1 | 11/2018 | Ervin et al. |

OTHER PUBLICATIONS

Office Action dated Feb. 23, 2018 in U.S. Appl. No. 14/110,089, filed Dec. 30, 2013 and published as US 2014-0106472 on Apr. 17, 2014.

Ali et al., "Biosensing and supramolecular bioconjugation in single conical polymer nanochannels. Facile incorporation of biorecognition elements into nanoconfined geometries" Journal of the American Chemical Society (2008) 130(48):16351-16357.

Ali et al., "Metal ion affinity-based biomolecular recognition and conjugation inside synthetic polymer nanopores modified with iron-terpyridine complexes" Journal of the American Chemical Society (2011) 133(43):17307-17314.

Kohler and Milstein, "Continuous cultures of fused cells secreting antibody of predefined specificity" Nature (1975) 256:495-497.

Movileanu et al., "Detecting protein analytes that modulate transmembrane movement of a polymer chain within a single protein pore" Nature Biotechnology (2000) 18:1091-1095.

Sexton et al., "Developing synthetic conical nanopores for biosensing applications" Molecular Biosystems (2007) 3(10):667-685.

Siwy et al., "Protein biosensors based on biofunctionalized conical gold nanotubes" Journal of the American Chemical Society (2005) 127(14):5000-5001.

St Groth and Scheidegger, "Production of monoclonal antibodies: strategy and tactics" J. Immunol. Methods (1980) 5:1-21.

Sun and Mirkin, "Scanning Electrochemical Microscopy with Slightly Recessed Nanotips" Anal. Chem. (2007) 79(15):5809-5816.

Vlassiouk et al., Journal of the American Chemical Society (2009) 131(23):8211-8220.

International Search Report and Written Opinion dated Nov. 1, 2013 in International Application No. PCT/US2013/046318, filed on Jun. 18, 2013 and published as WO 2013/192178 on Dec. 27, 2013.

International Preliminary Report on Patentability dated Dec. 23, 2014 in International Application No. PCT/US2013/046318, filed on Jun. 18, 2013 and published as WO 2013/192178 on Dec. 27, 2013.

Supplementary European Search Report dated Jan. 13, 2016 in European Patent Application No. EP 13807736.7, filed on Jun. 18, 2013 and published as EP 2 861 998 on Apr. 22, 2015.

International Search Report and Written Opinion dated Jul. 2, 2012 in International Application No. PCT/US2012/33142, filed on Apr. 11, 2012 and published as WO 2012/142174 on Oct. 18, 2012.

International Preliminary Report on Patentability dated Oct. 24, 2013 in International Application No. PCT/US2012/33142, filed on Apr. 11, 2012 and published as WO 2012/142174 on Oct. 18, 2012.

Extended European Search Report dated Dec. 12, 2014 in EP Application No. 12770608.3, filed on Apr. 11, 2012 and published as EP 2 697 394 on Feb. 19, 2014.

Office Action dated Aug. 23, 2016 in U.S. Appl. No. 14/408,936, filed Dec. 17, 2014 and published as U.S. 2015-0204873 on Jul. 23, 2015.

Office Action dated Jan. 30, 2017 in U.S. Appl. No. 14/408,936, filed Dec. 17, 2014 and published as U.S. 2015-0204873 on Jul. 23, 2015.

Office Action dated Feb. 23, 2017 in U.S. Appl. No. 14/110,089, filed Dec. 30, 2013 and published as US 2014-0106472 on Apr. 17, 2014.

Office Action dated Nov. 2, 2018 in U.S. Appl. No. 15/984,158, filed May 18, 2018 and published as US 2018-0321180 on Nov. 8, 2018.

* cited by examiner

CELL-FREE ASSAY DEVICE AND METHODS OF USE

RELATED PATENT APPLICATIONS

This patent application is a continuation of U.S. patent application Ser. No. 14/408,936, filed Dec. 17, 2014, entitled CELL-FREE ASSAY DEVICE AND METHODS OF USE, naming Eric N. ERVIN and Anna E. P. SCHIBEL as inventors, which is a 35 U.S.C. 371 national phase patent application of PCT/US2013/046318, filed on Jun. 18, 2013, entitled CELL-FREE ASSAY DEVICE AND METHODS OF USE, naming Eric N. ERVIN and Anna E. P. SCHIBEL as inventors, which claims the benefit of U.S. Provisional Patent Application No. 61/661,318 filed on Jun. 18, 2012, entitled LIPID BILAYER BASED ASSAY FOR TOXIN CHARACTERIZATION, naming Eric N. Ervin and Anna E. P. Schibel as inventors, and claims the benefit of U.S. Provisional Patent Application No. 61/775,163 filed on Mar. 8, 2013, entitled ALTERING ANALYTE BINDING THROUGH THE USE OF PRESSURE, naming Eric N. Ervin and Anna E. P. Schibel as inventors. The entire content of each of the foregoing provisional applications is incorporated herein by reference, including all text, tables and drawings.

STATEMENT OF GOVERNMENT SUPPORT

This invention was made with government support under Contract No. W81XWH-11-C-0085 awarded by U.S. Army Medical Research Acquisition Activity and Grant No. 1R43NS074610 awarded by the National Institutes of Health. The government has certain rights in the invention.

FIELD

Provided here is a cell-free assay device and methods for characterizing a protein or toxin.

BACKGROUND

Toxins are potent molecules used by bacteria, that can act locally or at a distance from the infection site in a host organism. While some toxins, cause disruption of all cell types (e.g. cytotoxins), other toxins are only active on specific cells such as enterotoxins active on epithelial intestinal cells and neurotoxins targeting neuronal cells. This specificity is achieved by the recognition of specific cell surface receptor(s) and/or specific intracellular target(s). The nervous system is one of the main targets of bacterial toxins. One of the most common bacterial neurotoxin is the botulinum neurotoxin (BoNT).

Botulinum neurotoxin (BoNT) is secreted by the bacterium *Clostridium botulinum*, and is one of the most toxic compounds known to man. The lethal dose for humans has been estimated to be as little as 1 nanogram per kilogram of body weight. Exposure to the toxin causes flaccid paralysis of cells resulting in muscle weakness, impaired respiratory function, malfunction of the nervous system and ultimately death by respiratory failure. The extreme potency of the neurotoxin presents a potential threat for use in bio-warfare; however, in small doses, BoNT has many medicinal and cosmetic benefits such as the treatment of neuromuscular disorders and prevention of wrinkles (e.g. Botox).

There are seven distinct isoforms of the toxin, designated as BoNT type-A (BoNT/A) through BoNT type-G (BoNT/G) that are produced by different strains of the botulinum bacterium, also designated types A-G, respectively. Each isoform has a similar function within cells, ultimately inhibiting neurotransmission through cleavage of one of the three SNARE proteins. BoNT/A, is the serotype most commonly used for therapeutic purposes. BoNT is secreted as a 150 kDa single polypeptide chain consisting of two units connected via a disulfide bond, designated the heavy chain (HC), which is about 100 kDa, and a light chain (LC), which is about 50 kDa. The mechanism of BoNT is highly complex and has been characterized. Upon entering the body, the toxin attacks nerve cells through a three step process. First, the HC binds to the bilayer membrane of a neuron forming a transmembrane protein pore. Second, the LC translocates the formed pore and is released into the cytosol. Third, the LC cleaves one of three SNARE proteins (SNAP-25, synaptobrevin, or syntaxin) prohibiting SNARE complex formation and subsequent acetylcholine release/neurotransmission, and thus muscular contraction.

Despite its extreme toxicity, BoNT/A has many therapeutic uses. Starting in 1980, BoNT/A was used to treat strabismus ("crossed eyes") and blepharospasm ("uncontrollable blinking"). By 1989, the FDA had also approved the use of BoNT/A to treat hemifacial spasms ("uncontrollable spasms of facial muscles"). It was at this time that various studies of BoNT/A for treating facial wrinkles began. By 2002, the FDA had approved the use of BoNT/A for treating wrinkles around the eyes and mouth. In addition to these current uses, BoNT/A is currently approved for Upper Motor Neuron Diseases (e.g., amyotrophiclateral sclerosis, Lou Gehrig's disease and pseudobular palsy) and spasticity. Studies for treating hyperhidrosis (excessive sweating), migraines, asthma, and prostatic symptoms (i.e., abnormal prostate symptoms) using BoNT/A are currently underway.

SUMMARY

Provided herein, in certain aspects, is a cell-free assay device, comprising a lipid bilayer configured to separate a first electrolyte volume and a second electrolyte volume, a first component configured to detect a change in the lipid bilayer resulting from interaction of an assay molecule, or a portion thereof, with the bilayer and a second component configured to detect a modified target molecule resulting from modification of a target molecule by the assay molecule, or portion thereof, where the modification is, at least in part, in the second volume.

Also provided herein, in some embodiments, is a method for assaying an assay molecule, comprising (a) contacting an assay molecule with a first electrolyte volume of a cell-free assay device (b) detecting the presence, absence or amount of an interaction between the lipid bilayer and the assay molecule, or portion thereof and (c) detecting the presence, absence or amount of an interaction between the assay molecule, or portion thereof, with a target molecule, or portion thereof, which target molecule is in the second electrolyte volume.

Also provided herein, in certain embodiments, is a device, comprising a substrate comprising a channel and a binding agent in association with the substrate, a component configured to detect an interaction between an analyte and the binding agent and a component configured to apply or maintain a pressure differential across the channel in the device.

Also provided herein, in certain embodiments, is a method for altering an interaction between an analyte and a binding agent, comprising interacting an analyte with a binding agent in association with a substrate in a system, where the substrate comprises a channel, inducing a pressure differential across the channel and assessing an interaction between the analyte and the binding agent, whereby inducing a pressure differential alters the interaction relative to the interaction assessed without inducing a pressure differential.

Also provided herein, in some embodiments, is a method for enhancing an interaction between an analyte and a binding agent, comprising interacting an analyte with a binding agent attached to a substrate in a system, where the substrate comprises a channel and assessing an interaction between the analyte and the binding agent, where a pressure differential across the channel is at a level at which the interaction is enhanced relative to the interaction at a lower pressure differential.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A shows an embodiment of an aperture followed by an antibody coated channel. FIG. 1B shows an embodiment of a lipid bilayer 30' followed by a channel 13 where a substrate 35 (e.g., a second substrate) can be coated with a suitable binding agent. Both embodiments can be used to monitor the interaction of a toxin or protein with a bilayer (30, 30') followed by monitoring enzymatic activity of a toxin or protein.

FIG. 2A shows a cross-section of a cell-free assay device set up with two apertures separating three different solution chambers (e.g., comprising a first, second and third electrolyte volume). FIG. 2B shows an assay molecule 75 introduced into a first electrolyte volume 10. FIG. 2C illustrates cleavage of a target molecule 85 by an enzyme portion of an assay molecule 80 resulting in a modified target molecule 100 that binds to an immobilized binding agent 20. In some embodiments a cleavage event and/or binding event is monitored between electrodes 22 and 23, using a suitable method of measurement.

FIG. 3A shows the components of a cell-free assay device comprising an assay molecule 75 (e.g., using BoNT) a portion of an assay molecule 80 that forms a pore in a lipid bilayer. FIG. 3B shows a cell-free assay device set up with an EIB separating two different solution chambers (first 10 and second 12 electrolyte volumes). FIG. 3C shows a portion of an assay molecule (e.g., an enzymatic portion) translocating into the second electrolyte volume 12. The insertion of an assay molecule into a lipid bilayer and/or translocation event can be monitored between electrodes 20 and 22. FIG. 3D shows a target molecule 85 in a second electrolyte volume 12, illustrating cleavage of the target molecule resulting in a modified target molecule 100 that binds to a binding agent in a channel comprising a third electrolyte volume 13. The binding event can be monitored between electrodes 22 and 23, using a rectification measurement.

FIG. 4A shows a cell-free assay device configuration comprising an internal probe 25 that can be used to monitor the activity of a toxin or protein, or portion thereof, that has inserted into and/or translocated through the PLB. FIG. 4B shows a cell-free assay device configuration comprising a detector assembly comprising an excitation source 52 and a detector portion (e.g., a photocell or CMOS imager) 54. In some embodiments the GNM is transparent to electromagnetic radiation 60. Any suitable arrangement of an excitation source and detector can be used. In some embodiments the source and detector can be on the same or opposite sides of the chamber that is being analyzed.

DETAILED DESCRIPTION

Provided herein, in some embodiments, are a cell-free assay devices and methods to detect and/or characterize an assay molecule (e.g., a protein, a toxin, a modifier or inhibitor thereof). In some embodiments, an assay molecule comprises a toxin with pore-forming potential and and/or proteinase activity. In some embodiments, an assay molecule comprises a botulinum toxin and/or an inhibitor thereof. In some embodiments cell-free assay devices described herein comprise a lipid bilayer, an aperture, a channel and/or a GNM.

The term "cell-free assay device" refers to a device where the structural and functional components of the device do not include a cell (e.g., a cell comprising an intact cell membrane) derived from a living organism. In some embodiments a cell-free assay device and/or a lipid bilayer of a device described herein comprises naturally occurring lipids. Non-limiting examples of a living cell include a eukaryotic cell, prokaryotic cell, an egg (e.g., a frog egg), a cell without a nucleus, a ghost cell, a cell wherein one or more of the cell contents have been removed leaving the lipid bilayer of the cell intact, or the like. In some embodiments a cell may be introduced into a cell-free assay device (e.g., into an electrolyte volume of a device). The introduction of a cell into a cell-free assay device may be intentional (e.g., a component of a sample may comprise a cell) or un-intentional (e.g., a cell may be a contaminant of a sample).

Figure 1A:
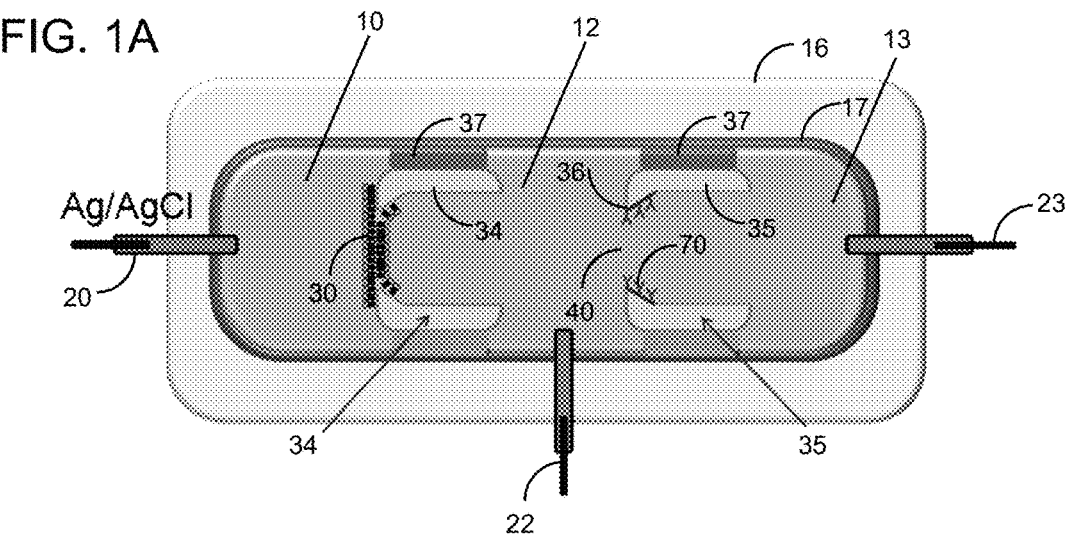
FIG. 1A shows an embodiment of a cross-section of a cell-free assay device comprising a planar lipid bilayer (PLB) 30 and FIG. 1B shows an embodiment of a cell-free assay device comprising an encapsulated lipid bilayer.
Figure 1B:
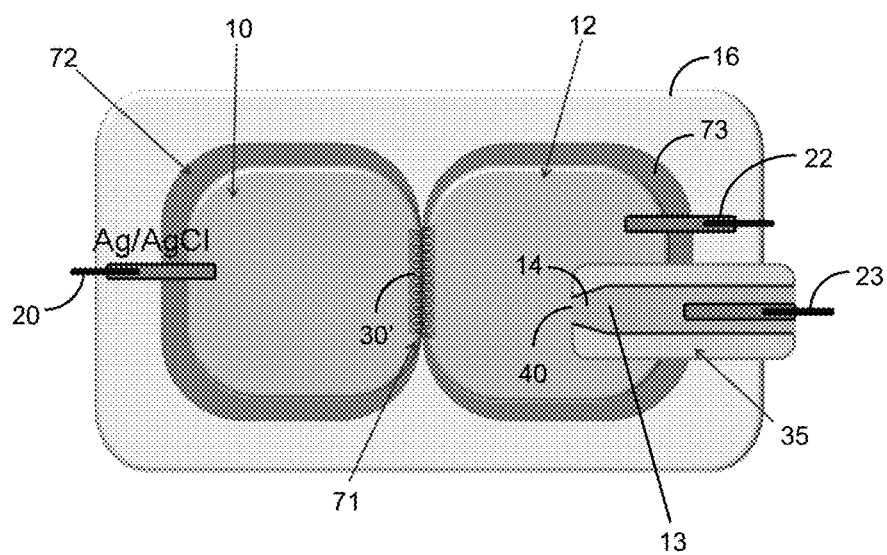

Provided herein, in some embodiments, is a cell-free assay device comprising a first electrolyte volume and a second electrolyte volume. In certain embodiments a first electrolyte volume 10 is separated from a second electrolyte volume 12 by a lipid bilayer (e.g., 30, 30'). Sometimes a first electrolyte volume is separated from a second electrolyte volume by an aperture. In certain embodiments a first electrolyte volume is separated from a second electrolyte volume by a channel. In some embodiments a cell-free assay device comprises a lipid bilayer (e.g., 30, 30') spanning across an aperture 40 in a substrate 34 (FIG. 1, e.g., a first substrate). In some embodiments a cell-free assay device does not comprise a lipid bilayer. In some embodiments a cell-free assay device comprises a component configured to detect a change in a lipid bilayer. Non-limiting examples of a change in a lipid bilayer include: a structural change; loss of integrity of a lipid bilayer; insertion, removal or translocation of an assay molecule, or portion thereof (e.g., a protein, a pore, a pore forming protein, a carbohydrate, a nucleic acid, a lipid (e.g., a fatty acid, glycerolipid, phospholipid (e.g., a triglyceride), glycerophospholipid, sphingolipid, saccharolipid, polyketide, sterol lipid (e.g., cholesterol or a derivative thereof), prenol lipid, the like or combinations thereof) into, from or through a lipid bilayer; insertion, removal or translocation of a pathogen, parasite, virus, bacteria, or part thereof; the like or a combination thereof. In some embodiments a cell-free assay device comprises a component configured to detect a change between one or more electrolyte volumes. A "change" as used herein can mean the absence or presence of a change. In some embodiments a cell-free assay device comprises a component configured to detect a change between a first electrolyte volume 10 and a second electrolyte volume 12, a second electrolyte volume 12 and a third electrolyte volume 13 and/or between a first and a third electrolyte volume. Non-limiting examples of a change between two or more electrolyte volumes include an electrical change (e.g., a change in conductance, resistance, electrical potential, impedance, current, current rectification, ion current rectification, the like, or a combination thereof), a change in electromagnetic radiation (e.g., alpha, beta or gamma radiation, X-ray radiation, ultraviolet radiation, visible radiation (e.g., visible light, fluorescent light), infrared radiation, terahertz radiation, microwave radiation, radio waves, the like, or a combination thereof), a change in magnetism (e.g., changes in magnetic fields), a change in temperature, a change in pressure, a change in volume, the like or combinations thereof.

In some embodiments a change in a lipid bilayer comprises (i) insertion of an assay molecule, or a portion thereof, into the bilayer, (ii) translocation of an assay molecule, or a portion thereof, through a bilayer, (iii) binding of an assay molecule, or a portion thereof, to a bilayer, (iv) binding of an assay molecule, or a portion thereof, to at least one receptor on a lipid bilayer, (v) association of an assay molecule or a portion thereof with the bilayer, or a combination thereof. The term "translocation" sometimes means movement of an assay molecule, or portion thereof, from one side of a lipid bilayer to another side of a lipid bilayer. In some embodiments translocation comprises movement of an assay molecule or portion thereof through a pore in a lipid bilayer. In some embodiments, an assay molecule or portion thereof comprises a pore (e.g., a pore in a lipid bilayer). In some embodiments translocation comprises movement of an assay molecule or a portion thereof from a first electrolyte volume, through a pore in a lipid bilayer, and into a second electrolyte volume. In certain embodiments, an assay molecule is contacted with a first electrolyte volume and a portion of the assay molecule translocates through a pore in a lipid bilayer into a second electrolyte volume. In some embodiments a change in a lipid bilayer results from an interaction of an assay molecule, or a portion thereof, with a lipid bilayer. In some embodiments an interaction comprises (i) insertion of an assay molecule, or a portion thereof, into the bilayer, (ii) translocation of an assay molecule, or a portion thereof, through a bilayer, (iii) binding of an assay molecule, or a portion thereof, to a bilayer, (iv) binding of an assay molecule, or a portion thereof, to at least one receptor on a lipid bilayer, (v) association of an assay molecule or a portion thereof with the bilayer, or a combination thereof. In certain embodiments, insertion of an assay molecule into a lipid bilayer comprises insertion of a pore into a lipid bilayer.

In some embodiments a component configured to detect a change comprises one or more electrodes (e.g., electrode pairs), probes, detectors (e.g., detector assemblies), or combinations thereof. In some embodiments, a component configured to detect a change comprises one or more electrolyte volumes, a GNM, channels, apertures, lipid bilayers, substrates, housings, binding agents, target molecules, assay molecules, pressure control systems, microprocessors, computers or microprocessor controlled apparatuses, software, (e.g., a non-transitory computer-readable storage medium with an executable program stored thereon, wherein the program instructs a microprocessor to perform a function), a system (e.g., a system comprising one or more microprocessors and memory), the like or a combination thereof.

In some embodiments a cell-free assay device comprises a first electrolyte volume 10 comprising an electrode 20, a second electrolyte volume 12 comprising an electrode 22 and/or a third electrolyte volume 13 comprising an electrode 23. In some embodiments an electrolyte volume comprises a probe 25. In some embodiments a cell-free assay device comprises a channel 15 that, in certain embodiments, separates an electrolyte volume (e.g., a second electrolyte volume 12) from another electrolyte volume (e.g., a third electrolyte volume 13). In some embodiments an electrolyte volume (e.g., a second electrolyte volume) contacts another electrolyte volume (e.g., a third electrolyte volume) at an aperture 40. In some embodiments a first electrolyte volume does not contact a second electrolyte volume. In some embodiments a second electrolyte volume does not contact a third electrolyte volume. In some embodiments a cell-free assay device comprises one or more solid supports, substrates (e.g., 17, 34, 35) and/or a housing 16 (e.g., a chamber). In some embodiments a solid support or substrate 35 comprises a binding agent 70 (e.g., antibodies). In some embodiments a binding agent is attached to a substrate 35 via a linker 36. In some embodiments an aperture and/or a channel comprises a binding agent. In some embodiments the interior of a chamber (e.g., the interior substrate of a chamber) comprises a binding agent. For example, sometimes a chamber comprises a second or third electrolyte volume and the chamber comprises a binding agent. In some embodiments, a binding agent 70 is configured to bind to a modified target molecule (e.g. cleaved SNAP-25 in the case of the BoNT/A toxin). Non-limiting embodiments of a cell-free assay device are shown in FIG. 1-5).

In some embodiments a cell-free assay device comprises an encapsulated lipid bilayer. An encapsulated lipid bilayer can be generated by any suitable method. In some embodiments a cell-free assay device comprises an encapsulated lipid bilayer where a first electrolyte volume is formed by a first droplet 72 (e.g., a lipid monolayer), comprising a lipid monolayer encasing a first electrolyte volume and a second electrolyte volume is formed by a second droplet 73 comprising a lipid monolayer encasing a second electrolyte volume. In some embodiments a lipid bilayer 30' is formed at the interface 71 of a first droplet 72 and a second droplet 73. The size (e.g., diameter) and shape of an encapsulated lipid bilayer can be determined by a suitable method. In some embodiments, the size and/or shape of an encapsulated lipid bilayer is limited by an aperture (e.g., an aperture that defines and/or limits a contact area between two lipid monolayers. In some embodiments, the size and/or shape of an encapsulated lipid bilayer is not limited by an aperture. In some embodiments, the shape of an encapsulated lipid bilayer is determined by an amount of mechanical pressure applied to contact the first and second monolayers.

In some embodiments a cell-free assay device comprises an encapsulated lipid bilayer where a first electrolyte volume 10 is formed by a first droplet 72 (e.g., a lipid monolayer), comprising a lipid monolayer encasing a first electrolyte volume and second electrolyte volume 12 is formed by a second droplet 73 comprising a lipid monolayer encasing a second electrolyte volume. In certain embodiments, a lipid bilayer 30 is formed at the interface of a first droplet and a second droplet. In certain embodiments, the first and second droplets are located within an oil 94. In certain embodiments the cell-free assay is located within a housing 16. In certain embodiments, the cell-free assay comprises a detector 54. In certain embodiments, the detector further comprises an excitation source 52. In certain embodiments, the proteinase or enzymatic activity of an active toxin or protein is measured after it, or a portion thereof, has translocated through the lipid bilayer 30' and is measured using a detector 54 further comprising an excitation source 52.

In some embodiments a cell-free assay device comprises one or more apertures 40. A cell-free device often comprises an aperture and/or a substrate. In some embodiments an aperture comprises a lipid bilayer. Certain embodiments of apertures, nanopores and uses thereof are described in U.S. patent application Ser. No. 13/414,636 filed on Mar. 7, 2012, entitled "METHODS FOR VOLTAGE-INDUCED PROTEIN INCORPORATION INTO PLANAR LIPID BILAYERS," naming Ryan Dunnam, Geoffrey Barrall and Melissa Poquette as inventors, and designated by attorney docket no. EBS-1002-UT, the entirety of which herein is incorporated by reference, including all text, tables and drawings.

Device Substrate

In some embodiments a cell-free assay device comprises one or more substrates. As used herein, a "substrate" refers to an insoluble support or coating. In some embodiments, a substrate comprises a GNM or AMGNM. In some embodiments, a substrate comprises a suitable material, non-limiting examples of which include silicon (e.g., Si, $SiO_2$, $Si_3N_4$), silica, alumino silicate, glass (e.g. glass, controlled-pore glass (CPG)), nylon, Wang resin, Merrifield resin, Sephadex, Sepharose, cellulose, magnetic beads, Dynabeads, a metal or metal surface (e.g. steel, metal alloys, gold, silver, stainless steel, aluminum, silicon and copper), alumina, nitrides, diamond, quartz, sapphire metals, ceramics, a plastic or polymer (e.g., polyethylene, polycarbonate, polypropylene, polystyrene, polyvinyl chloride (PVC), polymethyl metaacrylate (PMMA, Plexiglas), polyamide, polyester, polytetrafluoroethylene, Teflon, polyvinylidenedifluoride (PVDF)), a cyclo olefin polymer, a gold coated cyclo olefin polymer, beads, wafers (e.g., silicon wafers), various coatings (e.g., fluorocarbon polymers (e.g., fluorinated ethylene-propylene, polytetrafluoroethylene), photoresist, DMDCS (dimethyldichlorosilane)), the like or combinations thereof. Non-limiting examples of glass types suitable for a substrate include fused silica glass, ninety-six percent silica glass, soda-lime silica glass, borosilicate glass, aluminosilicate glass, lead glass, doped glass comprising desired additives, functionalized glass comprising desired reactive groups, the like and combinations thereof. In some embodiments the substrate comprises a mineral. Non-limiting examples of minerals (e.g., quartz) suitable for a substrate include quartz, tridymite, cristobalite, coesite, lechatelierite, stishovite, the like and combinations thereof. In some embodiments a substrate comprises a suitable coating. In some embodiments a substrate is a coating. Sometimes substrate materials are inert to the operation of a cell-free assay device. A substrate can be in a suitable form, non-limiting examples of which include a bead, chip, capillary, an aperture, channel, tube, a cylinder, cone, nanopore device, plate, chamber, housing, disk, filter, dipstick, membrane, wafer, comb, pins, a substantially flat surface, the like or combinations thereof. Sometimes a substrate comprises a surface configured to receive or link a molecule (e.g., an assay molecule, a target molecule, a binding agent, the like, or a combination thereof).

In certain embodiments, a substrate (e.g. a substrate of a cell-free assay device) comprises a suitable hydrophobic material, such as Teflon, or it may be modified in a manner that renders one or more surfaces of the substrate (e.g., substrate channel interior, substrate channel exterior) hydrophobic (e.g. mildly hydrophobic, substantially hydrophobic). In some embodiments one or more surfaces of a substrate are coated with a coating. Non-limiting examples of a coating include a substrate, and hydrophobic substances, including without limitation an alkyl silane substance (e.g., 3-cyano-propyldimethylchlorosilane). Any suitable silane substance can be selected to render a substrate surface more hydrophobic and support interaction with lipids for formation of a lipid structure that spans a substrate aperture. A substrate can be manufactured from a pure substance or can be manufactured from a composite material.

A substrate sometimes comprises a coating that modifies the surface of an aperture and/or channel. In some embodiments, a substrate comprises a surface that includes a hydrophobic substance. In certain embodiments, a substrate comprises a surface that includes a hydrophilic substance. In some embodiments, a substrate comprises a surface that includes hydrophobic and hydrophilic substances.

Thus, an entire substrate, and/or one or more portions of a substrate can be treated or coated to adopt certain desirable characteristics, in some embodiments. In certain embodiments, the treatment or coating enhances formation of lipid structures across the aperture of the substrate. Physical and/or chemical modification of the surface properties of a substrate include, but are not limited to, modification of the electrical charge density, changes to the hydrophobicity, changes to the hydrophilicity, the like and combinations thereof. Any suitable substance can be utilized to modify one or more interior and/or exterior surfaces of the substrate. Non-limiting examples of suitable materials for modification of one or more substrate surfaces include silanes, silanes terminating in a cyano group, silanes terminating in a methyl group, thiols, the like, or combinations thereof. In some embodiments, an exterior surface of a substrate may be modified by a first entity. In certain embodiments, an interior surface of a substrate may be modified by a second entity. In some embodiments, the first and the second entity may be the same entities, and in certain embodiments, the first and the second entity may be different entities. In some embodiments utilizing a glass substrate, the first or second entities that can be used to modify the interior or exterior surfaces of a substrate include a variety of glass-reactive species, e.g., 3-cyano-propyldimethylchlorosilane, that react with the silanol groups of the glass surface. In certain embodiments, a substrate comprises a surface that includes a metal coating. For example, a substrate could be made of glass and then coated in gold.

In some embodiments the thickness of a substrate typically ranges from about 100 nanometer (nm) to 5 millimeters (mm) in thickness (e.g., about 100 nm, about 150 nm, about 200 nm, about 250 nm, about 300 nm, about 350 nm, about 400 nm, about 500 nm, about 600 nm, about 700 nm, about 800 nm, about 900 nm, about 1000 nm (e.g., about 1 µm), about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm, 100 µm, about 110 µm, about 120 µm, about 130 µm, about 140 µm, about 150 µm, about 175 µm, about 200 µm, about 225 µm, about 250 µm, about 300 µm, about 350 µm, about 400 µm, about 450 µm, about 500 µm, about 600 µm, about 700 µm, about 800 µm, about 900 µm, 1000 µm (e.g. 1 mm), about 2 mm, about 3 mm, about, about 4 mm, or about 5 mm).

Device Aperture

In some embodiments a cell-free assay device comprises one or more apertures. Sometimes a channel comprises an aperture. An aperture can be of any suitable geometry, and sometimes comprises a substantially circular, oval, square, rectangular, rhomboid, parallelogram, or other like cross-section. An aperture can be of any suitable profile, and sometimes has a substantially cylindrical or conical (e.g., tapering or expanding conical) profile. In some embodiments a nanopore device (e.g., a GNM) comprises an aperture and/or a channel. The term "nanopore" as used herein often refers to an aperture or a device comprising an aperture In some embodiments an aperture is located at a proximal and/or distal end of a channel. In certain embodiments, a substrate comprises one or more apertures that separate two or more electrolyte volumes. In certain embodiments, an aperture separates a first electrolyte volume and a second electrolyte volume. In certain embodiments, an aperture separates a second electrolyte volume and a third electrolyte volume.

In certain embodiments a cell-free assay device comprises one or more apertures. In certain embodiments, a cell-free assay device comprises two or more apertures. In certain embodiments a cell-free assay device comprises between 1 and 10 apertures. In certain embodiments a cell-free assay device comprises between 5 and 100 channels. In certain embodiments a cell-free assay device comprises between 5 and 1,000 channels. In certain embodiments a cell-free assay device comprises between 5 and 10,000 channels. Often an aperture separates two or more fluid reservoirs.

In certain embodiments, an aperture comprises a suitable substrate. In some embodiments, an aperture comprises a glass or quartz substrate. In some embodiments an aperture comprises a coating. In some embodiments an aperture comprises a linker.

In certain embodiments, an aperture comprises a diameter of about 0.25 nanometer (nm) to about 10 millimeters (mm), about 0.25 nm to about 1 mm, about 0.25 nm to about 100 um, about 0.25 nm to about 50 µm or about 0.25 nm to about 10 um. In some embodiments an aperture comprises a diameter of about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 2 µm, about 3 µm, about 4

μm, about 5 μm, about 10 μm, about 15 μm, about 20 μm, about 25 μm, about 30 μm, about 35 μm, about 40 μm, about 45 μm, or about 50 μm.

In certain embodiments, a substrate, a channel, an aperture and/or a nanopore or nanopore device is as described in U.S. Pat. No. 7,777,505, which is hereby incorporated by reference.

Lipids and Lipid Bilayer

In some embodiments a cell-free assay device comprises a lipid bilayer. In some embodiments a lipid bilayer can mimic a cell membrane. In some embodiments a lipid bilayer is synthetic (e.g., produced by synthesis, not isolated). In some embodiment a lipid bilayer is obtained from a cell. In some embodiments, a lipid bilayer is a planar lipid bilayer that spans across an aperture or well in a substrate. In certain embodiments, a planar lipid bilayer is supported across an aperture or well in a substrate. In some embodiments a lipid bilayer separates an electrolyte volume from another electrolyte volume.

In certain embodiments, a lipid bilayer is an encapsulated lipid bilayer (EIB) or a droplet interface bilayer (DIB). In certain embodiments, an EIB or DIB comprises a first lipid monolayer and a second lipid monolayer pressed together to form a lipid bilayer along a portion of the monolayers where the two monolayers contact each other. In some embodiments an encapsulated lipid bilayer comprises a first droplet formed by a first lipid monolayer and a second droplet formed by a second lipid monolayer that are in contact along at least a portion of the first and second monolayers to form an encapsulated lipid bilayer. In some embodiments a first droplet forms a first electrolyte volume and a second droplet forms a second electrolyte volume. For example, a first lipid monolayer can form a first droplet that contains a first electrolyte volume surrounded by the first lipid monolayer and a second lipid monolayer can form a second droplet that comprises a second electrolyte volume surrounded by the second lipid monolayer. The two droplets can be pressed together, in some embodiments, by a mechanical apparatus and a lipid bilayer forms at where the two droplets make contact. In some embodiments the size of the contact area can be controlled and/or defined. For example, the two droplets may only be allowed to contact each other through an aperture where a lipid bilayer forms. In such embodiments, the diameter and profile of the aperture defines the diameter and profile of the lipid bilayer. Volumes, monolayers, and bilayer leaflets may be symmetrical or asymmetrical in composition.

In some embodiments a lipid droplet is contained within a housing 16. In certain embodiments a chamber comprises and/or confines a lipid droplet. In some embodiments a housing comprises a substrate or a coating. In some embodiments a housing comprises a chamber (e.g., a chamber defining a fixed volume). In certain embodiments, the volume of a chamber can be changed, for example by mechanically moving parts of the chamber. In some embodiments the pressure within a chamber can be altered or changed by a pressure control system.

In certain embodiments, the composition of a lipid bilayer is comprised of natural and/or synthetic lipids. Non limiting examples of lipids include phosphocholine, phosphoethanolamine, phosphoserine, and the like. In some embodiments, a lipid bilayer is any suitable lipid bilayer. A lipid can be dispersed in an organic solvent (e.g. squalene, hexadecane, decane, pentane, hexane, and the like). Bilayer additives may also be incorporated into a bilayer (e.g. cholesterol, polyethylene glycol, and the like) to stabilize the bilayer and customize fluidity. Non limiting examples of additives include cell surface receptors, gangliosides, ceramides, sphingomyelin, glycosphingolipids, the like or combinations thereof. Additives can be integrated into the bilayer to initiate toxin/protein insertion. To further control the bilayer properties, pressure gradients can be employed to control bilayer curvature or influence pressure-gradient driven flow. To further control the bilayer properties, a voltage bias (AC and/or DC) can be employed to control the thickness of the bilayer and/or influence migration or the movement of charged species under an applied bias.

In certain embodiments, the lipid composition of a device often is relatively stable to mechanical disturbances, and can have a lifetime in excess of two weeks. Additionally, a device can be made with a lipid composition that is readily formed over or in an aperture and has a relatively small surface area, which can give rise to favorable electrical characteristics.

In some embodiments, lipids, having various chain lengths or various structures of polar heads, can be used to form various structures suitable for use with a device. For example, a monolayer, bilayer, or a combination of monolayer or bilayer can be formed on one or more exterior and/or interior surfaces of a substrate. In certain embodiments, a lipid composition that spans across the substrate aperture is a combination of a lipid bilayer and monolayer. In various embodiments, a lipid monolayer deposited on the exterior surface of a substrate and a lipid monolayer deposited on the interior surface of a substrate that joins together at about the edge of an aperture can form a lipid bilayer spanning or suspended across the aperture. The bilayer formed across an aperture sometimes is referred to as a "spanning lipid bilayer" herein.

In a spanning bilayer structure, a bilayer often is present across the substrate aperture or well and a monolayer can be present on substrate surfaces (e.g., chemically modified surfaces). An inserted protein (e.g., a protein pore, a toxin) can diffuse into a bilayer and across a bilayer but often cannot leave this area to enter the lipid monolayer. Insertion of a toxin or protein often occurs only in a bilayer region. A thin layer (e.g., about 1 to about 10 nm thick) comprising solvent and ions sometimes is formed between a spanning lipid bilayer and one or more surfaces of the substrate. The thickness of this layer is defined as the distance between the exterior surface and the lipid bilayer and often plays a role in determining the resistance of the bilayer seal and the stability and fluidity of the bilayer. A spanning bilayer also sometimes includes an annulus formed between monolayers and an aperture surface, which can comprise solvent (e.g., FIG. 15 of U.S. Pat. No. 7,777,505).

While a device often comprises a lipid composition separating a first electrolyte volume from a second electrolyte volume, this composition may comprise any suitable amphiphilic materials into which a protein can be incorporated. A protein often is inserted into a structure (e.g., monolayer and/or bilayer) formed by the lipid or amphiphilic material composition. A protein that is inserted into the structure can be water soluble, detergent-solubilized or incorporated into a lipid vesicle, liposome or micelle in some embodiments.

An amphiphilic molecule generally is composed of a hydrophobic part and a polar part. The terms "amphiphilic material" or "amphiphilic materials" refer to materials made of molecules having a polar, water-soluble group attached to a nonpolar, water-insoluble hydrocarbon chain. Amphiphilic materials sometimes can be polymers. The amphiphilic materials may be a pure substance or a mixture of different amphiphilic materials. The polymeric materials may be a polymer with a uniform molecular weight distribution, or a polymer with a non-uniform molecular weight distribution, or a mixture of polymers which comprise different monomers. Non-limiting examples of amphiphilic molecules include lipids, detergents, surfactants, proteins, polysaccharides, and other chemical or biochemical materials that can be rendered amphiphilic. The terms "detergent" or "detergents" as used herein refer to a surfactant or a mixture of surfactants. The terms "surfactant" or "surfactants" as used herein refers to any compound that (i) lowers the surface tension of a liquid, allowing easier spreading, and/or (ii) lowers the interfacial tension between two liquids, or between a liquid and a solid. Surfactants may act as: detergents, wetting agents, emulsifiers, foaming agents, and dispersants. Surfactants often are categorized as ionic (anionic or cationic), zwitterionic or amphoteric, or non-ionic. Non-limiting examples of surfactants include ammonium lauryl sulfate, sodium lauryl sulfate (SDS), sodium laureth sulfate (e.g., also known as sodium lauryl ether sulfate (SLES)), sodium myreth sulfate, dioctyl sodium sulfosuccinate, perfluorooctanesulfonate (PFOS), perfluorobutanesulfonate, alkyl benzene sulfonates, alkyl aryl ether phosphate, alkyl ether phosphate, fatty acid salts (e.g., soaps), sodium stearate, sodium lauroyl sarcosinate, perfluorononanoate, perfluorooctanoate, octenidine dihydrochloride, cetyl trimethylammonium bromide (CTAB), cetyl trimethylammonium chloride (CTAC), Cetylpyridinium chloride (CPC), polyethoxylated tallow amine (POEA), benzalkonium chloride (BAC), benzethonium chloride (BZT); 5-Bromo-5-nitro-1,3-dioxane, dimethyldioctadecylammonium chloride, dioctadecyldimethylammonium bromide, 3-[(3-Cholamidopropyl)dimethylammonio]-1-propanesulfonate (e.g., CHAPS), cocamidopropyl hydroxysultaine, amino acids, imino acids, cocamidopropyl betaine, lecithin, fatty alcohols (e.g., cetyl alcohol, stearyl alcohol, and the like), the like and combinations thereof.

A lipid molecule typically comprises at least one hydrophobic chain and at least one polar head. When exposed to an aqueous environment, lipids often will self assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A lipid bilayer typically comprises a sheet of lipids, generally two molecules thick, arranged so the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect, which creates an energetically unfavorable interaction between the hydrophobic lipid tails and the surrounding water. Lipid bilayers typically are held together entirely by non-covalent forces that do not involve formation of chemical bonds between individual molecules. Lipid bilayers generally also are impermeable to ions, which allow cells to regulate various processes that involve salt concentrations or gradients and intracellular pH by pumping ions across cell substrates using ion transport mechanisms.

In some embodiments, lipid bilayers are natural, and in certain embodiments lipid bilayers are artificially generated (e.g., synthetic). Natural bilayers often are made mostly of phospholipids, which have a hydrophilic head and two hydrophobic tails, and form a two-layered sheet as noted above, when exposed to water or an aqueous environment. The center of this bilayer comprises almost no water and also excludes molecules like sugars or salts that dissolve in water, but not in oil. Artificial bilayers (e.g., synthetic lipid bilayers, sometimes also referred to as "model lipid bilayers") are any bilayers assembled through artificial means, as opposed to bilayers that occur naturally (e.g., cell substrates, lipid bilayers that cover various sub-cellular structures). An artificial bilayer can be made with synthetic and/or natural lipids, thus the process, not the material, defines an artificial or model system. The simplest model systems comprise only a single pure synthetic lipid. The artificial bilayer also may comprise a hydrophobic solvent, such as decane, hexadecane, pentane or other solvents and combinations thereof, that is used to disperse the lipid during bilayer formation and stabilize the formation of lipid bilayers across apertures in hydrophobic materials. The simplicity of a single lipid system is advantageous when determining physical or mechanical properties of bilayers. Model bilayers with greater physiological relevance can be generated utilizing mixtures of several synthetic lipids or, as mentioned, with natural lipids extracted from biological samples.

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of substrate constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), surfactants, the like and combinations thereof.

Lipid tails also can affect lipid composition properties, by determining the phase of the bilayers, for example. A bilayer sometimes adopts a solid gel phase state at lower temperatures and undergoes a phase transition to a fluid state at higher temperatures. The packing of lipids within a bilayer also affects its mechanical properties, including its resistance to stretching and bending. Properties, such as stretching, bending or temperature induced phase transitions, have been studied with artificial "model" bilayers.

A device may include one or more types of molecules other than phospholipids. For example, cholesterol, which helps strengthen bilayers and decreases bilayer permeability can be included. Cholesterol also helps regulate the activity of certain integral substrate proteins.

Different types or forms of lipid compositions (e.g., monolayers and/or bilayers) can be found naturally or generated artificially. Non-limiting examples of lipid compositions include monolayers (e.g., micelles) and bilayers including "black PLBs", vesicles (e.g., sometimes referred to as "liposomes"), supported lipid bilayers, spanning lipid bilayers, linear lipid bilayers, droplet interfacial bilayers, encapsulated lipid bilayers and the like.

A vesicle is a lipid bilayer configured as a spherical shell enclosing a small amount of water or aqueous solution and separating it from the water or aqueous solution outside the vesicle. Because of the fundamental similarity to a cell substrate, vesicles have been used to study the properties of lipid bilayers. Vesicles also are relatively easy to make, adding to their attractiveness as an experimental system. A sample of dehydrated lipid spontaneously forms vesicles, when exposed to water. Spontaneously formed vesicles can be either unilamellar (single-walled) or multilamellar (many-walled) and are of a wide range of sizes from tens of nanometers to several micrometers.

A liposome is an artificially prepared vesicle, and also comprises a lipid bilayer, unlike micelles which comprise a lipid monolayer. Liposomes also can be made of naturally occurring or synthetic lipids, including phospholipids. There are four types of liposomes: MLV (multilamellar vesicles), SUV (Small Unilamellar Vesicles), LUV (Large Unilamellar Vesicles) and GUV (Giant Unilamellar Vesicles). Liposomes may also be used to form PLBs on a surface or across apertures.

Electrolyte Volumes

In some embodiments a cell-free assay device comprises one or more electrolyte volumes. In some embodiments, a cell-free assay device comprises two or more electrolyte volumes. In some embodiments a cell-free assay device comprises 2, 3, 4, 5, 6, 7, 8, 9, 10, 11, 12 or more electrolyte volumes. In some embodiments a cell-free assay device comprises 3 electrolyte volumes. In some embodiments a cell-free assay device comprises 2 electrolyte volumes.

In certain embodiments, an electrolyte volume is a liquid configured, in part, to conduct electricity. In some embodiments an electrolyte volume comprises one or more suitable electrolytes. An electrolyte can be any element, compound or molecule that ionizes when dissolved in a suitable solvent. An electrolyte sometimes comprises a suitable solvent (e.g., an aqueous solvent, e.g., water). In certain embodiments, an electrolyte comprises an ionic salt, acid and/or a base. Non limiting examples of ionic salts include sodium salts (e.g., sodium chloride (NaCl), sodium bromide (NaBr)), potassium salts (e.g., potassium chloride (KCl)), lithium salts (e.g., lithium chloride (LiCl)), cesium salts (e.g., cesium chloride (CsCl)), rubidium salts (e.g., rubidium chloride (RbCl)), magnesium salts (e.g., magnesium chloride (MgCl2)), calcium salts (e.g., calcium chloride (CaCl2), phosphate salts (e.g., hydrogen phosphate), carbonate salts (e.g., hydrogen carbonate), the like, and combinations thereof. In some embodiments an electrolyte comprises a charged macro molecule, non-limiting examples of which include nucleic acids, polypeptides and certain synthetic polymers (e.g., polystyrene sulfonate), often termed as polyelectrolytes, which often contain charged functional groups. In some embodiments an electrolyte comprises an ionic liquid. Non-limiting examples of ionic liquids include 1-Butyl-3-methylimidazolium hexafluorophosphate, 1-butyl-3,5-dimethylpyridinium bromide, the like, or combinations thereof.

In some embodiments an electrolyte volume comprises a suitable buffer. Non limiting examples of buffers include dimethylglutaric acid (DMG), 3-{[tris(hydroxymethyl)methyl]amino}propanesulfonic acid (TAPS), N,N-bis(2-hydroxyethyl)glycine (Bicine), tris(hydroxymethyl)methylamine (TRIS), N-tris(hydroxymethyl)methylglycine (Tricine), 3-[N-Tris(hydroxymethyl)methylamino]-2-hydroxypropanesulfonic Acid (TAPSO), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid (Succinic acid), the like, or a combination thereof. An electrolyte volume can be adjusted to a suitable pH, which may be done asymmetrically or symmetrically between two or more electrolyte volumes. In some embodiments an electrolyte volume comprises an additive, salt and/or a compound to adjust the polarity, conductivity and/or viscosity. In some embodiments an electrolyte volume comprises an additive, salt and/or compound to provide optimal conditions for a protein (e.g., a toxin), an interaction (e.g., a binding interaction, a pore forming interaction) and/or a reaction (e.g., an enzymatic reaction). In certain embodiments, an electrolyte volume comprises an organic solvent (e.g. acetonitrile) and/or an alcohol (e.g., a polyol, (e.g., trifluoroethanol, glycerol), ethanol, 2-propanol, and the like). An electrolyte volume can also comprise additional solutes and/or salts (e.g., Urea, $ZnCl_2$, $CaCl_2$), chelating agents (e.g., ethylenediaminetetraacetic acid (EDTA), EGTA, and the like), reducing agents (e.g., tris(2-carboxyethyl)phosphine (TCEP), dithiothreitol (DTT), 2-mercaptoethanol, and the like), chaotropic agents, macromolecular exclusion molecules (e.g., macromolecular crowding molecules), chaperones, surfactants and/or detergents (e.g., sodium dodecyl sulfate (SDS), Triton X-100, and the like), enzymes/catalysts (e.g., trypsin, chymotrypsin, and the like), enzyme cofactors, protein stabilizers (e.g. BSA, HSA, and the like). In certain embodiments an electrolyte volume comprises a protein, carbohydrate, a nucleic acid, and/or a lipid. In some embodiments an electrolyte volume comprises an assay molecule, an analyte, a target molecule, a modified target molecule, a neutralizing therapeutic (e.g., an inhibitor), and/or a binding agent (e.g., an antibody, or portion thereof). In some embodiments an electrolyte volume (e.g., a first, second or third electrolyte volume) comprises a target molecule. In some embodiments a second electrolyte volume comprises a target molecule. In some embodiments an electrolyte volume (e.g., a first, second and/or a third electrolyte volume) comprises an immobilized target molecule.

In certain embodiments various parameters (e.g., pH, conductivity, temperature, pressure, volume, solute concentration, and the like) of one or more electrolyte volumes can be individually and/or collectively controlled, changed, adjusted and/or maintained. In some embodiments, various parameters can differ between one or more electrolyte volumes in a cell-free assay device.

An electrolyte volume can comprise a suitable volume of a liquid. In some embodiments a volume of an electrolyte volume is between about 50 liters and about 0.01 μl, between about 1 liter and about 0.1 μl, between about 500 ml and about 0.1 μl, between about 100 ml and about 0.1 μl, between about 50 ml and about 0.1 μl, between about 50 ml and about 1 μl, between about 10 ml and about 1 μl, between about 1 ml and about 1 μl, between about 1 ml and about 10 μl, or between about 1 ml and about 100 μl. In some embodiments a volume of an electrolyte volume is about 200 ml, 100 ml, 50 ml, 20 ml, 10 ml, 5 ml, 2 ml, 1 ml, 500 μl, 100 μl, 50 μl, 20 μl or about 10 ul. In some embodiments an electrolyte volume is a defined, pre-determined and/or a known volume of a liquid or solution. In some embodiments the volume of an electrolyte volume is defined by a chamber, a housing, the like or a combination thereof where the chamber and/or housing comprises an electrolyte volume. In some embodiments a housing 16 comprises an electrolyte volume. In some embodiments an electrolyte volume is contained within a housing 16. In certain embodiments a chamber comprises and/or confines an electrolyte volume.

In some embodiments a housing comprises a chamber (e.g., a chamber defining a fixed electrolyte volume). In certain embodiments, a volume of a chamber can be changed, for example by mechanically moving parts of the chamber. In some embodiments a pressure within a chamber and/or a housing can be altered or changed by a pressure control system or pressure regulating device.

A chamber can comprise any structure that defines and comprises an aqueous volume. Non limiting examples of a chamber include a hydrophobic fluid, an oil, a GNM, an AMGNM, a substrate, a structure, a substrate and an oil, a micelle, a lipid, a lipid monolayer encapsulated by an oil, a lipid droplet, the like or a combination thereof. A chamber can comprise one or more components, non-limiting examples of which include an aperture, a pore, a substrate, a structure, one or more walls, a channel, a lipid bilayer, a hydrophobic fluid, and the like. In some embodiments a chamber contains, surrounds and/or isolates an electrolyte volume while, in some embodiments, allows transfer of some of its contents (e.g. salts, ions, anions, small molecules, peptides, polymers, solvent, current) to another chamber through a lipid bilayer, a pore, a channel and/or an aperture.

In some embodiments a cell-free assay device comprises one or more apertures. In some embodiments, a cell-free assay device comprises 100 or more apertures. In some embodiments, a cell-free assay device comprises two or more apertures. In some embodiments a cell-free assay device comprises 1, 2, 3, 4, 5, 6, 7, 8, 9, 10 or more apertures. In some embodiments a cell-free assay device comprises 2 apertures. In some embodiments a device comprises 1 aperture.

In some embodiments a cell-free assay device comprises a lipid bilayer, 3 electrolyte volumes and 2 apertures. In some embodiments a cell-free assay device comprises a lipid bilayer, 3 electrolyte volumes and 1 aperture. In some embodiments a cell-free assay device comprises a lipid bilayer, 3 electrolyte volumes and a channel. In some embodiment a cell-free assay device comprises a lipid bilayer, 2 electrolyte volumes and an aperture. In some embodiment a cell-free assay device comprises a lipid bilayer, 2 electrolyte volumes and a channel. In some embodiment a cell-free assay device comprises a lipid bilayer and 2 electrolyte volumes.

In some embodiments, an electrolyte volume comprises one or more electrodes and/or probes (e.g., electrodes or fiber optic probes). Non limiting examples of probes include an AMGNM, a fiber optic probe, electrode, impedance sensor, or other sensor element. For example, a cell-free assay device can comprise 3 electrolyte volumes and three probes where each electrolyte volume comprises one probe. In another example the device can comprise 2 electrolyte volumes and two probes. In another example the device can comprise 2 electrolyte volumes and 3 probes. An electrolyte volume can comprise any suitable amount of electrodes and/or probes (e.g., electrodes or fiber optic probes) necessary to measure or detect a change (e.g., an electrical change and/or a fluorescent change). An electrode can be made of any suitable material. For example an electrode can comprise Ag/AgCl, platinum (Pt), gold (Au), Carbon, glassy carbon, metal, and the like.

Assay Molecule

In some embodiments a cell-free assay device is configured to detect the presence, absence and/or amount of an assay molecule (e.g., a protein (e.g., a toxin)). In some embodiments a cell-free assay device is configured to characterize one or more activities of an assay molecule (e.g., an interaction of an assay molecule, or portion thereof with a lipid bilayer, e.g., a pore forming activity, an enzyme activity) and/or the potency of an assay molecule. In some embodiments a cell-free assay device is configured to characterize one or more activities and/or the potency of an effector molecule (e.g., an inhibitor, a neutralizing therapeutic agent) of a protein or toxin. An assay molecule can be any suitable protein, toxin, or portion thereof. In some embodiments an assay molecule is any suitable pore forming protein (e.g., a toxin, a pore forming toxin), a portion thereof and/or an effector thereof (e.g., an inhibitor, a potential inhibitor). Non-limiting examples of pore forming proteins and pore forming toxins (PFTs) include alpha-pore-forming toxins (e.g., cytolysin A), beta-pore-forming toxins (α-Hemolysin, gamma-hemolysin, leukocidin, PVL—Panton-Valentine leukocidin), binary toxins (e.g., botulinum toxin (e.g., from *Clostridium botulinum, C. butyricum, C. baratii* and *C. argentinense*) including all serotypes thereof, anthrax toxin, *C. perfringens* Iota toxin and *C. difficile* cyto-lethal toxins), cholesterol dependent toxins (CDCs), PTFs of the membrane attack complex (MAC)PF subclass), small pore-forming toxins (e.g., Gramicidin A), the like, all serotypes thereof and/or combinations thereof. In some embodiments an assay molecule comprises a Clostridial toxin, non-limiting examples of which include BoNT/A, BoNT/B, BoNT/C1, BoNT/D, BoNT/E, BoNT/F, BoNT/G and TeNT. Non-limiting examples of CDCs include Pyolysin (e.g., from *Arcanobacterium pyogenes*), Anthrolysin O (e.g., from *Bacillus anthracis*), Cereolysin (e.g., from *Bacillus cereus*), Sphaericolysin (e.g., from *Bacillus sphaericus*), Thuringiolysin (e.g., from *Bacillus thuringiensis*), Laterosporolysin (e.g., from *Brevibacillus laterosporus*), Bifermentolysin (e.g., from *Clostridium bifermentans*), Botulinolysin, (e.g., from *Clostridium botulinum*), Chauveolysin (e.g., from *Clostridium chauvoei*), Histolyticolysin O (e.g., from *Clostridium histolyticum*), Novyilysin (e.g., frin *Clostridium novyi* A (oedematiens), Perfringolysin O (e.g., from *Clostridium perfringens*), Septicolysin O (e.g., from *Clostridium septicum*), Sordellilysin (e.g., from *Clostridium sordellii*), Tetanolysin (e.g., from *Clostridium tetani*), Vaginolysin (e.g., from *Gardnerella vaginalis*), Ivanolysin (e.g., from *Listeria ivanovii*), Listeriolysin O (e.g., from *Listeria monocytogenes*), Seeligeriolysin O (e.g., from *Listeria seeligeri*), Alveolysin (e.g., from *Paenibacillus alvei*), Streptolysin O (e.g., from *Streptococcus canis, Streptococcus pyogenes, Streptococcus dysgalactiae* or (ssp. *equisimilis*)), Intermedilysin (e.g., from Streptococcus intermedius), Pneumolysin (e.g., from *Streptococcus pneumonia*), Suilysin (e.g., from *Streptococcus suis*)), the like, and combinations thereof. Non-limiting examples of PTFs in the MACPF subclass include C9-like proteins (e.g., C6, C7, C8α, C8β, C9), perforin-like (e.g., perforin), sea anemone toxins (e.g., PsTX-60A, PsTX-60B, AvTX-60A), apextrin, astrotactin-1, astrotactin-2, DBCCR1 (BRINP1), DBCCR1-like protein 1 (BRINP3), DBCCR1-like protein 2 (BRINP2), EPCS50, SpoC1-C1C, malarial related proteins (e.g., SPECT2 and MAOP), macrophage proliferation-specific gene-1 (e.g., MPS and MPG), *Arabidopsis thaliana* CAD1, torso-like protein (Tsl) from *Drosophila melanogaster*, hypothetical protein from the bacteria, *Photorhabdus luminescens* (Plu-MACPF), the like, or combinations thereof.

An assay molecule sometimes comprises a full length, or all of a portion of a protein (e.g., a toxin), polypeptide or peptide. An assay molecule sometimes is a native protein, polypeptide or peptide, or in some embodiments, is a modified protein, polypeptide or peptide (described herein). An assay molecule sometimes is a sub-region of a protein, polypeptide or peptide, such as in the N-terminus, C-terminus, extracellular region, intracellular region, transmembrane region, active site (e.g., nucleotide binding region or a substrate binding region), a domain (e.g., an SH2 or SH3 domain) or a post-translational modified region (e.g., phosphorylated, glycosylated or ubiquinated region), for example. A sub-region often is functional, and an activity of a functional sub-region can be assessed using a device described herein. An assay molecule sometimes comprises a suitable modification of an assay molecule or portion thereof. Non-limiting examples of a modification include a phosphorylation, acetylation, pegylation, glycosylation, glycation, carboxylation, alkylation, amidation, glutamylation, polyglutamylation, ubiquitination, myristolation, malonation, ADP-ribosylation, S-glutathionylation, citrullination, succinylation, nitrosylation, SUMOylation, Neddylation, carbamylation, S-nitrosylation, pupylation, hydroxylation, proteolytic cleavage, iodination, the like, or a combination thereof. In some embodiments an assay molecule comprises protein and/or cleavage products thereof. For example, an assay molecule may be proteolytically cleaved into two or more portions wherein each cleaved portion (e.g., cleavage products) individually or collectively comprises an assay molecule. For example, in some embodiments an assay molecule is one or more cleavage products of a botulinum toxin. In some embodiments an assay molecule is a protein complex comprising two or more proteins and/or subunits.

Target Molecules

In some embodiments a cell-free assay device comprises a target molecule. A target molecule can be a nucleic acid, protein (e.g., a polypeptide, a peptide), carbohydrate, a lipid or a portion thereof. In some embodiments a target molecule comprises a detectable label, non-limiting examples of which include a radiolabel (e.g., an isotope), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody, an antigen or part thereof, a linker, a member of a binding pair), an enzyme substrate, a small molecule (e.g., biotin, avidin), a mass tag, quantum dots, nanoparticles, the like or combinations thereof. In some embodiments a target molecule is a suitable enzyme target, non-limiting examples of which include an enzyme substrate, a protease substrate (e.g., a peptide comprising a protease recognition site, e.g., a protease cleavage site), a FRET (fluorescence resonance energy transfer) substrate, a substrate of an oxidoreductase, a substrate of a transferase (e.g., a phosphorylase), a substrate of a hydrolase (e.g., a phosphatase), a substrate of a lyase, a substrate of an isomerase, a substrate of a ligase, the like, a portion thereof or a combination thereof.

In some embodiments a target molecule is an enzymatic target (e.g., an enzyme substrate). In some embodiments a target molecule comprises an enzymatic target (e.g., an enzyme substrate, an endopeptidase recognition sequence). For example a target molecule, or a portion thereof can be an enzyme substrate. The term "enzymatic target" as used herein refers to a molecule (e.g., a protein or portion thereof) that specifically binds to the active site of an enzyme and often is modified by the enzyme. An enzymatic target can be a suitable polypeptide or protein that can be cleaved by an assay molecule, or portion thereof (e.g., a proteinase (e.g. an endopeptidase)). In some embodiments a target molecule comprises a proteinase cleavage site and/or protease recognition sequence of an assay molecule or portion thereof. In some embodiments the enzymatic target is a proteinase substrate. Proteinase substrates are well known in the art. A proteinase substrate can be a suitable small peptide or linear string of covalently bound amino acids, modified amino acids, amino acid analogs or a combination thereof, that are configured to assay for an enzymatic activity of a proteinase. In some embodiments a target molecule is a protease substrate and/or a protease target of a botulinum toxin (e.g., from *Clostridium botulinum, C. butyricum, C. baratii* and *C. argentinense*) or a portion thereof. In some embodiments a target molecule is a protease substrate (e.g., a synthetic polypeptide or FRET substrate) and/or a protease target (e.g., a natural, native or endogenous target) of a proteolytic product of a botulinum toxin. In some embodiments a target molecule is purified from a suitable source (e.g., a cell). In some embodiments a target molecule is produced my recombinant methods. Sometimes a target molecule is chemically generated (e.g., by protein synthesis methods).

In some embodiments a target molecule comprises a target of a clostridial toxin, or portion thereof. Non-limiting examples of targets of a clostridial toxin include VAMP, SNAP-25, syntaxin or portions thereof. In nature, VAMP is bound to the synaptic vesicle membrane, whereas SNAP-25 and syntaxin are bound to the target membrane. BoNT/A and BoNT/E cleave SNAP-25 in the carboxy-terminal region, releasing modified target molecules of nine or twenty-six amino acid residues, respectively. In some embodiments BoNT/C1 cleaves SNAP-25 near the carboxy-terminus. The botulinum serotypes BoNT/B, BoNT/D, BoNT/F and BoNT/G, and tetanus toxin, often cleave VAMP at a conserved central portion of VAMP, sometimes resulting in the release of an amino-terminal portion of VAMP into the cytosol. In some embodiments BoNT/C cleaves syntaxin at a single site near the cytosolic membrane surface. Thus, the action of BoNT/B, BoNT/C, BoNT/D, BoNT/F, BoNT/G and TeNT sometimes results in release of a large portion of the cytosolic domain of VAMP and syntaxin, while sometimes only a small portion of SNAP-25 is released by proteolysis of BoNT/A, BoNT/C or BoNT/E. In some embodiments a target molecule comprises a SNARE protein, VAMP, SNAP-25, syntaxin, a modified version thereof or a portion thereof.

In some embodiments, a target molecule comprises a FRET (Fluorescence resonance energy transfer) substrate. FRET substrates can be enzymatic targets and are well known in the art. In some embodiments a FRET substrate comprises a clostridial toxin recognition sequence that includes a clostridial toxin cleavage site.

In some embodiments a cell-free assay device comprises a modified target molecule. In some embodiments a modified target molecule is a target molecule that is modified (e.g., modified by an enzyme). In certain embodiments, a target molecule is modified by an assay molecule or a portion thereof resulting in modified target molecule. In some embodiments a modified target molecule comprises an enzyme modification non-limiting examples of which include a phosphorylation, acetylation, pegylation, glycosylation, glycation, carboxylation, alkylation, amidation, glutamylation, polyglutamylation, ubiquitination, myristolation, malonation, ADP-ribosylation, S-glutathionylation, citrullination, succinylation, nitrosylation, SUMOylation, Neddylation, carbamylation, S-nitrosylation, pupylation, hydroxylation, proteolytic cleavage, iodination, the like, or a combination thereof.

A modified target molecule can be a cleavage product. In certain embodiments a target molecule is modified by a proteolytic cleavage and the modified target molecule comprises one or more proteolytic products of the proteolytic cleavage. A modified target molecule can be a target molecule that has been cleaved by a toxin, endopeptidase, proteinase, or a portion thereof. A modified target molecule can be a target molecule that has a toxin or a portion of a toxin bound to the target molecule.

In some embodiments a modified target molecule comprises a detectable label, non-limiting examples of which include a radiolabel (e.g., an isotope), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody, an antigen or part thereof, a linker, a member of a binding pair), an enzyme substrate, a small molecule (e.g., biotin, avidin), a mass tag, quantum dots, nanoparticles, the like or combinations thereof. In certain embodiments a target molecule is cleaved resulting in two or more modified target molecules where only one of the modified target molecules comprises a detectable label.

FRET is a distance-dependent interaction between the electronic excited states of two molecules in which excitation is transferred from a donor fluorophore to an acceptor when the donor and acceptor are in close proximity. Sometimes when the donor and acceptor are in close proximity, the emission of detectable photon from the donor is completely or partially quenched. The process of energy transfer results in a reduction (quenching) of fluorescence intensity and excited state lifetime of the donor fluorophore and, where the acceptor is a fluorophore, can produce an increase in the emission intensity of the acceptor. Upon cleavage of a FRET substrate (e.g., an enzymatic target comprising a quenched fluorophore), resonance energy transfer is reduced and can be detected, for example, by increased donor fluorescence emission, decreased acceptor fluorescence emission, or by a shift in the emission maxima from near the acceptor emission maxima to near the donor emission maxima. In some embodiments, the characteristic or parameters of a proteinase activity are determined by detecting a change in fluorescence emission or emission ratios. In some embodiments, the amount or activity of a proteinase (e.g. clostridial toxin) in a sample can be calculated as a function of the difference in the degree of FRET when using a FRET substrate. In some embodiments the appropriate FRET standards and controls are used.

A variety of donor fluorophores and acceptors, including fluorescent and non-fluorescent acceptors, are known and can be used with FRET based enzymatic targets. Non limiting examples of donor fluorophores include fluorescein, Alexa Fluor® 488, DABCYL, and BODIPY. Non limiting examples of acceptors include tetramethylrhodamine, EDANS and QSY® 7.

As used herein, the term "donor fluorophore" means a molecule that, when irradiated with light of a certain wavelength, emits light, also denoted fluorescence, of a different wavelength. The term fluorophore is synonymous in the art with the term "fluorochrome." The term "acceptor," as used herein, refers to a molecule that can absorb energy from, and upon excitation of, a donor fluorophore.

Binding Agents

In some embodiments a cell-free assay device comprises one or more binding agents. A "binding agent" is sometimes referred to herein as an "analyte binding molecule". In some embodiments a binding agent is configured to bind specifically to an assay molecule, a portion of an assay molecule, an analyte, a target molecule, a portion of a target molecule, or a modified target molecule. In some embodiments a binding agent is configured to bind specifically to an analyte. In some embodiments a binding agent specifically binds to an assay molecule, or portion thereof, an analyte, a target molecule, or portion thereof, or a modified target molecule. In some embodiments a binding agent comprises a member of a binding pair. Non-limiting examples of a binding pair includes antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, receptor/ligand or binding portion thereof, and vitamin B12/intrinsic factor. Non-limiting examples of a binding pair member include an antibody, antibody fragment, reduced antibody, chemically modified antibody, antibody receptor, hapten, anti-hapten, protein, cleaved protein, polypeptide, peptide, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, an ubiquitin moiety, lectin, aptamer, receptor, ligand, metal ion, and the like, and a binding pair may be any combination of the foregoing. A binding pair member may be part of, or all of, one of the following non-limiting examples: a pathogen (e.g., bacterium (e.g., anthrax), virus), biomarker, chemical contaminant, organic contaminant, drug (e.g., elicit drug (e.g., cocaine)), toxin (e.g., anthrax toxin, ricin), chemical compound or combination thereof. Non-limiting examples of binding pairs include antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA), and chemical reactive group/complementary chemical reactive group (e.g., sulfhydryl/maleimide, sulfhydryl/haloacetyl derivative, amine/isotriocyanate, amine/succinimidyl ester, and amine/sulfonyl halides).

A binding agent sometimes comprises an antibody or an antibody fragment. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of an antibodies. In some embodiments a binding agent comprises antibodies or portions thereof, chimeric antibodies, Fab, Fab', F(ab')2, Fv fragments, scFvs, diabodies, aptamers, synbodies, camelids, biotin, tetraethylene glycol, avidin, streptavidin, Neutravidin, the like and/or combinations thereof. Polyclonal and monoclonal antibodies that bind specific antigens are commercially available, and methods for generating such antibodies are known. In general, polyclonal antibodies are produced by injecting an isolated antigen into a suitable animal (e.g., a goat or rabbit); collecting blood and/or other tissues from the animal comprising antibodies specific for the antigen and purifying the antibody. Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen (e.g., Kohler & Milstein, Nature 256:495 497 (1975) and StGroth & Scheidegger, J Immunol Methods 5:1 21 (1980)). Examples of monoclonal antibodies are anti MDM 2 antibodies, anti-p53 antibodies (pAB421, DO 1, and an antibody that binds phosphoryl-ser15), anti-dsDNA antibodies and anti-BrdU antibodies, are described hereafter.

In some embodiments a binding agent comprises a chimeric antibody, humanized antibody, human antibody, or a portion or fragment thereof. Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain. Given that the variable region of an antibody is formed from six complementarity-determining regions (CDRs) in the heavy and light chain variable regions, one or more CDRs from one antibody can be substituted (i.e., grafted) with a CDR of another antibody to generate chimeric antibodies. Also, humanized antibodies are generated by introducing amino acid substitutions that render the resulting antibody less immunogenic when administered to humans.

An antibody fragment utilized as a binding agent sometimes is a Fab, Fab', F(ab')2, Dab, Fv or single-chain Fv (ScFv) fragment, and methods for generating antibody fragments are known (see, e.g., U.S. Pat. Nos. 6,099,842 and 5,990,296). In some embodiments, a binding agent comprises a single-chain antibody fragment, which can be constructed by joining a heavy chain variable region with a light chain variable region by a polypeptide linker (e.g., the linker is attached at the C-terminus or N-terminus of each chain) using recombinant molecular biology processes. Such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342,221). Antibody fragments often comprise engineered regions such as CDR-grafted or humanized fragments. In certain embodiments the binding partner is an intact immunoglobulin, and in other embodiments the binding partner is a Fab monomer or a Fab dimer. For fragments or antibodies comprising a portion or all of a Fc region, a sensing region in a device may include one or more linkers linked to an amino acid or other portion of the Fc region.

In certain embodiments a binding agent is immobilized within a cell-free assay device (e.g., immobilized within an aperture, a channel or a portion thereof). In certain embodiments a binding agent is immobilized on a substrate. The term "immobilized" can mean covalently attached or non-covalently attached (e.g., by hydrogen bonds, ionic bonds, van der Waals forces, and/or hydrophobic interactions). In some embodiments a target molecule and/or a modified target molecule is immobilized by a binding agent. In some embodiments a binding agent comprises a linker. In some embodiments a target molecule, modified target molecule and/or a binding agent is immobilized and/or attached to a cell-free assay device (e.g., immobilized within an aperture, on a channel or a portion thereof) indirectly by an immobilized linker. A binding agent can comprise a linker and a member of a binding pair (e.g. a capture agent). In some embodiments, a substrate can comprise a linker and/or a member of a binding pair (e.g. a capture agent). In some embodiments, a binding agent comprises one member of a binding pair and a substrate comprises the other member of a binding pair. In some embodiments a binding agent is attached to a substrate by a non-covalent interaction of a binding pair. In some embodiments, a binding agent comprises biotin and a substrate comprises avidin.

Binding agents, effectively linked to at least a portion of a cell-free assay device, sometimes are homogeneous or heterogeneous. Where the binding agents are heterogeneous, two or more different types of binding agents may be effectively linked to a particular zone (e.g., 2, 3, 4, 5, 6, 7, 8, 9, 10 or more binding agents may be effectively linked to a particular zone). Different binding agents may be linked to a zone by the same types of linkers or different types of linkers.

In certain embodiments, binding agent can comprise a secondary detectable label (e.g., a reporter molecule) that can be measured. In certain embodiments, a secondary detectable label is a fluorophore. For example, a modified target molecule may comprise a fluorophore that can be detected once bound to a binding agent in addition to or in place of a measurement of a current rectification measurement. In certain embodiments a binding agent and/or a modified target molecule comprises a fluorophore or a combination of fluorophores (e.g., a FRET pair of fluorophores). In certain embodiments, a modified target molecule binds to a binding agent and a second detecting molecule comprising a fluorophore or combination of fluorophores then binds to the bound modified target molecule.

A binding agent often specifically binds to a modified target molecule. The term "specifically binds" refers to a binding agent binding to a modified target molecule in preference to binding other molecules in a particular assay in which a device described herein is utilized. A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more. A modified target molecule often binds to a binding agent by reversible binding (e.g., non-covalent binding), and sometimes by non-reversible binding (e.g., covalent binding).

Linkers

A linker can provide a mechanism for covalently attaching a binding agent (e.g. an antibody or enzymatic target) to a solid support (e.g. a substrate). A "linker" is sometimes referred to as a "tether". Silanes can be used as a linker in some embodiments, however any suitable chemical linker can be used in a device described herein. Non-limiting examples of suitable linkers include: silanes, thiols, polyethylene glycol (PEG) or any other linear or branch chain chemical compound whose length can be chemically controlled and whose ends covalently bond to the binding agent on one end and the synthetic support (e.g. an aperture substrate or structure) on the other. In certain embodiments involving cell-free assay devices fabricated from glass, silane is chosen as the linker molecule.

Methods of attaching a chemical linker to a binding agent (e.g. an antibody or enzymatic target) can be referred to as "crosslinking," and can occur between a reactive group at the end of a linker and a complementary reactive group on the binding molecule and/or solid support (e.g. an aperture substrate or structure, e.g., a channel). Methods of crosslinking are well known in the art. Non-limiting examples of crosslinking include an amine reacting with a N-Hydroxysuccinimide (NHS) ester, an imidoester, a pentafluorophenyl (PFP) ester, a hydroxymethyl phosphine, an oxiran or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

In some embodiments the effective linkage or attachment of a binding agent to a solid support surface (e.g., a substrate) occurs via a chemical attachment, in certain embodiments. Binding agents sometimes are directly attached to the channel of the solid support without intermediate molecules. Binding agents often are effectively or indirectly attached to the channel of the solid support via one or more intermediate molecules. The intermediate molecules sometimes are referred to herein as "linkers" or "modifying molecules." A modifying molecule can effectively link a binding agent to a solid support channel surface in some embodiments. In certain embodiments, a modifying molecule can coat a surface (e.g., surface of the device not in the channel and/or zone in the channel not linked to linkers or binding agents) and effectively block the linkage of binding agents ("blocking molecule"). Linkage between a linker and binding agents and/or solid support channel surface, and/or linkage between modifying molecules and solid support surface, sometimes is non-covalent, and often is covalent. In certain embodiments a "covalent crosslinker" or "crosslinker", is used to attach the binding agent to the modifying molecules.

Any suitable modifying molecule, linker, biological and/or chemical attachment can be utilized. A modifying molecule or linker sometimes is a linear or branch chain chemical compound having a length that can be chemically controlled and having ends that can link to the binding agent on one end and the channel of the solid support on the other (e.g., covalently link). A modifying molecule or linker may be of any suitable length, allowing for the option of altering an aperture radius to approximately match that of a target molecule, in certain embodiments. A modifying molecule and linker generally comprise at least one chemically reactive moiety that permits linkage of the molecule to a surface of the device (e.g., at least a portion of the wall of a channel). A linker often includes at least two chemically reactive moieties, one that permits linkage of the linker to a surface of the device (e.g., zone on the inner wall of a channel) and another that permits linkage of the linker to a binding agent. The chemically reactive moieties on a linker may be the same or different, and different reactive moieties may react with the same or different chemistry. The chemically reactive moieties generally are capable of effecting chemical attachments, which attachments may be covalent or non-covalent. Non-limiting examples of chemical attachments suitable for use for effectively connecting a binding agent to a solid support include: silanes, thiols, phosphonic acid, polyethylene glycol (PEG), the like and combinations thereof. Non-limiting examples of biological attachments suitable for use for effectively connecting a binding agent to a solid support include: biotin, avidin, DNA, the like and combinations thereof. In certain embodiments involving a substrate comprising glass, silane is sometimes chosen as a linker molecule. In certain embodiments involving coating comprising Au, thiols are often chosen as a linker.

Pressure

In certain embodiments, a cell-free assay device comprises a pressure system (e.g., a pressure control system), or an apparatus comprising a pressure system, configured to apply a negative, positive, or neutral pressure across an aperture and/or channel. In certain embodiments, a cell-free assay device comprises a pressure system (e.g., a pressure control system) or an apparatus comprising a pressure system configured to induce a pressure differential across an aperture, a channel and/or between at least two electrolyte volumes. In certain embodiments, a pressure system (e.g., a pressure control system) or an apparatus comprising a pressure system is configured to induce a pressure differential between a first electrolyte volume and a second electrolyte volume, or between a second electrolyte volume and a third electrolyte volume. In certain embodiments, an apparatus comprising a pressure system does not comprise a third electrolyte volume. A "pressure differential" as used herein means a difference in pressure. In some embodiments a component of a device described herein is configured to apply or maintain a pressure differential across an aperture and/or a across a channel of a device described herein.

In some embodiments a cell-free assay device or an apparatus comprising a pressure system comprises a substrate comprising a channel and a binding agent in association with the substrate. A binding agent can be directly or indirectly attached to a substrate. A binding agent can be covalently or non-covalently attached to a substrate. In some embodiments a binding agent is attached to a substrate by a linker. A binding agent can be covalently or non-covalently attached to a linker. A linker can be covalently or non-covalently attached to a substrate.

In some embodiments a cell-free assay device or an apparatus comprising a pressure system comprises a component configured to detect an interaction between an analyte and a binding agent. An "analyte" is sometimes referred to herein as an "assay molecule". In some embodiments an analyte is a target molecule. In some embodiments an analyte is a modified target molecule. In some embodiments an analyte comprises a detectable label. Sometimes an analyte is a suitable molecule. Non-limiting examples of an analyte include an antibody, antibody fragment, reduced antibody, chemically modified antibody, antibody receptor, hapten, anti-hapten, protein, cleaved protein, polypeptide, peptide, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, a ubiquitin moiety, lectin, aptamer, receptor, ligand, metal ion, a pathogen, bacterium, anthrax, virus, biomarker, chemical contaminant, organic contaminant, drug, toxin, ricin, chemical compound, or combinations thereof. In some embodiments a binding agent is configured to specifically bind to an analyte. In some embodiments a cell-free assay device or an apparatus comprising a pressure system comprises a component configured to apply or maintain a pressure differential across the channel in the device.

An apparatus comprising a pressure system may comprise components that are the same, similar to, or different than those called out for a cell-free assay device. In certain embodiments, an apparatus comprising a pressure system does not comprise a lipid bilayer. In some embodiments an apparatus comprising a pressure system comprises a first electrolyte volume and a second electrolyte volume, and an aperture and/or a channel that separates the first electrolyte volume and the second electrolyte volume. In some embodiments the second electrolyte volume comprises a binding agent, often immobilized (e.g., attached) to a substrate.

In some embodiments an apparatus comprising a pressure system comprises a component configured to detect a change in current, impedance, resistance, or electrical potential difference. Often a change in current, impedance, resistance, or electrical potential difference is a result of an analyte translocating across an aperture or a channel. In some embodiments a change is a result of an analyte binding to an immobilized binding agent, often after translocating across an aperture and/or a channel. In some embodiments a component configured to detect a change is configured to detect a binding event (e.g., an interaction). In some embodiments a component configured to detect an interaction is configured for a current rectification measurement, ion current rectification measurement, an impedance based measurement, a coulter-counter technique or combination thereof.

In some embodiments an interaction between an analyte and a binding agent is altered by a method described herein. In some embodiments an interaction between an analyte and a binding agent (e.g., a binding event) is altered by inducing a pressure differential across a channel and/or across an aperture of a device described herein. In some embodiments inducing a pressure across a channel and/or across an aperture of a device described herein accelerates the rate of a binding event (e.g., a binding interaction). In some embodiments translocation of an analyte across an aperture and/or a channel followed by an interaction (e.g., a binding event) of an analyte with a binding agent (e.g., an immobilized binding agent) is limited, in part, by a rate of diffusion of an analyte. In certain embodiments, by inducing a pressure differential across a channel and/or across an aperture, the rate of translocation and/or binding of an analyte is accelerated relative to a rate of the same, or a similar translocation and/or binding event, measured without a pressure differential. In some embodiments inducing a pressure differential across the channel comprises applying a positive pressure across the channel. In some embodiments a positive pressure is applied to a first electrolyte volume comprising an analyte. Without being limited to theory, applying a positive pressure to a first electrolyte volume can induce a pressure differential across an aperture and/or a channel resulting in movement of part of a first electrolyte volume (e.g., solvent, electrolytes, solutes and/or analytes) through an aperture and into a second electrolyte volume. In some embodiments inducing a pressure differential across the channel comprises applying a negative pressure across the channel. In some embodiments a negative pressure is applied to a second electrolyte volume comprising a binding agent. Without being limited to theory, applying a negative pressure to a second electrolyte volume can induce a pressure differential across an aperture and/or a channel resulting in movement of part of a first electrolyte volume (e.g., solvent, electrolytes, solutes and/or analytes) through an aperture and into a second electrolyte volume. In some embodiments rates of translocation and/or binding are compared at a constant temperature. In some embodiments a method for altering an interaction between an analyte and a binding agent comprises interacting an analyte with a binding agent in association with a substrate in a system, where the substrate comprises a channel, inducing a pressure differential across the channel and assessing an interaction between the analyte and the binding agent, where inducing a pressure differential alters the interaction relative to the interaction assessed without inducing a pressure differential. In some embodiments a method for enhancing an interaction between an analyte and a binding agent, comprises interacting an analyte with a binding agent attached to a substrate in a system, wherein the substrate comprises a channel and assessing an interaction between the analyte and the binding agent, where a pressure differential across the channel is at a level at which the interaction is enhanced relative to the interaction at a lower pressure differential.

In some embodiments altering an interaction between an analyte and binding agents reduces a limit of detection of the analyte. In some embodiments altering an interaction between an analyte and binding agents reduces a measurement time. In some embodiments altering an interaction between an analyte and a binding agent enables detection of a lower concentration of analyte in the same measurement time as a higher concentration of analyte.

In some embodiments a pressure control system or an apparatus comprising a pressure control system comprises a pressure port. In some embodiments a pressure control system or an apparatus comprising a pressure control system comprises a piston, syringe or a pump. In some embodiment a pump comprises a positive displacement pump. Non-limiting examples of a positive displacement pump include a rotary lobe pump, progressive cavity pump, rotary gear pump, piston pump, diaphragm pump, screw pump, gear pump, hydraulic pump, vane pump, regenerative (peripheral) pump, peristaltic pump, rope pump, flexible impeller pump, velocity pump, the like or combinations thereof. In some embodiments, a pressure control system or an apparatus comprising a pressure control system comprises a non-positive displacement pump. Non-limiting examples of a non-positive displacement pump include a centrifugal pump, an axial flow pump, a gravity pump (e.g. a siphon), the like and combinations thereof. In some embodiments a piston or a syringe (e.g., a syringe plunger) can be moved mechanically or manually (e.g., by a user) to control pressure in a chamber or housing. A difference in pressure can be induced by applying or inducing a negative or positive pressure to an electrolyte volume. In some embodiments a negative pressure is applied to one electrolyte volume and a positive pressure is applied to another electrolyte volume where the electrolyte volumes are separated by an aperture and/or a channel. In some embodiments a pressure refers to a hydrostatic pressure. In certain embodiments, a cell-free assay device further comprises a pressure system that enables a negative, positive, neutral or combinations thereof hydrostatic pressure to be applied across an aperture. In certain embodiments, a pressure system enables pressure (e.g., a positive pressure or a negative pressure) to be applied to a first electrolyte volume, a second electrolyte volume, a third electrolyte volume or combinations thereof.

In certain embodiments, application of pressure across an aperture and/or a channel increases, decreases or alters the flux of an analyte to a binding agent. In certain embodiments, the application of pressure across an aperture increases, decreases or alters the binding kinetics of an analyte binding to a binding agent. In certain embodiments, the application of pressure across an aperture increases, decreases or alters the translocating speed of an analyte to and/or through the aperture. In certain embodiments the application of pressure across an aperture increases, decreases or alters a combination of the flux of an analyte to a binding agent, the binding kinetics of an analyte to a binding agent, and/or the speed of an analyte to and/or through an aperture. In certain embodiments, at least the first electrolyte volume is sealed (e.g. airtight) such that a pressure differential between at least two volumes can be produced. In certain embodiments, a negative, positive or neutral hydrostatic pressure is applied in the first electrolyte volume, resulting in a pressure differential between the first, second and/or third electrolyte volumes. In certain embodiments, at least the second electrolyte volume is sealed (e.g. airtight) such that a pressure differential between at least two volumes can be produced. In certain embodiments, a negative, positive or neutral hydrostatic pressure is applied in the second electrolyte volume, resulting in a pressure differential between the first, second and/or third volumes. In certain embodiments, at least the third electrolyte volume is sealed (e.g. airtight) such that a pressure differential between at least two volumes can be produced. In certain embodiments, a negative, positive or neutral hydrostatic pressure is applied in the third electrolyte volume, resulting in a pressure differential between the first, second and/or third volumes.

In certain embodiments, an analyte and/or an analyte is allowed to interact with a binding agent. In certain embodiments, the interaction between an analyte and a binding agent is monitored by applying a direct current (DC) bias, alternating current (AC) bias or combinations thereof and measuring the impedance through a channel as a function of the bias. In certain embodiments, the interaction between an analyte and a binding agent is monitored by fluorescence loss or gain, fluorescence polarization, a FRET based measurement, or combination thereof. In certain embodiments, methods of monitoring can include a current rectification measurement, ion current rectification measurement, an impedance based measurement, an impedance based measurement as a function of the applied bias, coulter-counter technique or combinations thereof. In certain embodiments, the methods of monitoring are as a function of time. In certain embodiments, the monitoring is done to confirm the presence of an analyte, to determine the concentration of an analyte, to determine the binding kinetics of an analyte to a binding agent, to determine the potency of an assay molecule, to determine the partial potency of an assay molecule or combinations thereof. In certain embodiments, the concentration of an assay molecule, or a portion thereof, an analyte, and/or a modified target molecule can be determined via a current rectification measurement. A rectification measurement can constitute an averaged measurement looking at a few to many analytes bound to a binding agent at the same time. Ion current rectification, defined as an increase in ion conduction at a given polarity and a decrease in ion conduction for the same voltage magnitude at the opposite polarity, occurs in conical shaped channels due to the voltage dependent solution conductivity within the channel. The level of current rectification is due to the size of the channel, the surface charge, and the Debye length. By coating at least a portion of the channel wall with a binding agent, a certain level of rectification can be measured. As an analyte binds to a binding agents, the current rectification of a channel is altered. The rectification change depends on the overall size and charge of the modified target molecule being bound. The rate of rectification change can be used to determine the concentration of the modified target molecule in solution. The rate of rectification change can be used to determine the potency or partial potency of the assay molecule, or portion thereof, an analyte or combination thereof in solution. In such embodiments a model, or calibration curve, or calibration coefficient, or empirical factor, or combination thereof is generated that directly relates the rate of current rectification change to the concentration of the species being detected.

An interaction between a binding agent and an analyte that results in a bound complex comprising of both a binding agent and an analyte, is sometimes referred to herein as a binding event. In certain embodiments, the rate of a binding event can be altered by changing pressure across an aperture and/or a channel. In some embodiments, the rate of interaction is increased, decreased, unchanged or combinations thereof. In certain embodiments, the rate of interaction is altered to reduce the limit of detection of an analyte (e.g. reduce the lowest concentration of a modified target that can be detected), reduce the time that is takes an analyte to interact with a binding agents, reduce the measurement time, change the binding kinetics of an analyte with a binding agent, increase the time an analyte interacts with a binding agent, reduce the time an analyte interacts with a binding agent, lower the concentration of an analyte that can be detected in the same measurement time as a higher concentration of an analyte, or combinations thereof.

In certain embodiments, the rate of a binding event is increased to reduce the limit of detection of an analyte. In some embodiments, the rate of interaction is increased to reduce the limit of detection of an analyte 1.1 to 100,000,000 fold or more (e.g. 1.1, 1.2, 1.3, 1.4, 1.5, 1.6, 1.7, 1.8, 1.9, 2, 3, 4, 5, 6, 7, 8, 9, 10, 20, 30, 40, 50, 100, 200, 300, 400, 500, 600, 700, 800, 900, 1,000, 2,000, 3,000, 4,000, 5,000, 10,000, 100,000, 1,000,000, 10,000,000, 100,000,000 or more). For example, without the application of pressure, a limit of detection of a modified target can be about 1 picomolar. In some embodiments the addition of 100 mmHg can decrease the limit of detection 2 fold for a resulting limit of detection of 0.5 picomolar.

In certain embodiments, the rate of interaction of an analyte with a binding agent is increased to reduce the measurement time. In certain embodiments, the rate of interaction is increased to reduce the measurement time 1.1 to 100,000,000 fold or more (e.g. 1.1, 1.2, 1.3, 1.4, 1.5, 1.6, 1.7, 1.8, 1.9, 2, 3, 4, 5, 6, 7, 8, 9, 10, 20, 30, 40, 50, 100, 200, 300, 400, 500, 600, 700, 800, 900, 1,000, 2,000, 3,000, 4,000, 5,000, 10,000, 100,000, 1,000,000, 10,000,000, 100, 000,000 or more). For example, in order to obtain a current measurement of a certain concentration of an analyte, a measurement time of 250 minutes is needed. By increasing the pressure from 0 mmHg to 100 mmHg the measurement time is reduced 10 fold, thus resulting in a measurement time of 25 minutes.

In certain embodiments, the rate of interaction of an analyte with a binding agents is increased to enable the detection of a lower concentration of modified target in the same measurement time as a higher concentration of a modified target. In certain embodiments, the rate of interaction is increased to enable the detection of a lower concentration of modified target in the same measurement time as a higher concentration of modified target, wherein the lower concentration of modified target is 1.1 to 100,000, 000 fold or more lower than the higher concentration of modified target (e.g. 1.1, 1.2, 1.3, 1.4, 1.5, 1.6, 1.7, 1.8, 1.9, 2, 3, 4, 5, 6, 7, 8, 9, 10, 20, 30, 40, 50, 100, 200, 300, 400, 500, 600, 700, 800, 900, 1,000, 2,000, 3,000, 4,000, 5,000, 10,000, 100,000, 1,000,000, 10,000,000, 100,000,000 or more.). For example, a 10 micromolar sample is detected in a measurement time of 1 hour. A pressure of 100 mmHg is then applied and a 10 picomolar sample is then detected in the same measurement time of 1 hour. Thus, the rate of interaction is increased through the use of pressure to enable the detection of 10 picomolar modified target, 1,000,000 fold lower concentration, in the same measurement time as the 10 micromolar concentration without pressure.

In certain embodiments, an ideal applied pressure is determined to obtain improvements in the modified target and binding agents interaction. In certain embodiments, a range of pressures are tested to determine the effect of pressure on the limit of detection of a modified target, the measurement time, the rate of the reaction, the amount of time that can be reduced to enable the detection of a lower concentration of modified target in the same measurement time as a higher concentration of modified target, or combinations thereof. In certain embodiments, a pressure with a magnitude of 1 to 2000 mmHg or higher is applied across the channel (e.g. 1, 10, 20, 30, 40, 50, 60, 70, 80, 90, 100, 110, 120, 130, 140, 150, 160, 170, 180, 190, 200, 300, 400, 500, 600, 700, 800, 900, 1000, or 2000 mmHg or higher). In certain embodiments, a pressure with a magnitude of 10 to 500 mmHg is applied across the channel. In certain embodiments, a pressure with a magnitude of 20 to 350 mmHg is applied across the channel. In certain embodiments, a pressure with a magnitude of 30 to 300 mmHg is applied across the channel. In certain embodiments, a pressure with a magnitude of 40 to 250 mmHg is applied across the channel. In certain embodiments, a pressure with a magnitude of 50 to 500 mmHg is applied across the channel.

Detection

In some embodiments a cell-free assay device comprises one or more components configured to detect a change. In some embodiments a cell-free assay device comprises one or more components configured to detect a change in a lipid bilayer. In some embodiments a cell-free assay device comprises one or more components configured to detect an analyte and/or a modified target molecule. In some embodiments a cell-free assay device comprises one or more components configured to detect a binding event (e.g., a binding agent binding to modified target molecule). In some embodiments a component configured to detect a change, a modified target molecule, an analyte and/or a binding event comprises a detector (e.g., a detector assembly). In some embodiments a detector comprises one or more of an electrode and/or a probe. In some embodiments a detector comprises a pair of electrodes.

In some embodiments a component configured to detect a change is configured to detect a change between a first electrolyte volume and a second electrolyte volume. In some embodiments a component configured to detect a change is configured to detect a change between a second electrolyte volume and a third electrolyte volume. In some embodiments a component configured to detect a change in a lipid bilayer comprises a first electrode in a first electrolyte volume and a second electrode in a second electrolyte volume. In some embodiments a component configured to detect a change comprises an electrode in a second electrolyte volume and another electrode in a third electrolyte volume. In some embodiments a component configured to detect a change in a lipid bilayer comprises a first electrode 20 in a first electrolyte volume and a second electrode 22 in a second electrolyte volume and another component is configured to detect a change and comprises an electrode in a second electrolyte volume 22 and another electrode 23 in a third electrolyte volume. Sometimes a first component configured to detect a change and a second component configured to detect a change comprise one or more electrodes in common (e.g., electrode 22 in FIG. 1). For example sometimes a first component configured to detect a change and a second component configured to detect a change share a common reference electrode and/or an electrode that acts as a ground.

In some embodiments a component configured to detect a change comprises one or more of a housing 17, a substrate (e.g., 34, 35), an electrode (e.g., 20, 22, 23), a probe 25, an aperture 40, a channel 14, and an electrolyte volume (e.g., 10, 12, 13).

In certain embodiments, a detector comprises a DC measurement system. In some embodiments, a detector comprises an AC measurement system. In certain embodiments a detector comprises an AC/DC measurement system. In some embodiments a detector comprises a fluorometric detection system. In some embodiment a detector comprises a fluorometer, spectrophotometer or spectrofluorometer. In some embodiments a detector comprises a fiber optic probe. In some embodiments a detector comprises a fiber optic detection system (e.g., a fiber optic camera).

In some embodiments a change (e.g., an electrical change) is measured across a lipid bilayer, aperture, channel, and/or a protein (e.g., a protein channel or pore) or toxin (e.g., BoNT HC). In some embodiments a change (e.g., an electrical change, a fluorescence change) is measured between one electrolyte volume and another electrolyte volume. In some embodiments a change is measured within an electrolyte volume. In some embodiments, a change can be an electrical change. An electrical change can be a change in current, resistance, conductance, impedance, electrical potential, voltage, current rectification, ion current rectification or a change in any electrical parameter related, mathematically or functionally, to current, resistance, or voltage. For example, an electrical change can be a change in conductivity of an electrolyte volume. In another example an electrical change can be a change in voltage potential (e.g., across an aperture or across a lipid bilayer). In yet another example, an electrical change can be a change in current traveling through a protein or toxin. In certain embodiments, the electrical change is time dependent and/or time independent. In some embodiments a change can be a change in fluorescence. For example, sometimes a component is configured to detect a change in electromagnetic radiation (e.g., fluorescence) in an electrolyte volume (e.g., a first, second and/or a third electrolyte volume).

In some embodiments a cell-free assay device comprises a component configured to detect the presence, absence and/or amount of an assay molecule, an analyte, target molecule and/or a modified target molecule. In some embodiments a cell-free assay device comprises a component (e.g., a second component) configured to detect an enzyme activity (e.g., a protease activity) of an assay molecule or portion thereof. In some embodiments a component configured to detect the presence, absence and/or amount of an analyte, target molecule and/or a modified target molecule comprises an endopeptidase assay. In some embodiments an endopeptidase assay comprises a target molecule (e.g., a proteinase substrate) and a method of detecting and/or quantifying the presence, absence or amount of a modified target molecule (e.g., a cleaved target molecule). An endopeptidase assay sometimes comprises an assay molecule (e.g., a protease), a portion thereof and/or a modified target molecule. In certain embodiments an endopeptidase assay comprises a binding agent. In some embodiments a component configured to detect a modified target molecule comprises a binding agent that specifically binds to the modified target molecule. In some embodiments a component (e.g., a second component) configured to detect a modified target molecule is configured to detect a binding event (e.g., a binding event between a binding agent and a modified target molecule). In some embodiments a component (e.g., a second component) is configured to detect a binding event (e.g., a binding event between a binding agent and a modified target molecule) in a third electrolyte volume. In certain embodiments an endopeptidase assay comprises a neutralizing therapeutic agent (e.g., an inhibitor).

In certain embodiments, an endopeptidase assay comprises a solid support that comprises a channel. In some embodiments the solid support comprises a first surface, an opposing second surface, and a wall or walls between the first surface and the second surface. In some embodiments the channel comprises a proximal opening at the first surface, a distal opening at the second surface and an interior sidewall surface, wherein the proximal opening of the channel is in contact with the second electrolyte volume and the distal opening is in contact with a third electrolyte volume. In certain embodiments, at least a portion of the channel wall is coated with at least one type of a binding agent that is capable of binding at least one type of modified target molecule. In certain embodiments, an endopeptidase assay is a type of device as described in PCT/US2012/033142, which is hereby incorporated by reference.

In certain embodiments, where the second electrolyte volume comprises a monolayer, a solid support of the endopeptidase assay goes through the monolayer so that the proximal opening of the channel (e.g., the aperture) is in direct contact with the second electrolyte volume.

In some embodiment a second electrolyte volume comprises a target molecule. In some embodiments a target molecule is immobilized to a solid support (e.g., an electrode, an optical fiber, a substrate, a GNM, an AMGNM). A target molecule can be immobilized by a binding agent or by the interaction of a binding pair (e.g. biotin/avidin). In some embodiments a target molecule is immobilized by an antibody or an antibody fragment. In some embodiments, an analyte and/or a target molecule diffuse freely in an electrolyte volume. In some embodiments, an analyte and/or a target molecule is immobilized within an electrolyte volume. In some embodiments, a target molecule that is immobilized in an electrolyte volume is cleaved by an assay molecule or a portion thereof (e.g., an endopeptidase (e.g. a BoNT toxin). In certain embodiments a portion of a target molecule (e.g., a modified target molecule) is released from a solid support (e.g., a substrate, an electrode, an optical fiber, a channel). In some embodiments the released portion of a target molecule (e.g., a modified target molecule) is measured by detecting a change (e.g., an electrical change, a change in electromagnetic radiation) by methods described herein. In some embodiments, the released portion of a target molecule (e.g., a modified target molecule) changes the conductive properties and an electrolyte volume. In some embodiments a target molecule is immobilized in an electrolyte volume and the target molecule is cleaved by a portion of an assay molecule that translocated into the electrolyte volume from another electrolyte volume (e.g., through a lipid bilayer, through a pore in a lipid bilayer). In some embodiments an electrolyte volume comprises a target molecule, the target molecule is cleaved by a portion of an assay molecule resulting in the production of a modified target molecule and the modified target molecule binds to a binding agent. In some embodiments an electrolyte volume comprises a target molecule, the target molecule is cleaved by a portion of an assay molecule resulting in the production of a modified target molecule and the modified target molecule translocates into another electrolyte volume. Sometimes a modified target translocates from one electrolyte volume into another electrolyte volume and the modified target molecule is detected and/or quantified. Sometimes a modified target translocates from first electrolyte volume into a second electrolyte volume, the modified target molecule binds to an immobilized binding agent in the second electrolyte volume, and the binding event is detected and/or quantified. In some embodiments a binding event results in a measurable change (e.g. an electrical change). In some embodiments a bound modified target molecule is detected or quantified by detecting a change (e.g., an electronic or fluorescence change).

In some embodiments a detector is configured to detect a detectable signal. In some embodiments a detector is configured to detect a detectable signal in an electrolyte volume (e.g., a first, a second and/or a third electrolyte volume). In some embodiments a second component is configured to detect a detectable signal in a third electrolyte volume. In some embodiments a detectable signal comprises electromagnetic radiation (e.g., visible light, fluorescent light). In some embodiments a detectable signal comprises an electrical signal (e.g., a change in current, resistance, impedance, electrical potential, current rectification, ion current rectification or a combination thereof). In some embodiments a detectable signal comprises a change (e.g., an electrical change) between a first electrolyte volume and a second electrolyte volume and/or between a second electrolyte volume and a third electrolyte volume. In some embodiments a modified target molecule, or a portion thereof emits a detectable signal. In some embodiments an analyte and/or a modified target molecule comprise a label (e.g., a detectable label, e.g., a fluorescent label) that emits a detectable signal. In some embodiments an analyte, an unmodified target and/or a target molecule does not emit a detectable signal. In some embodiments a component configured to detect a modified target molecule (e.g., a second component configured to detect) is not configured to detect an unmodified target molecule (e.g., a target molecule). In some embodiments, a detector (e.g., a detector configured to detect a detectable signal) can detect fluorescence emitted from a fluorophore. For example, sometimes a target molecule comprises a FRET substrate, the FRET substrate is cleaved by an assay molecule, or a portion thereof, resulting in modified target molecule comprising a detectable fluorescent signal. In some embodiments, a detector as described herein comprises a fluorometer or a spectrophotometer. In certain embodiments, a fluorometer or spectrophotometer comprises a fiber optic cable, lamp, excitation source or a laser. Various light sources can be used as an excitation source, including but not limited to lasers, photodiodes, lamps, xenon arcs and mercury-vapor lamps. In some embodiments, a fluorometer or spectrophotometer can comprise filters and/or monochromators. In some embodiments a detector comprises a photodetector, fiber optic probe, and/or a fiber optic camera. A detector can be single-channeled or multi-channeled. In some embodiments, a detector comprises a light source (e.g., a laser, an excitation light source), a fiber optic cable, one or more filters and/or a photodetector (e.g., a photocell, an imager, a CMOS or CCD imager).

In some embodiments a modified target molecule (e.g. proteolytic cleavage product of an enzymatic target) freely resides within an electrolyte volume in which is was acted upon. In some embodiments this freely diffusing modified target molecule results in a measurable change (e.g. fluorescence change). In some embodiments a free modified target molecule is detected or quantified by detecting a change (e.g., an electronic or fluorescence change).

In certain embodiments, the lipid bilayer and/or endopeptidase assay are contained within a chamber and/or a housing. In certain embodiments, a chamber forms a first electrolyte volume, a second electrolyte volume or a third electrolyte volume or combinations thereof. A chamber can be manufactured from a suitable material. In some embodiments a chamber and/or a housing comprises a substrate. In certain embodiments, a chamber can be Si, SiO2, Si3N4, alumina, nitrides, diamond, quartz, sapphire metals, ceramics, polymers (e.g., Teflon, polycarbonate), PDMS, plastics (e.g. acrylics, polyurethanes, silicones, halocarbons) the like or combinations thereof. In certain embodiments, a chamber and/or a housing comprises inlet ports, outlet ports or both to allow for fluid flow and sample introduction. In some embodiments, a chamber and/or a housing comprises inlet pores, outlet ports or both to allow for application of pressure gradients to the first volume, second volume, or third volume, or combinations thereof. In certain embodiments, a chamber and/or a housing comprises airtight cells for the first volume, second volume or third volume, or combinations thereof, to control atmosphere and/or humidity.

In certain embodiments, a chamber and/or a housing further comprises a pressure system that enables a negative, positive, neutral or combinations thereof pressure to be applied across an aperture and/or a channel. In certain embodiments, a cell-free assay device further comprises a pressure system that enables a negative, positive, neutral or combinations thereof hydrostatic pressure to be applied across an aperture and/or a channel. In certain embodiments, a pressure system enables pressure to be applied to a first electrolyte volume, a second electrolyte volume, a third electrolyte volume or combinations thereof.

Determining Parameters of Target Molecule

In certain embodiments, a cell-free assay device described herein can be used to study one or more kinetic parameters (e.g. binding or enzymatic parameters) associated with an assay molecule, an analyte, a target molecule, a modified target molecule and/or a binding event. Non-limiting examples of kinetic parameters useful for detecting and/or determining the presence, absence, activity or concentration of a target molecule or a modified target molecule include the on rate (Kon), the off rate (Koff), affinity (Kd=Koff/Kon), Km, Vmax, velocity, rate, turn-over rate, substrate concentration, production concentration, enzyme concentration, enzyme-substrate concentration, channel gating frequency, the like and combinations thereof. In some embodiments, any parameters (e.g., pH, trace metal concentrations (e.g. zinc), temperature, pressure, salt concentration, enzymatic target concentration, toxin concentration (i.e. enzyme concentration), and the like, can be altered or adjusted within an electrolyte volume, as necessary to allow detection and or quantification of an assay molecule, a target molecule, a modified target molecule and/or a binding event.

In some embodiments an electrolyte comprises a test substance. In some embodiments an electrolyte comprises a neutralizing therapeutic agent (e.g., an inhibitor). In some embodiments, an electrolyte volume can comprise an inhibitor. In some embodiments, the inhibitor can be a proteinase inhibitor (e.g., an endopeptidase inhibitor). In some embodiments an inhibitor is a BoNT inhibitor. In some embodiments an inhibitor is used to determine an inhibitor constant (e.g., K).

Methods for Using a Cell-Free Assay Device

In some embodiments, provided herein, is a method of using a cell-free assay device to detect, quantitate and/or characterize an assay molecule. In some embodiments a method for assaying an assay molecule, comprises contacting an assay molecule with a first electrolyte volume. In some embodiments an assay molecule is introduced into a first electrolyte volume. Sometimes an assay molecule is introduced into a first electrolyte volume by a port or syringe. In some embodiments the presence, absence or amount of an interaction between an assay molecule and a lipid bilayer (e.g., a lipid bilayer that separates a first and a second electrolyte volume) is detected. In certain embodiments detection of an interaction between an assay molecule and a lipid bilayer comprises detecting (i) insertion of the assay molecule, or a portion thereof, into the bilayer, (ii) translocation of the assay molecule, or a portion thereof, through the bilayer, (iii) binding of the assay molecule, or a portion thereof, to the bilayer, (iv) binding of an assay molecule, or a portion thereof, to at least one receptor on a lipid bilayer (v) association of the assay molecule or a portion thereof with the bilayer, or a combination thereof. In certain embodiments detection of an interaction between an assay molecule and a lipid bilayer comprises detecting a change in the conductance, resistance, current, electrical potential or a combination thereof of the lipid bilayer and or across the lipid bilayer. In some embodiments an interaction comprises formation of a pore in a lipid bilayer wherein the pore comprises all, or a part of an assay molecule. An interaction between an assay molecule and a lipid bilayer can be detected by a component (e.g., a first component) configured to detect a change in a lipid bilayer. In some embodiments, an assay molecule, or a portion thereof, translocates across the lipid bilayer from a first electrolyte volume into a second electrolyte volume. In some embodiments an assay molecule undergoes proteolysis and cleaves itself resulting in two portions of an assay molecule. In some embodiments, an assay molecule, or portion thereof, modifies a target molecule at least in part in the second electrolyte volume to produce a modified target molecule. In some embodiments one portion of an assay molecule comprises a pore forming portion and the other portion comprises an enzyme portion. In certain embodiments an enzyme portion of an assay molecule translocates across a lipid bilayer in a cell-free assay device. Sometimes a method for assaying an assay molecule using a cell-free device comprises detecting the presence, absence or amount of an interaction between the assay molecule, or portion thereof, with a target molecule, or portion thereof, which target molecule is in the second electrolyte volume. Sometimes a portion of an assay molecule that translocates across a lipid bilayer into a second electrolyte volume comprises endopeptidase activity. In some embodiments an interaction between an assay molecule, or a portion thereof, with a target molecule comprises proteolysis (e.g., cleavage) of a target molecule resulting in a modified target molecule. In some embodiments a target molecule is an enzymatic target of an assay molecule that was introduced into the first electrolyte volume.

In some embodiments a component of a cell-free assay device is configured to detect a modified target molecule. In some embodiments a component of a cell-free assay device detects a modified target molecule where the detecting comprises detecting a cleavage product of the target molecule. In certain embodiments a cleavage product is detected in the second electrolyte volume. In certain embodiments a cleavage product is detected in a third electrolyte volume. In some embodiments a cleavage product translocates from a second electrolyte volume to a third electrolyte volume. Sometimes the cleavage product (e.g., modified target molecule) is immobilized on a substrate. Sometimes the cleavage product (e.g., modified target molecule) is immobilized on a substrate in a third electrolyte volume. Sometimes the cleavage product (e.g., modified target molecule) is immobilized on a substrate in a channel comprising a third electrolyte volume.

Figure 2A:
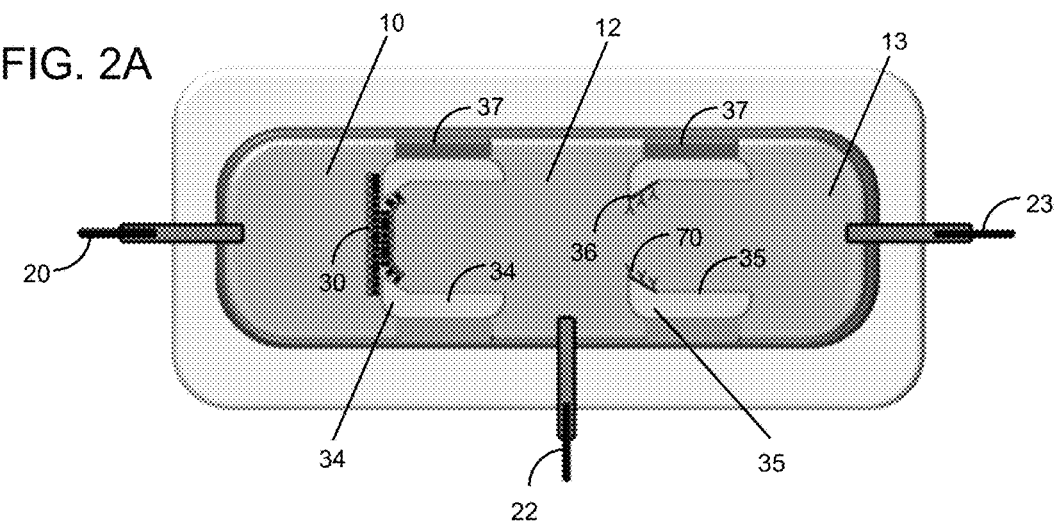
FIGS. 2A-C illustrate an embodiment of a cell-free assay device workflow.
Figure 2B:
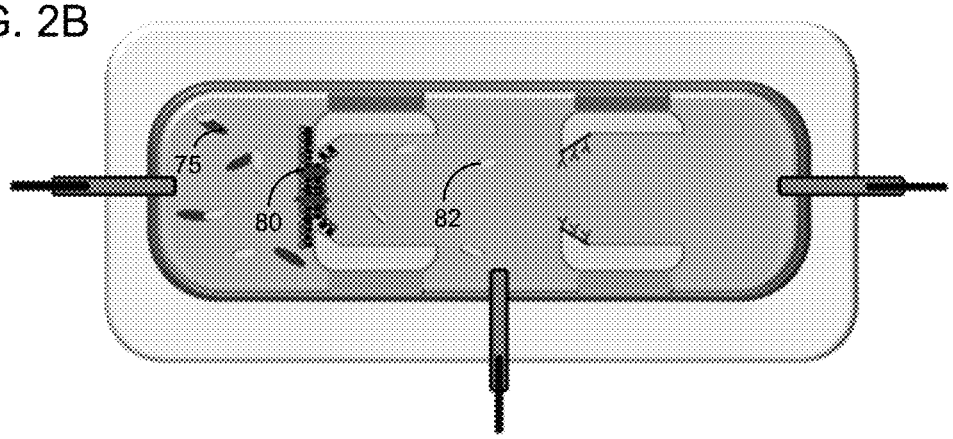
Figure 2C:
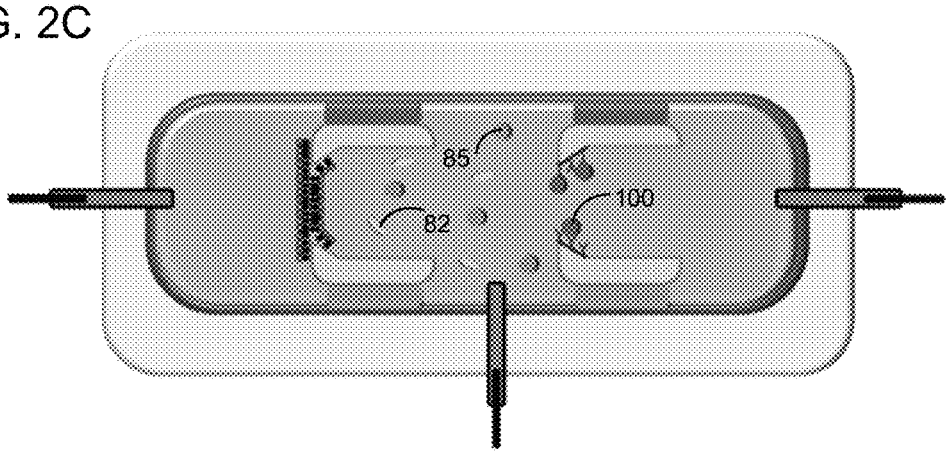
Figure 3A:
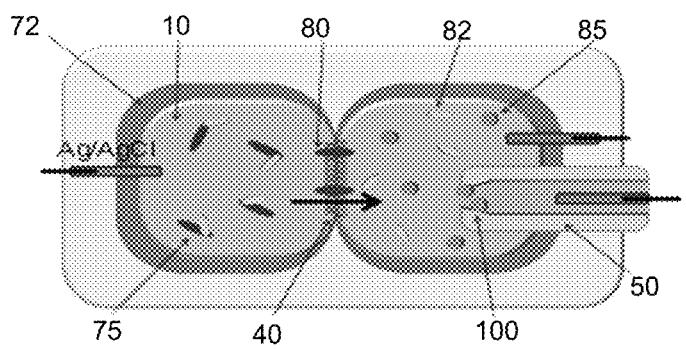
FIGS. 3A-D show a cell-free assay device comprising an encapsulated lipid bilayer (EIB) 30'.
Figure 3B:
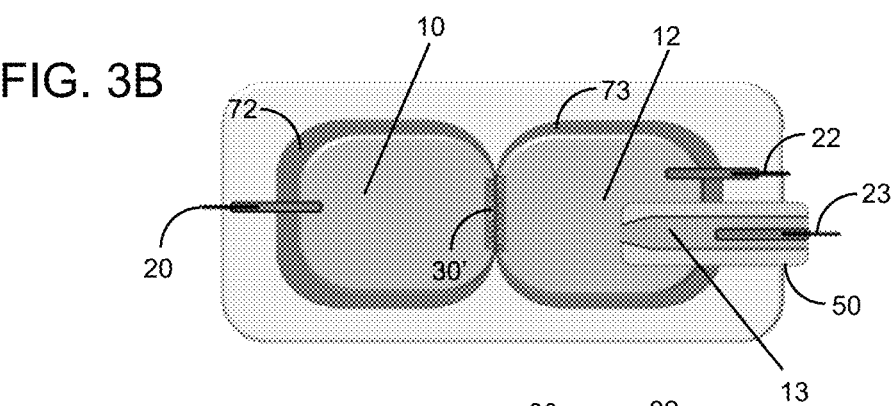
Figure 3C:
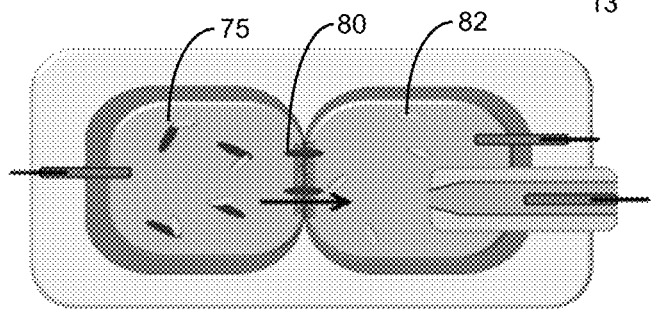
Figure 3D:
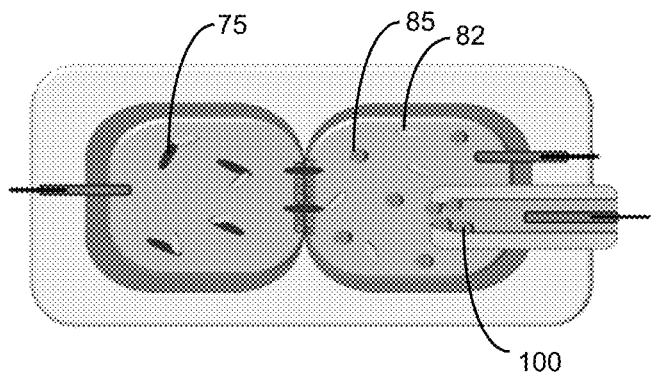

For example, FIG. 2 illustrates an embodiment of a cell-free assay device workflow. FIG. 2A shows a cross-section of a cell-free assay device set up with two apertures separating three different solution chambers (e.g., comprising a first 10, second 12 and third 13 electrolyte volume). A first aperture comprises a first substrate 34 and a second aperture comprises a second substrate 35. FIG. 2B shows an assay molecule (75, e.g., a toxin, e.g. BoNT) introduced into a first electrolyte volume 10. The rate of insertion of a pore forming portion of an assay molecule (80, e.g., heavy chain (HC) of BoNT) and translocation of an enzyme portion of an assay molecule (82, e.g., light chain of BoNT) can be monitored between electrodes 20 and 22. FIG. 2C illustrates cleavage of a target molecule (85, e.g., a SNARE protein) by an enzyme portion of an assay molecule 80 resulting in a modified target molecule 100 (e.g., a cleaved SNARE protein) that binds to an immobilized binding agent 20 (e.g., an antibody). In some embodiments the cleavage event and/or binding event is monitored between electrodes 22 and 23, using a suitable method of measurement (e.g., a rectification measurement, a nanopore rectification measurement).

In some embodiments a second component of a cell-free assay device detects a detectable signal (e.g., an electrical signal, e.g., a change in conductivity, impedance, current, electrical potential, or a combination thereof). Sometimes the detectable signal results from a binding event between a modified target molecule (e.g., a cleavage product) and a binding agent. Sometimes the detectable signal results from the presence and/or amount of a modified target molecule in an aperture that separates a second electrolyte volume from a third electrolyte volume. Sometimes the detectable signal results from the presence and/or amount of a modified target molecule in a channel comprising a third electrolyte volume. In some embodiments a binding agent is bound or attached to a substrate in a channel and/or in a third electrolyte volume.

In some embodiments a second component of a cell-free assay device detects a detectable label and/or a detectable signal of a modified target molecule (e.g., a cleavage product). Sometimes detecting a detectable label or detectable signal comprises detecting emission of electromagnetic radiation from a modified target molecule or from a detectable label attached to a modified target molecule. Sometimes the detectable label is a fluorescent label and/or a FRET label. In some embodiments detecting a cleavage product comprises monitoring a detectable label in association with the cleavage product.

In some embodiments detecting a modified target molecule (e.g., a cleavage product) comprises inducing a pressure differential. In some embodiments of a method described herein, a pressure differential is induced between a second electrolyte volume and a third electrolyte volume. In some embodiments detecting a modified target molecule (e.g., a cleavage product) comprises adjusting the pressure of the second and or third electrolyte volume. Sometimes adjusting the pressure comprises decreasing the pressure in a third electrolyte volume. Sometimes adjusting the pressure comprises increasing the pressure in a third electrolyte volume. Sometimes adjusting the pressure comprises increasing the pressure in a second electrolyte volume. Sometimes adjusting the pressure comprises decreasing the pressure in a second electrolyte volume.

In some embodiments a method of characterizing an assay molecule using a cell-free assay device as described herein comprises determining the potency of the assay molecule, or portion thereof. The term "potency" as used herein means a measure of activity of an assay molecule (e.g., a toxin) expressed in terms of the amount required to produce an effect of a given intensity. In some embodiments the effect of a given intensity is determined, in part, by the amount of a modified protein target that is detected after introduction of a given amount of an assay molecule into a first electrolyte volume. In some embodiments detecting a modified target molecule (e.g., a cleavage product) comprises quantifying an amount of a modified target molecule. In some embodiments determining the potency of an assay molecule (e.g., a toxin) comprises detecting the presence, absence or amount of two or three of (i) insertion of the assay molecule, or portion thereof, into the lipid bilayer (ii) translocation of the assay molecule, or portion thereof, into the second electrolyte volume, and (iii) a modified target molecule (e.g., a cleavage product of the target molecule).

In certain embodiments, a cell-free assay device is used to monitor insertion of an assay molecule, or portion thereof, into a lipid bilayer and/or an enzyme activity of an assay molecule, or a portion thereof. In some embodiments an insertion event and/or an enzyme activity is measured and/or monitored directly and/or indirectly. In some embodiments an assay molecule is introduced into an electrolyte volume (e.g., a first electrolyte volume). In some embodiments an assay molecule is contacted with an electrolyte volume (e.g., a first electrolyte volume). In some embodiments a toxin or pore forming protein (e.g. a BoNT toxin) is introduced into a first electrolyte volume thus allowing integration of a pore forming protein into a lipid bilayer. In some embodiments a heavy chain of a functional BoNT can form a pore or channel in the lipid bilayer. In some embodiments, a pore is formed in a lipid bilayer by interaction of an assay molecule with a lipid bilayer in a cell-free assay device. In some embodiments a pore that is formed in a lipid bilayer allows translocation of an assay molecule, or a portion thereof, through a lipid bilayer. In some embodiments a light chain of a functional BoNT translocates through the heavy chain pore and into a second electrolyte volume. In some embodiments, several parameters of a translocation event can be detected and quantified by a cell-free assay device as described herein, for example by detecting and/or measuring a change (e.g., an electronic change). In certain embodiments, an assay molecule is contacted with a first electrolyte volume and an interaction, insertion or association of the assay molecule with a lipid bilayer is monitored by measuring a change in current, conductance or resistance or a combination thereof. In certain embodiments, additional characteristics of an assay molecule are monitored. Additional characteristics can include measurement of insertions, channel gating frequency, translocations of part or all of an assay molecule, translocation of a modified target or combinations thereof. In certain embodiments, the insertion of the heavy chain (HC) portion of the BoNT toxin is monitored by measuring the change in conductance of the bilayer. In certain embodiments, the conductance associated with the HC insertion is further changed when the light chain of the toxin translocates through the toxin into the second electrolyte volume. In certain embodiments, a whole assay molecule or a portion of an assay molecule moves from a first electrolyte volume into a second electrolyte volume. In certain embodiments, an insertion, association or interaction of an assay molecule with a bilayer can be used to determine at least part of the activity of a protein or toxin. In certain embodiments, the rate of insertion or interaction of an assay molecule with a bilayer can be used to determine a concentration of an assay molecule.

In some embodiments, a second electrolyte volume comprises a proteinase assay (e.g., an endopeptidase assay). In certain embodiments, a portion of the protein or toxin (e.g., the light chain of BoNT) that moves through the lipid bilayer of a first aperture can then interact with an endopeptidase assay. In some embodiments, a second electrolyte volume comprises a target molecule. In some embodiments, a target molecule can be enzymatically cleaved by an assay molecule that translocates from a first electrolyte volume to a second electrolyte volume. The product of this cleavage event can be detected and quantified by detecting a change (e.g., an electronic change, a change in fluorescence).

In some embodiments, a cell-free assay device comprises a channel and/or an aperture in a solid support and/or substrate where the aperture defines and divides a second electrolyte volume from a third electrolyte volume. An aperture, sometimes comprising a channel, wherein the aperture and/or channel comprise a substrate comprising glass, sapphire, or the like, is referred to herein as a glass nanopore membrane (GNM). In some embodiments a GNM comprises an aperture and a channel. In some embodiments a GNM comprises a lipid bilayer. In some embodiments a GNM does not comprise a lipid bilayer. In some embodiments, a GNM comprises a channel coated with a binding agent (e.g., an antibody). A GNM comprising a channel and/or aperture coated with an antibody is sometimes referred to herein as an antibody modified GNM (AMGNM). In some embodiments, a first, second and third electrolyte volumes each comprise an electrode. In some embodiments, a first, second and third electrolyte volumes each comprise one or more electrodes. In some embodiments a first electrolyte volume comprises a first electrode and a second electrolyte volume comprises a second electrode. As described herein, a change can be detected and/or measured between a first and second and/or a second and third electrolyte volumes. In some embodiments, a change (e.g., an electronic change) can be detected and/or measured in and/or across a first aperture and/or a second aperture of a cell-free assay device. In some embodiments, a change detected between a second and third electrolyte volumes provides information about the characteristics of an endopeptidase reaction (e.g., toxin concentrations, endopeptidase concentrations, product concentrations, substrate concentrations, rate of cleavage, or enzyme kinetics). In some embodiments, a fluorescent molecule is detected and/or quantified in the second electrolyte volume that provides information about the characteristics of the endopeptidase reaction (e.g., toxin concentrations, endopeptidase concentrations, product concentrations, substrate concentrations, rate of cleavage or enzyme kinetics).

In certain embodiments, the endopeptidase assay can be an immunoassay (i.e. antigen/antibody complex formation) or endopeptidase measurement (i.e. monitoring the cleavage of a target molecule) and can be monitored by any suitable detection mechanism, including but not limited to a rectification measurement (e.g., a nanopore rectification measurement), an impedance based measurement, coulter counter technique, fluorescence loss or gain, fluorescence polarization, a FRET based measurement, capillary electrophoresis, mass spectrometry, and any other targeted antibody technique.

In some embodiments, a second or third electrolyte volume comprises a target molecule or portion thereof. In some embodiments a target molecule (e.g. SNAP-25) is cleaved by a target molecule or portion thereof (e.g. an endopeptidase). In some embodiments the cleaved target molecule or portion thereof can be captured by a binding agent (e.g., an antibody). In some embodiments, the cleaved enzymatic target or portion thereof is detected or quantified by an immunoassay. In some embodiments the cleaved enzymatic target is detected or quantified by detecting or quantifying a change (e.g. a change between the second and third electrolyte volumes, or a change in the third electrolyte volume).

In some embodiments a cell-free assay device is used to monitor antigen/antibody (modified target/binding agent) complex formation by measuring an ion current rectification. Ion current rectification is sometimes defined as an increase in ion conduction at a given polarity and a decrease in ion conduction for the same voltage magnitude at the opposite polarity. In some embodiments ion current rectification occurs in and/or across a channel (e.g., a conical shaped channel) due to the voltage dependent solution conductivity within the channel. Sometimes the level of current rectification is dependent, in part, to the size of a channel, the surface charge of a channel, and/or the Debye length of a channel. In certain embodiments, for example, a cell-free assay device comprising a channel is coated with an antibody (e.g., by use of silane or phosphate linkers) and a certain level of initial current rectification can be measured (Vlassiouk, I., et al., (2009) Journal of the American Chemical Society 131(23); 8211-8220). Sometimes as an antigen in solution binds to a binding agent (e.g., an antibody) coated on a channel, the current rectification through the channel is altered. In such embodiments, a change in current rectification can be measured. Sometimes the difference in rectification produced upon antigen attachment depends, in part, on the initial level of rectification and the overall size and charge of an antigen.

In some embodiments a method of assaying an assay molecule using a cell-free assay device as described herein comprises determining whether a test substance neutralizes an assay molecule, or portion thereof. In some embodiments determining whether a test substance neutralizes an assay molecule may comprise determining the effectiveness of a test substance at neutralizing the activity of an assay molecule. A test substance can be any suitable molecule or small compound. In some embodiments a test substance is a therapeutic neutralizing agent (e.g., a neutralizing agent of an assay molecule, or potential neutralizing agent of an assay molecule). In some embodiments a test substance is an inhibitor or potential inhibitor of an assay molecule (e.g., a toxin). In certain embodiments determining whether a test substance neutralizes an assay molecule comprises introducing a test substance into the cell-free assay device. In some embodiments determining whether a test substance neutralizes an assay molecule comprises detecting the presence, absence or amount of two or three of (i) insertion of the assay molecule, or portion thereof, into the lipid bilayer (ii) translocation of the assay molecule, or portion thereof, into the second electrolyte volume, and (iii) the cleavage product of the target molecule.

In certain embodiments, the measurement of the protein or toxin interaction with the lipid bilayer and the measurements from the endopeptidase assay can be used to completely characterize a protein or toxin. In certain embodiments, the measurement of the endopeptidase assay can be used to completely characterize a protein or toxin, or neutralizing agent thereof. The cell-free assay device and cell-free assay device method can be used for numerous applications including, but not limited to determining the potency of a toxin comprising sample (i.e. Botox, Botox Cosmetic, Vistabel, Dysport, Reloxin, Xeomin, PurTox, Myobloc, Neurobloc, Neuronox, CBTX-A, and the like), determining the neutralization efficacy of a therapeutic or chemical which neutralizes or partially neutralizes a toxin, in addition to determining where or how a therapeutic or chemical is neutralizing a toxin/protein (i.e., preventing binding, insertion, translocation, or its enzymatic activity), detection and discriminating proteins and/or toxins, and determining the concentration of proteins and/or toxins in a given sample in certain embodiments.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1

Assay Device

An example of BoNT toxin is described, but should not be considered limiting in any way.

As depicted in FIG. 2, initially, BoNT toxin is introduced into the left chamber (first electrolyte volume). The rate of the HC insertions into the lipid bilayer and LC translations through the HCs, is monitored FIG. 2B. In this example, a DC bias is applied to measure the conductance through the HC. Unoccluded HCs, where the LC has translocated through and been released from the HC, can be differentiated from HC/LC complexes based on their respective current signature. After the LC has translocated into the middle chamber (second electrolyte volume), the rate of SNARE protein cleavage is monitored using a channel (e.g., by an endopeptidase assay) that is coated with a binding agent (e.g., an antibody) that specifically binds a cleaved form of the SNARE protein (e.g. the enzymatic target that has been acted upon by the toxin or protein) (FIG. 2C).

In certain embodiments, the cell-free assay device and method is used to determine the potency of a sample of toxin. Using the example of BoNT, measurements can include a combined measurement which consists of the product of the rates of unoccluded HC insertions, LC translocation, and LC SNARE protein cleavage. The acquired data can then be converted into mouse intraperitoneal injection assay equivalents using a calibration curve and/or an empirical factor to determine the potency of a sample, including detection, concentration, and activity for unknown samples. In certain embodiments, the acquired data can be further used to determine the efficacy of a neutralizing therapeutic. In this example, once the rates of these processes have been measured for a given BoNT sample and set of test conditions, the process can be rerun with the anti-BoNT neutralizing therapeutic introduced into the left chamber prior to the BoNT. The difference in rates of unoccluded HC insertion, LC translocation, and SNARE protein cleavage can then be used to determine therapeutic efficacy of the neutralizing agent. The test units associated with the cell-free assay device, which consists of the product of the rates of unoccluded HC insertions and LC SNARE protein cleavage, can then be converted into MLN assay equivalents using a calibration curve and/or an empirical factor. A typical cell-free assay device test will take less than a few hours to complete, significantly reducing the testing time relative to the mouse intraperitoneal injection assay, as well as provide complete infection and neutralization mechanism analysis.

In certain embodiments, the cell-free assay device and method is used to determine the potency of a sample of toxin. Using the example of BoNT, measurements can include just the measurement LC SNARE protein cleavage after it has translocated through the lipid bilayer via the HC. The acquired data can then be converted into mouse intraperitoneal injection assay equivalents using a calibration curve and/or an empirical factor to determine the potency of a sample, including detection, concentration, and activity for unknown samples. In certain embodiments, the acquired data can be further used to determine the efficacy of a neutralizing therapeutic.

The cell-free assay device mimics a cell and allows the complete in vivo mechanism of the botulinum toxin to be monitored. Unlike other assays the cell-free assay device is capable of individually evaluating the neutralization of the HC and LC portions of BoNT on a single, easy-to-use platform that does not require highly controlled laboratory settings. In addition, the proposed cell-free assay device provides a number of desirable features over current methodologies, including:

1. No animals are used.
2. The test does not require a highly controlled laboratory setting or cell lines.
3. The complete toxin mechanism is characterized.
4. The neutralization of the HC and LC portions of BoNT are independently evaluated.
5. Testing times are reduced from days to hours, in comparison to the standard MLN assay.
6. The cell-free assay device is easy-to-use, requires minimal consumable, and can be stored and transported easily.
7. The cell-free assay device is capable of determining not only the efficacy of target sets of BoNT antibodies, but mixtures of antibodies as well.
8. Multi-toxin neutralization can be determined from the cumulative results of individual serotype tests.

Example 2

Device Using an EIB or DIB

The general workflow of the cell-free assay device concept using an EIB and the example of BoNT, is depicted in FIG. 2.

Figure 4A:
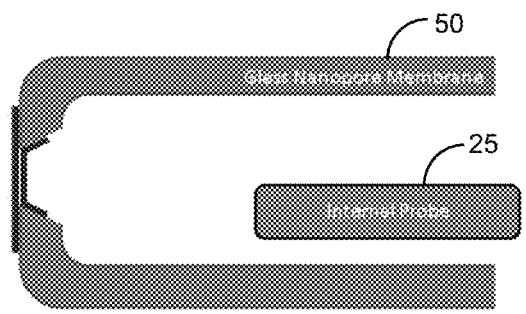
FIGS. 4A-B show a cross-section of a cell-free assay device assay utilizing a glass nanopore membrane (GNM) device comprising a GNM substrate 50 comprising glass (e.g., for holding a planar lipid bilayer (PLB) 30.
Figure 4B:
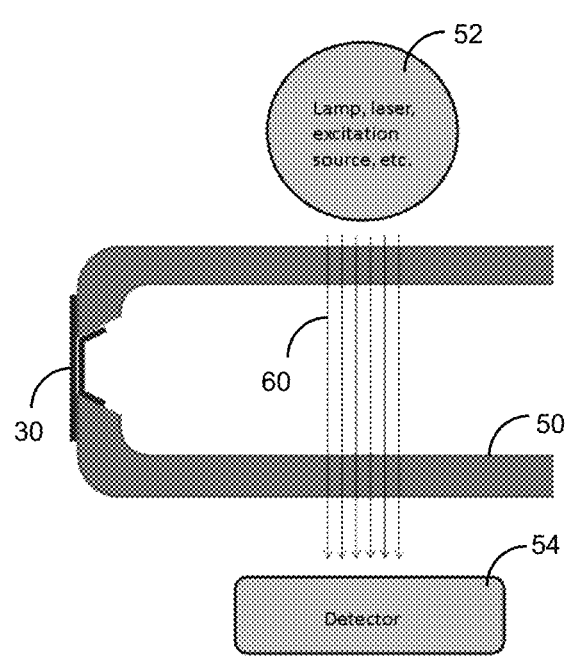

A generic cell-free assay device utilizing a GNM to hold a PLB and an internal probe for monitoring the endopeptidase activity of a toxin that inserts itself into and/or translocates through the PLB is shown in FIG. 4. In this example, the protein or toxin's interaction, translocation, or binding to the bilayer is measured using a lipid bilayer that separates a first electrolyte volume from a second electrolyte volume. The second electrolyte volume comprises a component to measure the fluorescence of the enzymatic target after it has been acted upon by the toxin or protein.

Figure 5:
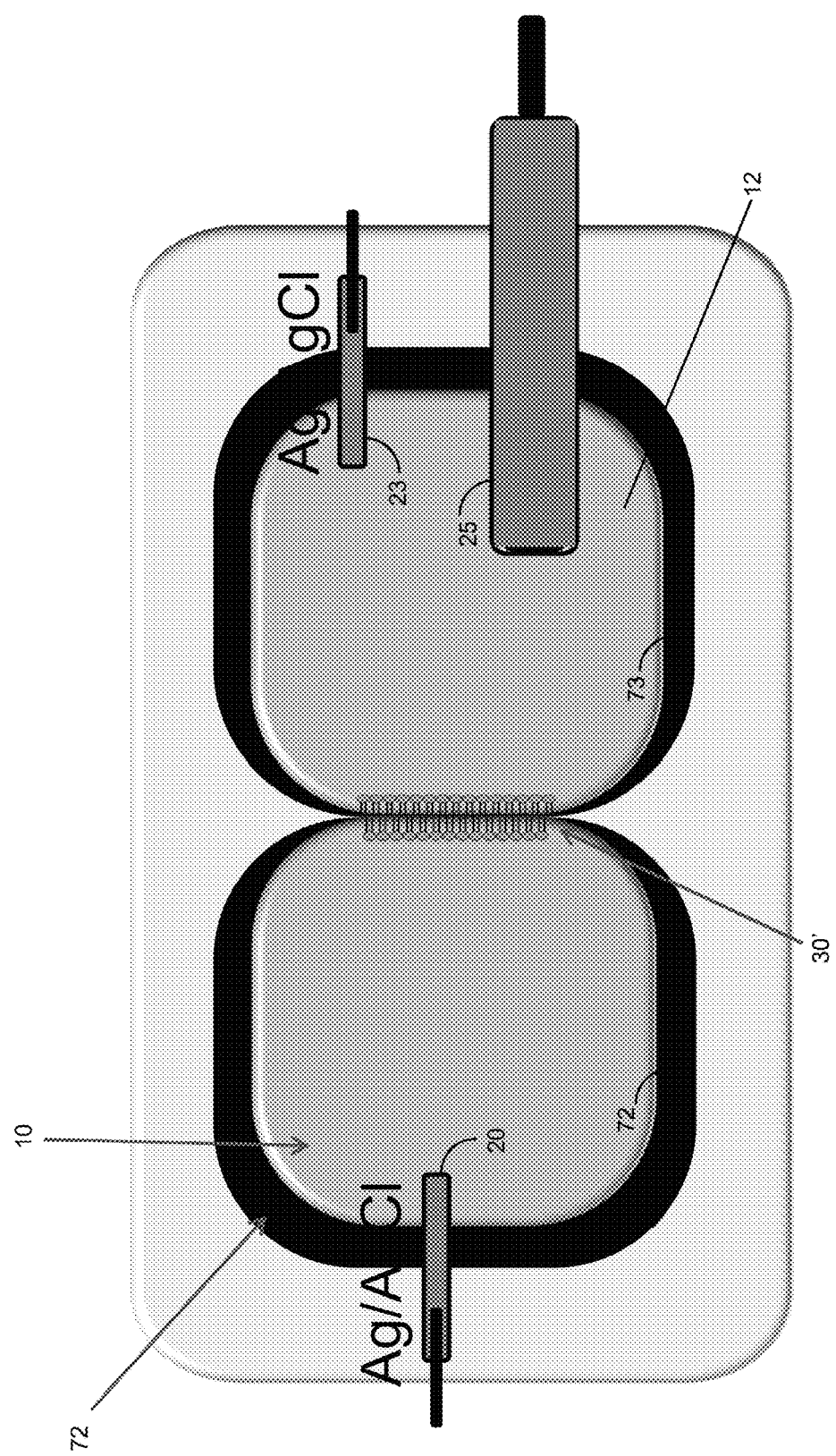
FIG. 5 shows a cross-section of a cell-free assay device comprising an encapsulated lipid bilayer, a first electrolyte volume (left) 10, and a second electrolyte volume (right) 12 comprising an internal probe 25 that can be used to monitor the activity of a toxin or protein that has inserted into and/or translocated through the PLB 30'.

In FIG. 5 a cell-free assay device is comprised of an encapsulated lipid bilayer, a first electrolyte volume (left side, FIG. 5), and a second electrolyte volume (right side, FIG. 5). The first electrolyte volume is constructed with a first electrode. The second electrolyte volume is constructed with a second electrode (top right of second electrolyte volume) and a probe (bottom right of second electrolyte volume). The device in FIG. 5 is used to measure an electronic change when a toxin or protein forms a pore or channel within the lipid bilayer. The probe is configured to measure endopeptidase activity in the second electrolyte volume.

Figure 6:
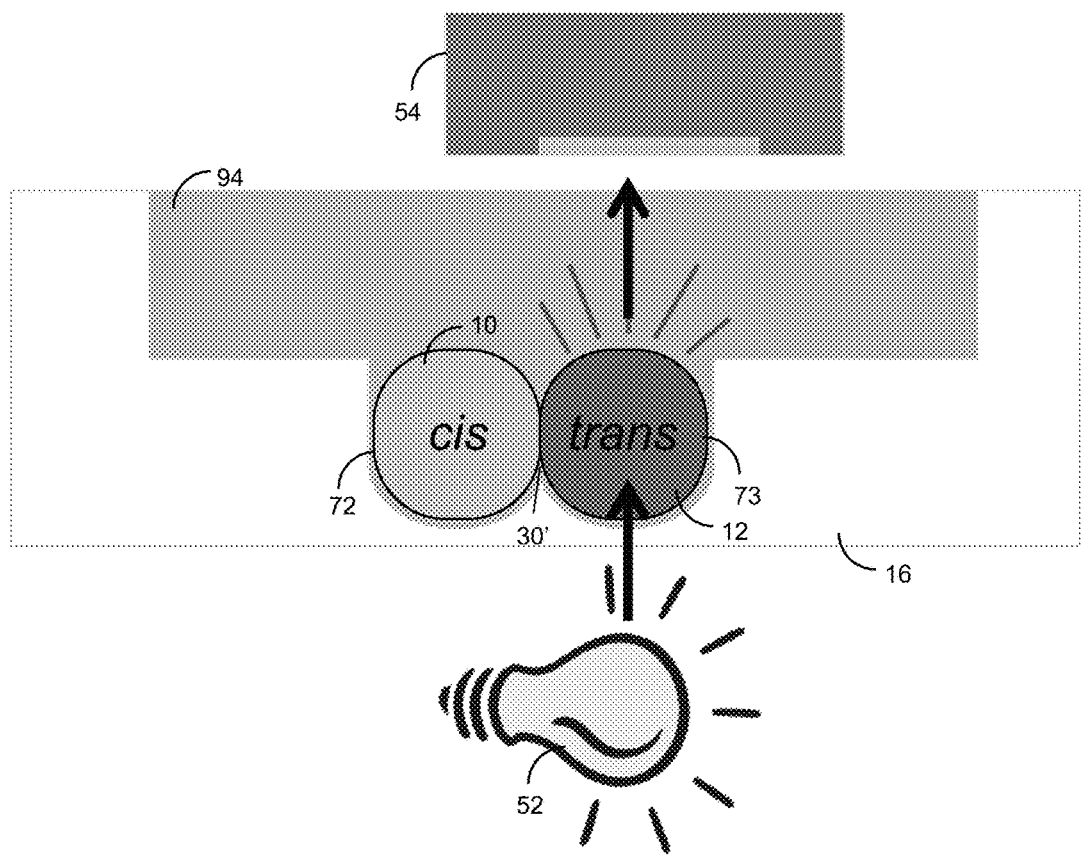
FIG. 6 shows a cross-section of a cell-free assay device comprising and encapsulated lipid bilayer, a first electrolyte volume (left or cis) and a second electrolyte volume (right or trans). The proteinase or enzymatic activity of the active toxin or protein is measured after it, or a portion thereof, has translocated through the lipid bilayer and is measured using an excitation source and detector outside of the device. In some embodiments the source and detector can be on the same or opposite sides of the device being analyzed.

In FIG. 6 a cell-free assay device is comprised of an encapsulated lipid bilayer, a first electrolyte volume (left or cis) and a second electrolyte volume (right or trans). The source and detector are configured to measure endopeptidase activity in the second electrolyte volume via, fluorescence loss or gain, fluorescence polarization, or FRET.

Example 3

Use of Pressure for Detecting a Modified Target

Figure 7:
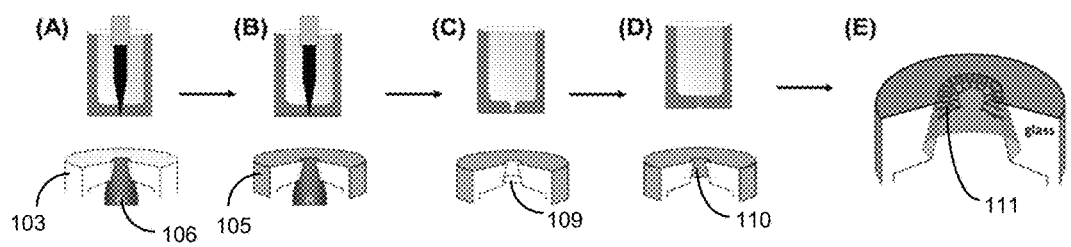
FIG. 7 shows a schematic drawing of the fabrication steps used to produce an anti-cSNAP-25 antibody modified GNM (AMGNM) starting from a glass nanodisk electrode showing covalent attachment of linkers 110 (e.g., silane linkers) and binding agents 111 (e.g., antibodies).

In order to demonstrate the basic feasibility of using an antibody coated pore to characterize the concentration of an antigen, an antibody-modified glass nanopore membrane (AMGNM) was developed. An AMGNM is sometimes referred to as "a site specific chemically modified nanopore" and is described in international patent application number PCT/US12/33142, which is incorporated herein by reference. In the work described herein, the antigen or modified target is a cleaved form of SNAP-25, cSNAP-25, which is the enzymatic target of botulinum toxin type A (BoNT/A). FIG. 7. Shows a portion of a fabrication process of an AMGNM, starting with a nanodisk electrode 103. Initially, the outside glass surface of a nanodisk electrode, whose Pt diameter matches that of the desired channel size, was chemically protected with cyano-silane 105 (3-cyanopropy-ldimethylchlorosilane) that limits non-specific binding (7C). A small amount of non-specific binding to this region does not significantly affect the measurement since this surface is outside the aperture and/or channel of the GNM. After the external coating was applied, the Pt 106 is removed via electrochemical etching and mechanical removal (7C), resulting in an aperture 109. Once the Pt is removed, the internal glass was functionalized via silane chemistry with an amino-terminated silane (3-aminopropyldimethylethox-ysilane) 110 (7D). This chemical modification provided active amino sites for reaction with a heterobifunctional crosslinker (sulfosuccinimidyl-4-[N-maleimidomethyl]cy-clohexane-1-carboxylate). The crosslinker comprised N-hy-droxysuccinimide ester and maleimide groups that react with both amine and sulfhydryl groups, respectively. Once the crosslinker was reacted with the free amino groups of the silane coating, a direct site for antibody attachment 111, via a sulfhydryl, was available on the internal glass surface 7E. Reactive sulfhydryl groups were introduced to anti-cSNAP-25 monoclonal antibodies (binding agents) by reducing the disulfide bonds in the hinge region via 2-mercaptoethylam-ine-HCl, producing free thiols to form stable thioether bonds with the maleimide groups of the crosslinker on the glass surface. During each step of the AMGNM production process, the rectification of the pore was characterized in order to verify that the surface modification has advanced as expected.

Figure 8:
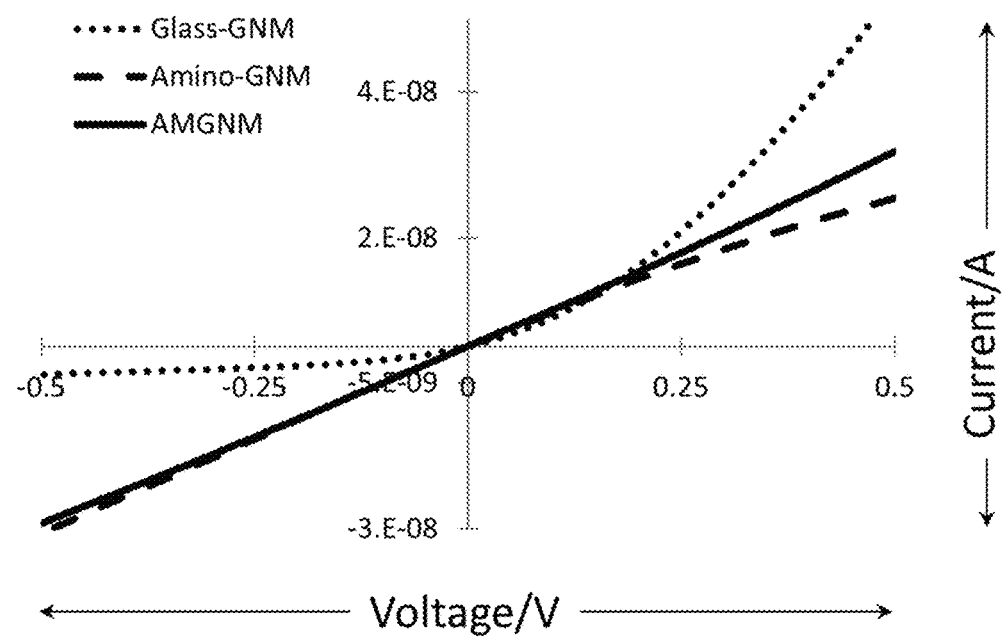
FIG. 8 shows an example of current-voltage traces characterizing the current response of a 100 nm radius GNM for different surface modifications: bare glass GNM (dotted line, highest at 0.5V), amino-functionalized GNM (dashed line, lowest at 0.5V), and AMGNM (AMGNM, solid line, middle at 0.5V). Data were collected using 150 mM NaCl (pH 7.2). Plotted values are offset corrected.

FIG. 8 shows an example of a current-voltage trace for each of the surface modifications used during AMGNM fabrication, excluding the crosslinker addition step. Due to the instability of the active maleimide surface and its susceptibility to hydrolysis, the ion current rectification response for this functionalization-step was not characterized. The degree of ion current rectification, and subsequent changes to the current rectification, were quantified using a current rectification ratio, which was calculated from the ratio of the current amplitude at a given positive voltage relative to the current amplitude at the opposite magnitude negative voltage ($R=i_{+v}/i_{-v}$). A bare glass surface (substrate) was composed of negatively charged silicon oxide molecules, yielding a negatively charged surface. The net negative charge on the glass yielded a highly rectified current response, see FIG. 8 (dotted line trace, Glass-GNM). The amplitude of the positive current was larger relative to the negative current amplitude, resulting in a rectification ratio (R at 480 mV) of ~12. After a glass nanopore surface is functionalized with the amine terminated silane, the negative silicon oxide molecules were replaced by positively charged amine groups ($pK_a$ of 9-10). This was directly reflected by a decrease in current rectification (dashed line trace, Amino-GNM) and a smaller relative rectification ratio of R~0.9. The covalent reaction of the heterobifunctional crosslinker with these amines yields free maleimide groups ($pK_a$~9.5) on the surface, which was anticipated to have a similar surface charge to the amines based on the pKa (data not shown). Finally, IgG, anti-cSNAP-25 antibodies were attached to the surface of the glass via the free maleimide groups, and this appears to neutralize any charge on the pore surface by slightly increasing the current rectification ratio to R~1 (solid line trace, AMGNM). Once the anti-SNAP-25 AMGNM was fabricated, it was ready to be used to characterize cSNAP-25 concentrations.

Figure 9A:
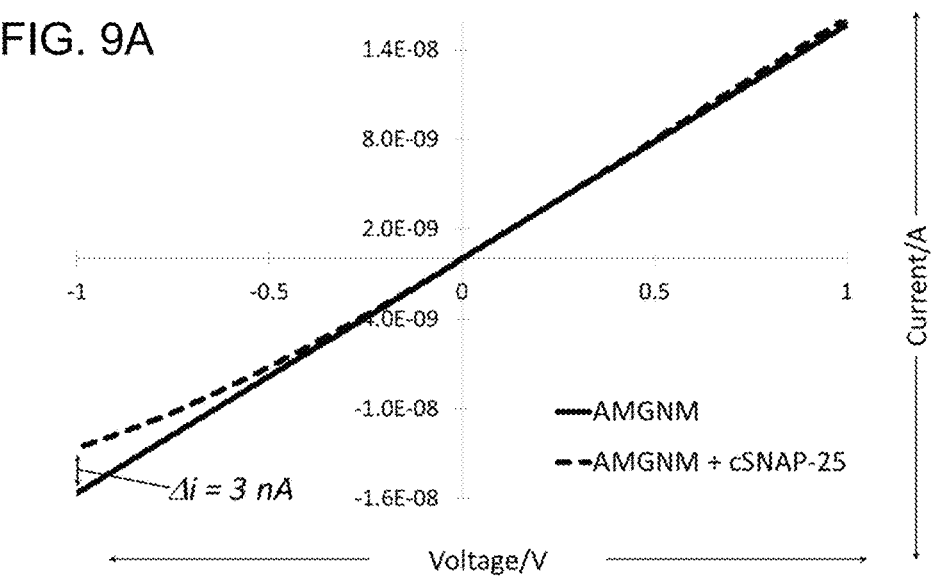
FIG. 9A shows a measured current response of a 75 nm radius anti-cSNAP-25 antibody-functionalized AMGNM before (solid line) and after (dashed line) exposure to cSNAP-25 (cleaved SNAP-25, e.g. modified target molecule), as a function of the applied voltage.
Figure 9B:
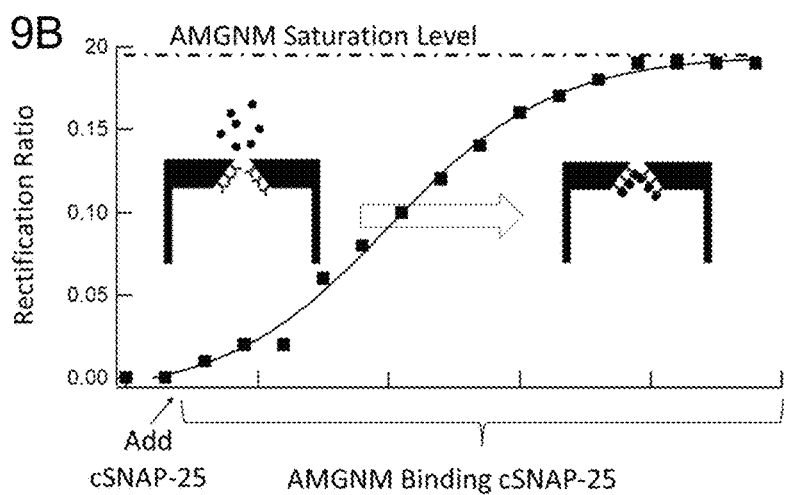
FIG. 9B shows a plot illustrating the change in the AMGNM rectification ratio (R=i+1V/i−1V) as 5 µM cSNAP-25 binds the pore aperture over time.
Figure 9C:
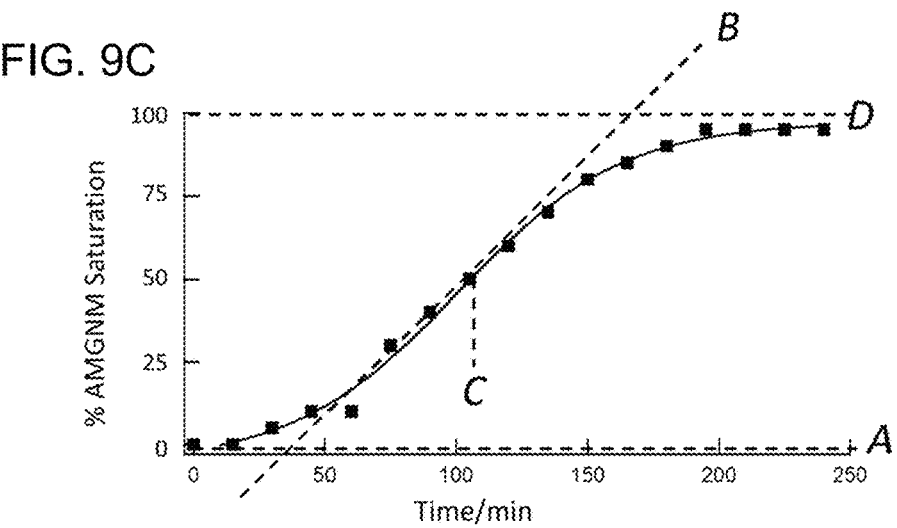
FIG. 9C shows an example of 5 µM binding data normalized and fit to a 5-parameter non-linear regression model.

The ability to quantify the presence of a target molecule using a current rectification approach was demonstrated FIG. 9. A 75 nm radius AMGNM (channel) was coated with an anti-cSNAP-25 monoclonal antibody (binding agent), which binds free cSNAP-25 molecules (modified target) in solution (e.g., an electrolyte solution). Initially, the current response of the anti-cSNAP AMGNM was measured as a function of voltage in a 150 mM NaCl (pH 7.2) solution in the absence of antigen (FIG. 9, solid line trace). cSNAP-25 is then introduced and the AMGNM immediately begins to bind the antigen, introducing charge to the surface resulting in increased rectification (FIG. 9A, solid line compared to dashed line). As mentioned above, the AMGNM has a relatively neutral surface. However, the cSNAP-25 peptide, based on its amino acid sequence (Cys-Lys-Ala-Asp-Ser-Asn-Lys-Thr-Arg-Ile-Asp-Glu-Ala-Asn-Glu), is anticipated to have excess negative charge at pH~7 as there are 4 acidic residues (Asp and Glu) to 3 basic residues (Lys and Arg) in the cleaved peptide. The overall change in rectification at 1 V, from before the AMGNM binds any cSNAP-25 to after saturation, was on the order of 3,000 pA. Again, the degree of rectification (R) was quantified by calculating the ratio of the current amplitude at a given positive voltage relative to the current at the equal amplitude negative voltage. The level of rectification measured at semi regular time intervals, $R_t$, minus the initial rectification ratio, $R_0$ (i.e. the rectification ratio of the pore in the absence of the antigen), is depicted in FIG. 9B. The rectification ratio of the AMGNM changed as a function of time and produced a sigmoid-like curve for which the rate of change depends on the concentration of cSNAP-25 introduced into the experimental cell. The rectification ratio data was then normalized and presented as a percent of AMGNM binding site saturation, FIG. 9C. The normalized percent of AMGNM binding site saturation data was fit to a 5-parameter non-linear regression model: $F(t)=A+(D/(1+(t/C)^B)^E)$, A is the minimum asymptote or the initial level of rectification when no antigen was present (i.e., 0%), B is the slope factor or steepness coefficient of the curve indicating the rate of cSNAP-25 binding, C is the inflection point, D is the maximum asymptote or final level of rectification (i.e., 100% saturation), E is the asymmetry factor and provides information on the rate of transport from bulk solution into the pore, and t is time. B and C provide information on the kinetics of binding and are concentration dependent, while A serves as a baseline for the unbound state of the AMGNM and can be used to verify that the pore is behaving correctly prior to antigen addition.

Figure 10:
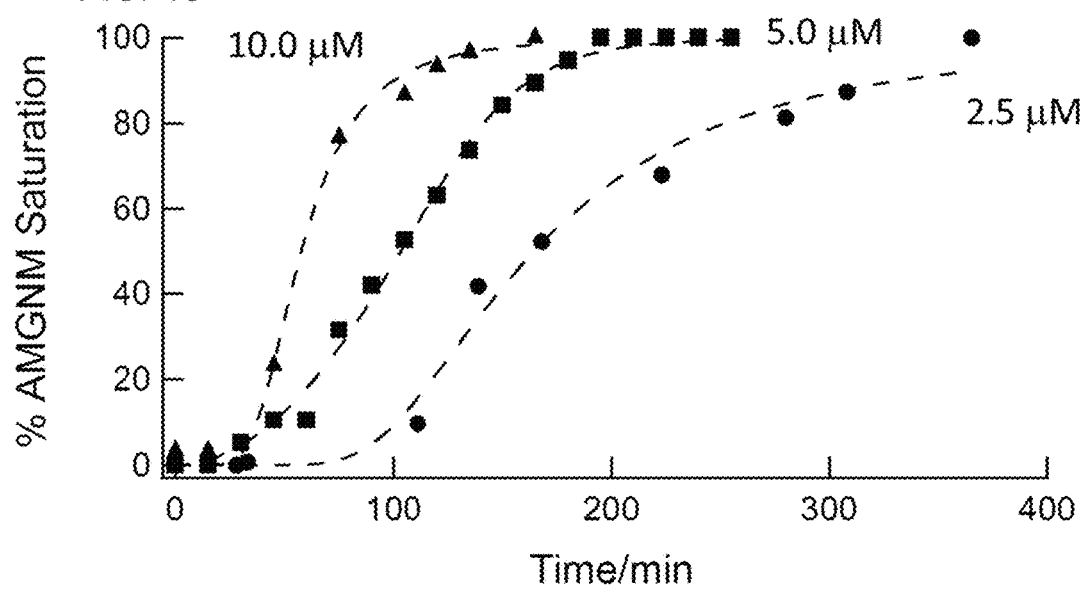
FIG. 10. shows percent saturation of AMGNM binding sites as a function of time for 2.5 µM cSNAP-25 (circles), 5.0 µM cSNAP-25 (squares), and 10 µM cSNAP-25 (triangles).

The characterization of the concentration of cSNAP-25 using the AMGNM measurement, was detected over various concentrations using pure cSNAP-25. Similar to the analysis described above, rectification ratio data for each concentration of cSNAP-25 was normalized and presented as a percent of AMGNM binding site saturation. FIG. 10 shows representative traces for the % saturation as a function of time for the detection of 2.5 micromolar, 5.0 micromolar, and 10.0 micromolar cSNAP-25. As shown, the rate of cSNAP-25 binding to the AMGNM was concentration dependent, with 10 micromolar binding proceeding at the fastest rate (i.e., steepest slope) and 2.5 micromolar proceeding at the slowest rate (i.e., shallowest slope). This data demonstrated the ability of an AMGNM measurement to characterize the concentration of cSNAP-25. However, the time required to obtain a diffusion-based measurement of cSNAP-25 using an AMGNM was not ideal due to the prolonged time required to complete the measurement. For example, detection of 10 micromolar cSNAP-25 took about 2 hours and the detection of 2.5 micromolar cSNAP-25 took about 6 hours.

Figure 11:
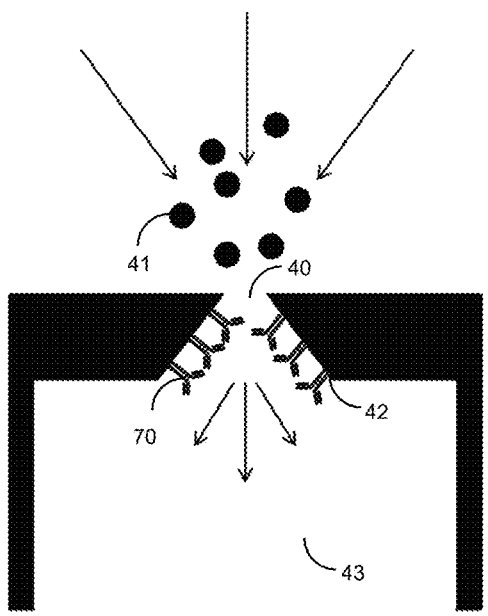
FIG. 11 shows a schematic representation of a negative pressure (e.g., lower pressure inside the AMGNM than outside) being pulled on an AMGNM, thus increasing the transport of the modified target molecule to the channel. The arrow indicates the direction of flux or flow induced by a negative pressure in the second chamber 43.
Figure 12:
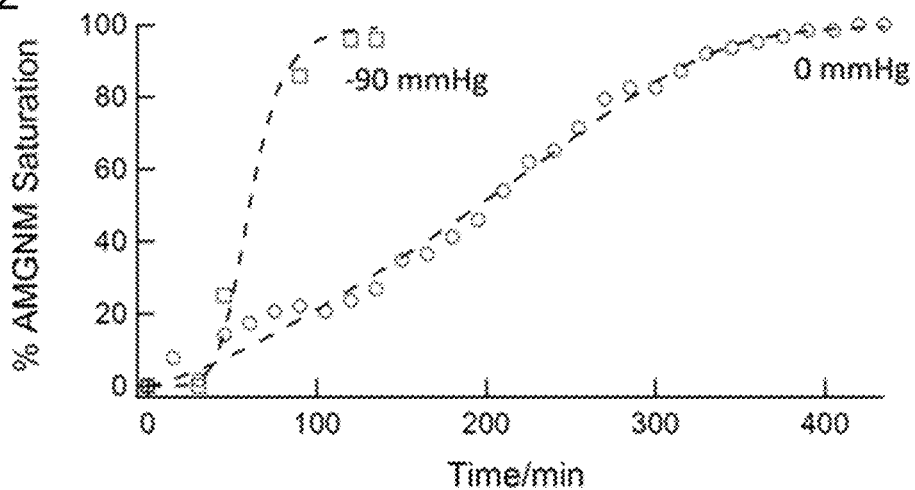
FIG. 12 shows percent saturation of AMGNM binding sites as a function of pressure for 500 nM cSNAP-25 at 0 mmHg (circles) and −90 mmHg (squares).

To improve the rate of binding, and thus the AMGNM detection limit from a time-scale based perspective, a pressure gradient was implemented as a means of enhancing the transport of cSNAP-25 to the AMGNM orifice in order to speed up the rate of reaction and thus be able to characterize low cSNAP-25 concentration (i.e. pM) in a reasonable time frame (i.e. under a few hours). A negative pressure was manually applied to the back the of an AMGNM, thus creating a pressure gradient of high pressure to low pressure across the membrane from the AMGNM exterior relative to the interior. The application of pressure introduced a convection-based component to the primarily diffusion based flux of cSNAP-25 molecules into the AMGNM, increasing the rate of reaction (i.e., interaction between modified target and binding agents), as illustrated in FIG. 11. The rate of detection of cSNAP-25 (500 nM) binding to an antibody coated AMGNM in the presence of a −90 mmHg pressure gradient (squares) and in the absence of a pressure gradient (circles) was measured (FIG. 12).

Figure 13A:
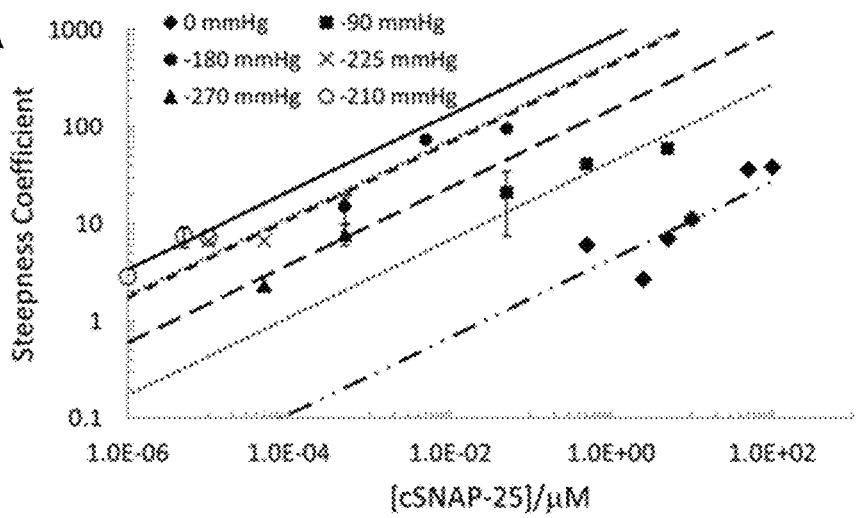
FIG. 13A shows a plot of the steepness coefficient, B, as a function of cSNAP-25 concentration (100 μM down to 1 pM) and applied pressure (0 mmHg to −270 mmHg). Data were fit using a power series model as shown with the solid and dashed curves.
Figure 13B:
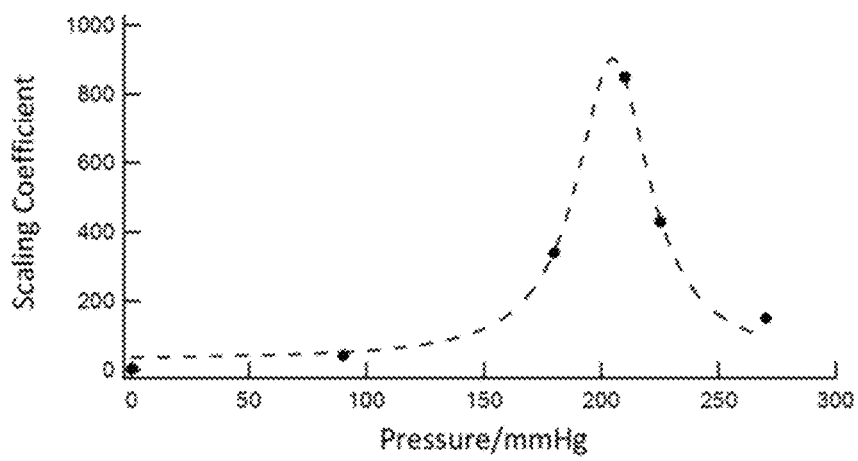
FIG. 13B shows a plot of the scaling coefficient, A, as a function of applied pressure.

To further assess and improve the utilization of pressure gradients as a means of increasing the rate of reaction of cSNAP-25 binding to the AMGNM, the use of larger pressure gradients was examined. The steepness coefficient (B), which is directly related to the rate of reaction, was determined as a function of cSNAP-25 concentration over a pressure range of 0 to −270 mmHg (FIG. 13A). A log plot was used here for display purposes, allowing the lower concentrations of cSNAP-25 characterized to be adequately visualized. All data points on this plot represented single experiments in which cSNAP-25 was characterized using an AMGNM, in combination with the designated applied pressure gradient. Each pressure dependent data set in FIG. 13A was then fit using a power series model $\log(y)=\log(A)+m\log(x)$, where y is the steepness coefficient, A is the scaling coefficient, x is the concentration of antigen, and m is the slope. The use of pressure increased the scaling coefficient, A, by ~10-fold for each increment of 90 mmHg, between pressures of 0 and −180 mmHg, as indicated by the even spacing between the 0, −90 and −180 mmHg data sets. At pressures above 180 mmHg, the increase in reaction rate begins to slow down, as indicated by the −210 mmHg scaling coefficient only being slightly higher than the −180 mmHg scaling coefficient. At pressure gradients greater than −210 mmHg the reaction rate was reduced. To evaluate the influence of the applied pressure gradient on the cSNAP-25 binding rate, the scaling coefficients for each pressure dependent data set from FIG. 13A were plotted as a function of applied pressure in FIG. 13B. As shown, the scaling coefficient peaked at ~210 mmHg and then began to decrease at higher pressures. Without being limited to theory, this peak likely reflected the rate of molecular flux as it relates to the antigen/antibody binding kinetics. At pressures less than −210 mmHg, the binding rate occurred faster with pressure. Without being limited to theory this was most likely because molecules were delivered more quickly to the pore surface due to enhanced flux, increasing the molecule/pore encounter rate, and thus the rate of detection. However, at pressures greater than −210 mmHg, the binding rate decreased. Without being limited to theory this was most likely because the pressure gradient, which increased the molecule velocity, minimizes the residence time of the molecule at the pore surface, thus decreasing its likelihood of binding to the AMGNM surface. The fact that all of the data sets share the same slope (m=~0.4), indicated that although the use of pressure altered the binding rate, it did not appear to alter the overall binding mechanism.

Figure 14:
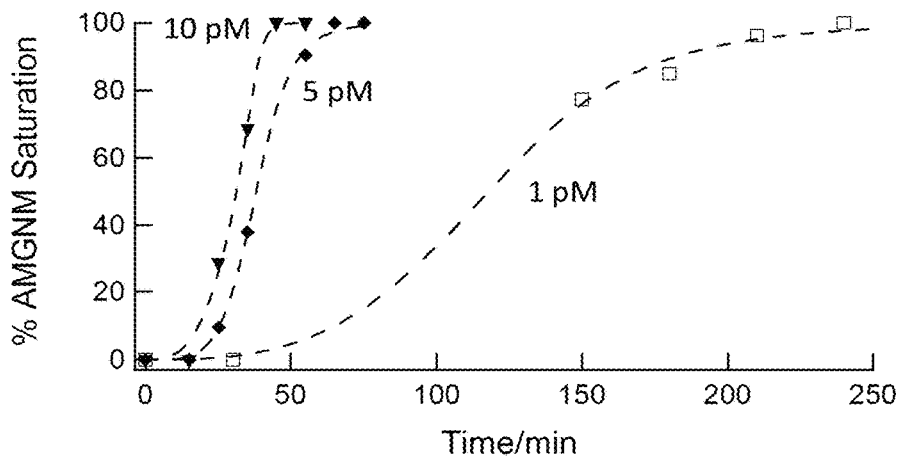
FIG. 14 shows percent saturation of AMGNM binding sites as a function of time for 1 pM cSNAP-25 (squares), 5.0 pM cSNAP-25 (diamonds), and 10 pM cSNAP-25 (triangles), with −210 mmHg applied pressure.

Based on the results shown in FIG. 13, −210 mmHg was determined to be the optimal pressure for detecting cSNAP-25 in solution, at low concentrations (e.g. below 1 μM) via the AMGNM measurement. This pressure yielded the fastest obtainable reaction rate for AMGNMs ranging from 50 to 100 nm in radii and for the on/off kinetics associated with cSNAP-25 and its specific antibody. A demonstration of the ability to characterize low concentrations of cSNAP-25 (e.g., in the picomolar range) using an AMGNM measurement is shown in FIG. 14. The binding of three concentrations of cSNAP-25 at 1 pM, 5 pM, and 10 pM, to an antibody coated AMGNM was measured using an applied pressure of −210 mmHg. The binding of 10 pM cSNAP-25 occurred the fastest (i.e. had the steepest binding slope) and 1 pM occured the slowest (i.e. had the shallowest binding slope). By comparing the detection times in FIG. 14, utilizing −210 mmHg, to those shown in FIG. 10, obtained at 0 mmHg, demonstrated the ability to detect cSNAP-25 within the same time frame at concentrations six orders of magnitude lower with the use of −210 mmHg as compared to without.

These results demonstrated the ability and utility of utilizing a pressure gradient, in combination with a current rectification measurement as a means of improving sensitivity, decreasing the limits of detection, as well as deceasing the time required to characterize an antigen using an AMGNM.

Figure 15A:
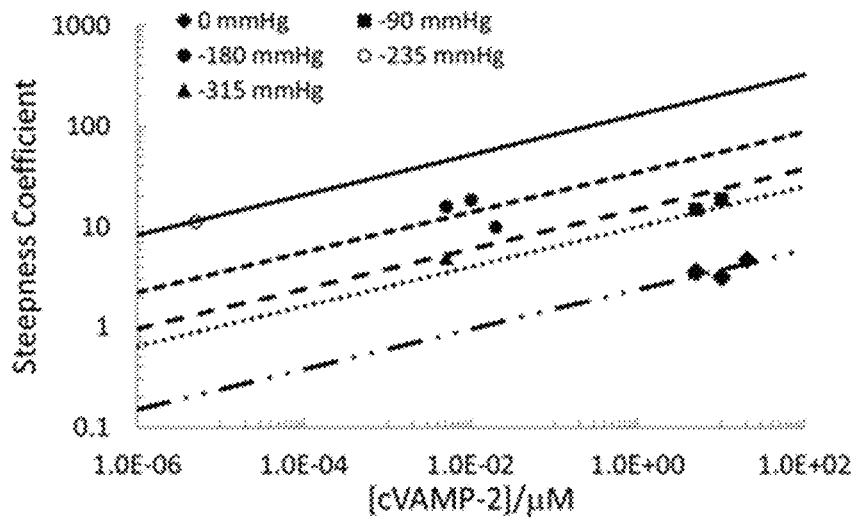
FIG. 15A shows a plot of the steepness coefficient, B, as a function of cVAMP-2 (cleaved VAMP-2, e.g. modified target molecule) concentration (20 μM down to 1 pM) and applied pressure (0 mmHg to −315 mmHg). Data were fit using a power series model as shown with the solid and dashed curves.

The general concept of altering the detection time of a modified target is not limited to cSNAP-25, and the same approach was applied to other binding pairs. AMGNMs were fabricated for the detection of cleaved vesicle association membrane protein 2 (cVAMP-2), also known as the cleaved form of synaptobrevin 2, using the AMGNM production procedure described herein. In this procedure GNMs were functionalized (e.g., coated) with polyclonal cVAMP-2 antibodies instead of monoclonal cSNAP-25 antibodies. AMGNMs coated with polyclonal cVAMP-2 antibodies were used to detect free cVAMP-2 in solution over a concentration range of 1 pM to 20 μM, utilizing pressure gradients ranging from 0 mmHg to −315 mmHg. The level of rectification measured at semi-regular time intervals was monitored to produce sigmoid-like curves for binding of cVAMP-2, similar to the method described above, where the rate of rectification change depended, in part, on the concentration of cVAMP-2 introduced into the experimental cell. The steepness coefficient (B) as a function of cVAMP-2 concentration was determined over a pressure range of 0 to −315 mmHg (FIG. 15A). Each pressure dependent data set in FIG. 15A was fitted to a power series model to extract the scaling coefficient, A. The use of pressure for the detection of cVAMP-2 increased the scaling coefficient, A, by ~5-fold for each increment of 90 mmHg, between pressures of 0 and −180 mmHg. At around −235 mmHg the detection rate seemed to peak, i.e., occur fastest, after which, larger pressure gradients yielded a decrease in the scaling coefficient. To evaluate the influence of the applied pressure gradient on the cVAMP-2 binding rate, the scaling coefficients for each pressure dependent data set from FIG. 15A were plotted as a function of applied pressure in FIG. 15B.

Figure 15B:
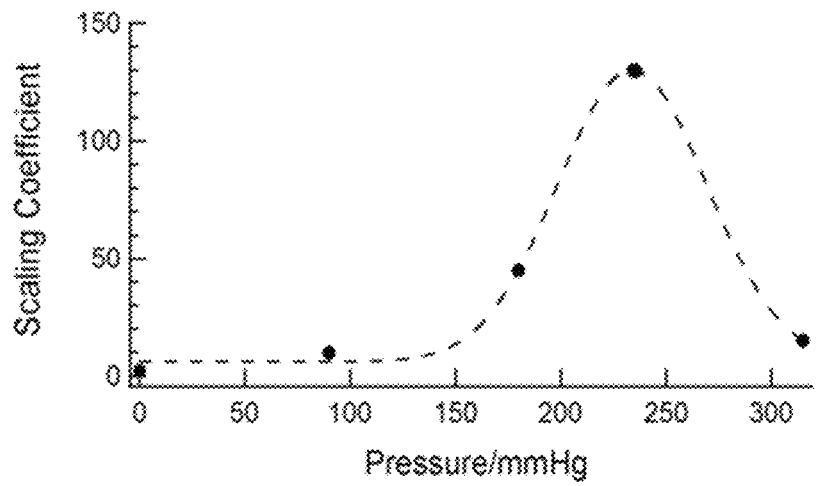
FIG. 15B shows a plot of the scaling coefficient, A, as a function of applied pressure.

The scaling coefficient for cVAMP-2 peaked at ~235 mmHg as shown in FIG. 15B compared to a pressure peak of ~210 mmHg for cSNAP-25. Without being limited to theory, the effect of a pressure gradient may produce different results due to differences of the modified target molecules cSNAP-25 and cVAMP-2 (i.e. different size, makeup, and charge). For example, cSNAP-25 is a 15 residue peptide with a net charge of −1 (at pH~7), while cVAMP-2 is a 76 residue peptide with a net charge of −4. Further, the influence of −90 mmHg pressure gradient increments was larger for cSNAP-25 relative to cVAMP-2 as indicated by A increasing by 10-fold and 5-fold, respectively. Without being limited to theory, this may be due to the size and charge difference between the two antigen molecules. For example, the smaller and less charged cSNAP-25 will potentially transport through solution for a given pressure faster, while the larger and more charged cVAMP-2 will be less readily transported through solution, by the same pressure. These results demonstrated the versatility of this technique for the binding of any molecule in a binding pair. Without being limited to theory, the pressure dependence and/or the optimal pressure (i.e. the pressure that yields the fastest obtainable detection times) for an AMGNM measurement may be a function of a binding agent characteristic (e.g., size, makeup, charge, identity, and the like), the on/off kinetics of a binding pair as well as the size, geometry, and the like, of an aperture or channel.

In practice, the detection and influence of pressure is calibrated before detecting an unknown concentration. In addition, a calibration coefficient, standard curve, empirical factor, and the like, is often used to normalize the results obtained from AMGNMs with different orifice sizes and/or geometries.

Example 4

Examples of Embodiments

The examples set forth below illustrate certain embodiments and do not limit the technology.

A1. A cell-free assay device, comprising:
 a lipid bilayer configured to separate a first electrolyte volume and a second electrolyte volume;
 a first component configured to detect a change in the lipid bilayer resulting from interaction of an assay molecule, or a portion thereof, with the bilayer; and
 a second component configured to detect a modified target molecule resulting from modification of a target molecule by the assay molecule, or portion thereof, wherein the modification is, at least in part, in the second volume.

A2. The device of embodiment A1, wherein the assay molecule is chosen from a protein, a toxin, or a portion thereof.

A2.1. The device of embodiment A1 or A2, wherein the assay molecule is a pore forming molecule.

A3. The device of any one of embodiment A1 to A2.1, wherein the interaction of the assay molecule, or portion thereof, is chosen from: (i) insertion of the assay molecule, or a portion thereof, into the bilayer, (ii) translocation of the assay molecule, or a portion thereof, through the bilayer, (iii) binding of the assay molecule, or a portion thereof, to the bilayer, (iv) association of the assay molecule or a portion thereof with the bilayer, or (v) a combination thereof.

A3.1 The device of any one of embodiments A1 to A3, wherein the lipid bilayer comprises one or more receptors.

A3.2. The device of embodiment A3.1, wherein the interaction of the assay molecule, or portion thereof, comprises binding of the assay molecule, or a portion thereof, to at least one receptor on the bilayer.

A4. The device of any one of embodiments A1 to A3.1, wherein the assay molecule, or portion thereof, is capable of forming a pore in the lipid bilayer.

A4.1. The device of any one of embodiments A1 to A4, wherein the interaction of the assay molecule, or portion thereof, comprises insertion of a pore in the lipid bilayer.

A5. The device of any one of embodiments A1 to A4.1, wherein the change detected in the lipid bilayer is a change in conductance, resistance, impedance, current, electrical potential, current rectification, or a combination thereof.

A6. The device of any one of embodiments A1 to A5, wherein the first component comprises electrodes configured to contact the first electrolyte volume and the second electrolyte volume.

A7. The device of any one of embodiments A1 to A6, wherein the first component is configured to detect a change between the first electrolyte volume and the second electrolyte volume.

A8. The cell-free assay device of embodiment A7, wherein the change between the first electrolyte volume and second electrolyte volume comprises insertion of the assay molecule, or portion thereof, which assay molecule, or portion thereof, has inserted in the lipid bilayer from the first electrolyte volume into the second electrolyte volume.

A8.1. The cell-free assay device of embodiment A7 to A8, wherein the change between the first electrolyte volume and second electrolyte volume comprises traversal of the assay molecule, or portion thereof, which assay molecule, or portion thereof, has traversed the lipid bilayer from the first electrolyte volume into the second electrolyte volume.

A9. The device of embodiment A7 to A8.1, wherein the change detected between the first electrolyte volume and second electrolyte volume is a change in conductance, resistance, impedance, current, electrical potential, current rectification or a combination thereof.

A10. The device of any one of embodiments A1 to A9, wherein the target molecule is an enzymatic target of the assay molecule or a portion thereof.

A11. The device of any one of embodiments A1 to A10, wherein the target molecule is located in the second electrolyte volume.

A12. The device of any one of embodiments A1 to A11, wherein the second component is configured to detect a detectable signal that is directly or indirectly produced by or emitted by the modified target molecule.

A13. The device of embodiment A12, wherein the second component comprises a detector configured to detect the detectable signal.

A14. The device of embodiment A13, wherein the detector comprises one or more electrodes.

A15. The device of embodiment A13 or A14, wherein the detector comprises one or more of a laser, fiber optic cable, excitation source and photodetector.

A16. The device of any one of embodiments A12 to A15, wherein the detectable signal is electromagnetic radiation.

A17. The device of embodiment A16, wherein the electromagnetic radiation is visible light.

A17.1. The device of any one of embodiments A12 to A17, wherein the detectable signal is a fluorescent signal.

A18. The device of any one of embodiments A12 to A17.1, wherein the unmodified target molecule does not emit the detectable signal, or the second component is not configured to detect the detectable signal from the unmodified target molecule.

A19. The device of any one of embodiments A12 to A18, wherein the detectable signal is emitted or quenched by at least one fluorescent label attached to, or associated with, the modified target molecule.

A19.1. The device of any one of embodiments A12 to A19, wherein the detectable signal is quenched by a quencher.

A20. The device of any one of embodiments A13 to A19.1, wherein the second component is configured to detect the modified target molecule directly.

A21. The device of any one of embodiments A1 to A20, wherein the second component comprises a binding agent that specifically binds to the modified target molecule.

A22. The device of embodiment A21, wherein the second component is configured to detect a binding event between the modified target and the binding agent.

A23. The device of any one of embodiments A1 to A22, wherein the second component is configured to detect immobilization of the modified target.

A24. The device of any one of embodiments A1 to A23, wherein the modification of the target molecule is chosen from enzymatic cleavage, covalent addition of a molecule, binding of the assay molecule or a portion thereof, or a combination thereof.

A25. The device of embodiment A24, wherein the enzymatic cleavage comprises proteolytic cleavage.

A26. The device of any one of embodiments A1 to A25, wherein the bilayer comprises a planar lipid bilayer.

A27. The device of embodiment A26, wherein the planar lipid bilayer spans an aperture in a first substrate.

A28. The device of embodiment A26, wherein the planar lipid bilayer is supported across the aperture in the first substrate.

A29. The device of any one of embodiments A1 to A28, wherein the bilayer comprises an encapsulated lipid bilayer.

A29.1 The device of any one of embodiments A1 to A29, wherein the bilayer comprises a droplet interface bilayer.

A30. The device of embodiment A29, wherein the encapsulated lipid bilayer comprises a first droplet formed by a first lipid monolayer and a second droplet formed by a second lipid monolayer that are in contact along at least a portion of the first and second monolayers to form the encapsulated lipid bilayer.

A31. The device of embodiment A30, wherein the first droplet forms the first electrolyte volume and the second droplet forms the second electrolyte volume.

A32. The device of any one of embodiments A1 to A31, wherein the lipid bilayer further comprises additives.

A33. The device of embodiment A32, wherein the additives are chosen from cholesterol, polyethylene glycol, cell surface receptors, gangliosides, ceramides, sphingomyelin, glycosphingolipids or combinations thereof.

A34. The device of any one of embodiments A1 to A33, comprising a third electrolyte volume.

A35. The device of embodiment A34, wherein the second electrolyte volume contacts the third electrolyte volume.

A36. The device of embodiment A34, wherein the second electrolyte volume does not contact the third electrolyte volume.

A37. The device of any one of embodiments A1 to A36, wherein the second electrolyte volume does not contact the first electrolyte volume.

A38. The device of any one of embodiments A1 to A37, wherein the second component comprises a glass nanopore membrane (GNM).

A39. The device of embodiment A38, wherein the GNM comprises the aperture.

A40. The device of embodiment A38 or A39, wherein the GNM comprises the channel.

A41. The device of any one of embodiments A38 to A40, wherein the second electrolyte volume and the third electrolyte volume are separated by the aperture.

A42. The device of any one of embodiments A39 to A41, wherein the second electrolyte volume contacts the third electrolyte volume at the aperture A43. The device of any one of embodiments A38 to A42, wherein the GNM comprises the binding agent.

A44. The device of any one of embodiments A1 to A43, wherein the second component comprises a second substrate.

A45. The device of embodiment A44, wherein the GNM comprises the second substrate.

A46. The device of embodiment A45, wherein the channel comprises the second substrate.

A47. The device of any one of embodiments A44 to A46, wherein the second substrate comprises the binding agent.

A48. The device of any one of embodiments A34 to A47, wherein the second component comprises electrodes configured to contact the second electrolyte volume and the third electrolyte volume.

A48.1 The device of embodiment A48, wherein the first component and the second component comprises one or more electrodes that are the same electrode.

A49. The device of any one of embodiments A34 to A48.1, wherein the detectable signal comprises a change between the second electrolyte volume and the third electrolyte volume chosen from a change in conductance, resistance, impedance, current, electrical potential, ion current rectification or a combination thereof.

A50. The device of any one of embodiments A34 to A49, wherein the second component is configured to detect a detectable signal in the second or third electrolyte volume.

A51. The device of any one of embodiments A34 to A50, wherein the second component is configured to detect a binding event in the second or third electrolyte volume.

A52. The device of any one of embodiments A10 to A51, wherein the assay molecule is a botulinum neurotoxin, or modified version or portion thereof, and the target molecule is a SNARE protein, or modified version or portion thereof.

A53. The device of any one of embodiments A34 to A52, comprising an apparatus configured to induce a pressure differential at a channel or aperture between the second and third electrolyte volumes.

A53.1 The device of embodiment A53, wherein the pressure differential is between the second electrolyte volume and the third electrolyte volume.

A54. The device of embodiment A53 or A53.1, wherein the apparatus is in effective communication with the second electrolyte volume or the third electrolyte volume, or the second electrolyte volume and the third electrolyte volume.

A55. The device of embodiment A53 or A54, wherein the apparatus comprises a chamber.

A56. The device of embodiment A55, wherein the chamber comprises the third electrolyte volume.

A57. The device of any one of embodiments A53 to A56, wherein the apparatus comprises a pressure control system.

A58. The device of embodiment A57, wherein the pressure control system comprises a pressure port.

A59. The device of embodiment A57, wherein the pressure control system comprises a syringe, a piston or a pump.

A60. The device of any one of embodiments A1 to A59, with the proviso that the device includes no cells.

A61. The device of embodiment A60, wherein the cells are from an organism.

A62. The device of any one of embodiment A1 to A61, wherein the lipid bilayer is an artificial lipid bilayer.

B1. A method for assaying an assay molecule, comprising:
(a) contacting an assay molecule with a first electrolyte volume of a cell-free assay device of any one of embodiments A1 to A61;
(b) detecting the presence, absence or amount of an interaction between the lipid bilayer and the assay molecule, or portion thereof; and
(c) detecting the presence, absence or amount of an interaction between the assay molecule, or portion thereof, with a target molecule, or portion thereof.

B1.1. The method of B1, wherein the target molecule, or portion thereof, is in the first, second and/or third electrolyte volume.

B1.2. The method of embodiment B1 or B1.1, wherein the assay molecule, or portion thereof, is a protein or toxin.

B1.3. The method of any one of embodiments B1 to B1.2, wherein the assay molecule is a pore forming toxin.

B1.4. The method of any one of embodiments B1 to B1.3, wherein the target molecule is an enzymatic target of the assay molecule, or portion thereof.

B2. The method of any one of embodiments B1 to B1.4, wherein the detecting in (b) comprises detecting insertion of the assay molecule, or portion thereof, into the lipid bilayer.

B3. The method of any one of embodiments B1 to B2, wherein the detecting in (b) comprises detecting translocation of the assay molecule, or portion thereof, into the second electrolyte volume.

B4. The method of any one of embodiments B1 to B3, wherein the detecting in (b) comprises detecting a change in the conductance, resistance, current, electrical potential, ion current rectification or a combination thereof of the lipid bilayer.

B5. The method of any one of embodiments B1 to B4, wherein the detecting in (c) comprises detecting a cleavage product of the target molecule.

B6. The method of embodiment B5, wherein the cleavage product is detected in the second electrolyte volume.

B7. The method of embodiment B5, wherein the cleavage product is detected in a third electrolyte volume.

B8. The method of any one of embodiments B5 to B7, wherein the cleavage product is immobilized on a substrate.

B9. The method of any one of embodiments B5 to B8, wherein detecting the cleavage product comprises monitoring a detectable label in association with the cleavage product.

B10. The method of any one of embodiments B1 to B9, wherein the detecting in (c) comprises inducing a pressure differential.

B10.1. The device of embodiment B10, wherein the pressure differential is between the second electrolyte volume and the third electrolyte volume.

B11. The method of any one of embodiments B1 to B10, wherein the detecting in (c) comprises adjusting the pressure of the third electrolyte volume.

B12. The method of any one of embodiments B10 to B11, wherein adjusting the pressure comprises adjusting the pressure such that the pressure in the third electrolyte volume is lower than the pressure in the second electrolyte volume.

B12.1 The method of any one of embodiments B10 to B11, wherein adjusting the pressure comprises adjusting the pressure such that the pressure in the second electrolyte volume is higher than the pressure in the third electrolyte volume.

B13. The method of any one of embodiments B7 to B12.1, wherein the detecting in (c) comprises detecting a change in the conductance, resistance, current, electrical potential, ion current rectification or a combination thereof of between the second electrolyte volume and the third electrolyte volume.

B14. The method of any one of embodiments B2 to B13, which comprises determining the potency of the assay molecule, or portion thereof.

B15. The method of embodiment B14, which comprises quantifying the detecting in (b) and the detecting in (c).

B16. The method of embodiment B14 or B15, wherein determining the potency of the toxin comprises detecting the presence, absence or amount of two or three of (i) insertion of the assay molecule, or portion thereof, into the lipid bilayer (ii) translocation of the assay molecule, or portion thereof, into the second electrolyte volume, and (iii) the cleavage product of the target molecule.

B17. The method of any one of embodiments B1 to B16, comprising determining whether a test substance neutralizes the assay molecule, or portion thereof.

B18. The method of embodiment B17, wherein the determining in B17 comprises prior to (b), introducing the test substance to the device.

B19. The method of embodiment B18, wherein determining in B17 comprises detecting the presence, absence or amount of two or three of (i) insertion of the assay molecule, or portion thereof, into the lipid bilayer (ii) translocation of the assay molecule, or portion thereof, into the second electrolyte volume, and (iii) the cleavage product of the target molecule.

B20. The method of any one of embodiments B17 to B19, wherein the test substance is an inhibitor of the assay molecule, or portion thereof.

B21. The method of any one of embodiments B17 to B20, wherein the test substance binds to, associates with, or acts on the assay molecule, or portion thereof.

C1. A cell-free assay device, comprising:
a lipid bilayer configured to separate a first electrolyte volume and a second electrolyte volume;

a first component configured to detect a change in the lipid bilayer;

a substrate comprising a first surface; an opposing second surface; a wall or walls between the first surface and the second surface; and a channel in the substrate comprising a proximal opening at the first surface, a distal opening at the second surface and an interior sidewall surface, wherein the proximal opening of the channel is configured to contact the second electrolyte volume and the distal opening is configured to contact a third electrolyte volume; and an binding agent attached to at least a portion of the interior sidewall surface of the channel, which binding agent can bind to an analyte.

C2. A cell-free assay device, comprising:

a lipid bilayer configured to separate a first electrolyte volume and a second electrolyte volume;

a first component configured to detect a change in the lipid bilayer;

a channel comprising a proximal aperture and an interior surface, wherein the proximal aperture separates the second electrolyte volume from a third electrolyte volume, the second electrolyte volume contacts the third electrolyte volume at the proximal aperture and the channel comprises the third electrolyte volume, or a portion thereof;

a binding agent attached to at least a portion of the interior surface of the channel; and a second component configured to detect a change in the third electrolyte volume.

C3. The device of embodiment C1 or C2, wherein the change in the bilayer is chosen from: (i) insertion of an assay molecule, or a portion thereof, into the bilayer, (ii) translocation of the assay molecule, or a portion thereof, through the bilayer, (iii) binding of the assay molecule, or a portion thereof, to the bilayer, (iv) association of the assay molecule or a portion thereof with the bilayer, or (v) a combination thereof.

C3.1 The device of any one of embodiments C1 to C3, wherein the lipid bilayer comprises one or more receptors.

C3.2. The device of embodiment C3.1, wherein the interaction of the assay molecule, or portion thereof, comprises binding of the assay molecule, or a portion thereof, to at least one receptor on the bilayer.

C4. The device of any one of embodiments C1 to C3.2, wherein the assay molecule is chosen from a protein, a toxin, or a portion thereof.

C5. The device of any one of embodiments C1 to C4, wherein the change in the bilayer comprises insertion of a pore.

C6. The device of any one of embodiments C1 to C5, wherein the change detected in the lipid bilayer is a change in conductance, resistance, impedance, current, electrical potential, current rectification or a combination thereof.

C7. The device of any one of embodiments C1 to C6, wherein the first component comprises electrodes configured to contact the first electrolyte volume and the second electrolyte volume.

C8. The device of any one of embodiments C1 to C7, wherein the first component is configured to detect a change between the first electrolyte volume and the second electrolyte volume.

C9. The cell-free assay device of embodiment C8, wherein the change between the first electrolyte volume and second electrolyte volume comprises insertion of the assay molecule, or portion thereof, which assay molecule, or portion thereof, has inserted in the lipid bilayer from the first electrolyte volume into the second electrolyte volume.

C9.1. The cell-free assay device of any one of embodiments C8 to C9, wherein the change between the first electrolyte volume and second electrolyte volume comprises traversal of the assay molecule, or portion thereof, which assay molecule, or portion thereof, has traversed the lipid bilayer from the first electrolyte volume into the second electrolyte volume.

C10. The device of embodiment C8 or C9, wherein the change detected between the first electrolyte volume and second electrolyte volume is a change in conductance, resistance, impedance, current, electrical potential, ion current rectification or a combination thereof.

C11. The device of any one of embodiments C1 to 010, wherein the second electrolyte volume comprises a target molecule where the target molecule is an enzymatic target of an assay molecule or a portion thereof.

C12. The device of any one of embodiments C1 to C11, wherein the binding agent is configured to bind a modified target molecule.

C13. The device of embodiment C12, wherein the second component is configured to detect a detectable signal emitted or quenched by the modified target molecule.

C14. The device of embodiment C13, wherein the second component comprises a detector configured to detect the detectable signal.

C15. The device of embodiment C14, wherein the detector comprises one or more electrodes.

C16. The device of embodiment C14 or C15, wherein the detector comprises one or more of a laser, fiber optic cable, excitation source and photodetector.

C17. The device of any one of embodiments C13 to C16, wherein the detectable signal is electromagnetic radiation.

C18. The device of embodiment C17, wherein the electromagnetic radiation is visible light.

C19. The device of any one of embodiments C13 to C18, wherein the detectable signal is a fluorescent signal.

C20. The device of any one of embodiments C13 to C19, wherein the unmodified target molecule does not emit the detectable signal.

C21. The device of any one of embodiments C13 to C19, wherein the detectable signal is emitted or quenched from at least one fluorescent label attached to, or associated with, the modified target molecule.

C22. The device of any one of embodiments C12 to C21, wherein the detector is configured to detect the modified target molecule directly.

C23. The device of any one of embodiments C12 to C22, wherein the second component is configured to detect a binding event between the modified target and the binding agent.

C24. The device of any one of embodiments C12 to C23, wherein the second component is configured to detect immobilization of the modified target.

C25. The device of any one of embodiments C12 to C24, wherein the modification of the target molecule is chosen from enzymatic cleavage, covalent addition of a molecule, binding of the assay molecule or a portion thereof, or a combination thereof.

C26. The device of embodiment C25, wherein the enzymatic cleavage comprises proteolytic cleavage.

C27. The device of any one of embodiments C1 to C26, wherein the bilayer comprises a planar lipid bilayer.

C28. The device of any one of embodiments C1 to C26, wherein the bilayer comprises an encapsulated lipid bilayer.
C28. The device of any one of embodiments C1 to C26, wherein the bilayer comprises a droplet interface bilayer.
C29. The device of any one of embodiments C1 to C28.1, wherein the bilayer further comprises additives.
C30. The device of embodiment C29, wherein the additives are chosen from cholesterol, polyethylene glycol, cell surface receptors, gangliosides, ceramides, sphingomyelin, glycosphingolipids and combinations thereof.
C31. The device of any one of embodiments C1 to C30, wherein the second component comprises a glass nanopore membrane (GNM).
C32. The device of embodiment C31, wherein the GNM comprises the proximal aperture and the channel.
C33. The device of any one of embodiments C1 to C32, wherein the second component comprises electrodes configured to contact the second electrolyte volume and the third electrolyte volume.
C33.1. The device of embodiment C33, wherein the second component electrode configured to contact the second electrolyte is the same electrode as the electrode of the first component configured to contact the second electrolyte.
C34. The device of any one of embodiments C13 to C33.1, wherein the detectable signal comprises a change between the second electrolyte volume and the third electrolyte volume chosen from a change in conductance, resistance, impedance, current, electrical potential, ion current rectification or a combination thereof.
C35. The device of any one of embodiments C13 to C34, wherein the second component is configured to detect a detectable signal in the third electrolyte volume.
C36. The device of any one of embodiments C4 to C35, wherein the toxin is a botulinum neurotoxin, or modified version or portion thereof, and the enzymatic target is a SNARE protein, or modified version or portion thereof.
C37. The device of any one of embodiments C1 to C36, comprising an apparatus configured to induce a pressure differential between the second electrolyte volume and the third electrolyte volume.
C38. The device of embodiment C37, wherein the apparatus is in effective communication with the second electrolyte volume or the third electrolyte volume, or the second electrolyte volume and the third electrolyte volume.
C39. The device of embodiment C37 or C38, wherein the apparatus comprises a chamber.
C40. The device of embodiment C39, wherein the chamber comprises the third electrolyte volume.
C41. The device of any one of embodiments C37 to C40, wherein the apparatus comprises a pressure control system.
C42. The device of embodiment C41, wherein the pressure control system comprises a pressure port.
C43. The device of embodiment C42, wherein the pressure control system comprises a syringe or piston
D1. A method for assaying a protein or toxin, comprising:
contacting a protein or toxin with a cell-free assay device of any one of embodiments A1 to A62 or C1 to C43, wherein the protein or toxin is in the first electrolyte volume;
detecting the presence, absence or amount of an interaction between the lipid bilayer and the protein or toxin; and
detecting the presence, absence or amount of an interaction between the protein or toxin, or portion thereof, with an enzymatic target of the protein or toxin or portion of the protein or toxin, which enzymatic target is, at least in part, in the second electrolyte volume.
D2. The method of embodiment D1, wherein detecting the presence, absence or amount of an interaction between the lipid bilayer and the protein or toxin comprises detecting the presence, absence or amount of insertion of the protein or toxin into the lipid bilayer.
D3. The method of embodiment D1 or D2, wherein detecting the presence, absence or amount of an interaction between the lipid bilayer and the protein or toxin comprises monitoring the conductance of the lipid bilayer.
D4. The method of any one of embodiments D1 to D3, wherein detecting the presence, absence or amount of an interaction between the protein or toxin, or portion thereof, with an enzymatic target of the protein or toxin or portion of the protein or toxin comprises detecting the presence, absence or amount of a cleavage product of the enzymatic target bound by the binding agent.
D5. The method of embodiment D4, wherein the presence, absence or amount of the cleavage product is detected by monitoring conductance of the channel in the substrate.
D6. The method of embodiment D4, wherein the presence, absence or amount of the cleavage product is detected by monitoring a detectable label in association with the cleavage product.
D7. The method of any one of embodiments D1 to D6, which comprises determining the potency of a toxin.
D8. The method of embodiment D7, wherein determining the potency of the toxin comprises assaying two or three of (i) lipid bilayer insertion by the toxin, (ii) traversal of the lipid bilayer by the toxin or portion of the toxin, and (iii) generation of a cleavage product of an enzymatic target by the toxin or a portion of the toxin that has traversed the lipid bilayer.
D9. The method of any one of embodiments D1 to D8, which comprises determining the effectiveness of a neutralizing therapeutic agent.
D10. The method of embodiment D9, wherein determining the effectiveness of the neutralizing therapeutic agent comprises assaying two or three of (i) lipid bilayer insertion by the toxin, (ii) traversal of the lipid bilayer by the toxin or portion of the toxin, and (iii) generation of a cleavage product of an enzymatic target by the toxin or a portion of the toxin that has traversed the lipid bilayer.
E1. A cell-free assay device, comprising:
a first electrolyte volume, a second electrolyte volume and a third electrolyte volume;
a first set of one or more components comprising a lipid bilayer configured to separate the first electrolyte volume and the second electrolyte volume;
a second set of one or more components configured to separate the second electrolyte volume and the third electrolyte volume;
a first component configured to detect a change in the lipid bilayer; and
a second component configured to detect a change between the second and the third electrolyte volumes.
F1. A method for altering an interaction between an analyte and a binding agent, comprising:
interacting an analyte with a binding agent in association with a substrate in a system, wherein the substrate comprises a channel;
inducing a pressure differential across the channel; and
assessing an interaction between the analyte and the binding agent, whereby inducing a pressure differential alters the interaction relative to the interaction assessed without inducing a pressure differential.

F2. A method for enhancing an interaction between an analyte and a binding agent, comprising:
interacting an analyte with a binding agent attached to a substrate in a system, wherein the substrate comprises a channel; and
assessing an interaction between the analyte and the binding agent, wherein a pressure differential across the channel is at a level at which the interaction is enhanced relative to the interaction at a lower pressure differential.

F3. The method of embodiment F1 or F2, wherein the binding agent is attached to the channel.

F4. The method of any one of embodiments F1 to F3, wherein the attachment to the substrate comprises a covalent attachment.

F5. The method of any one of embodiments F1 to F3, wherein the attachment to the substrate comprises a non-covalent attachment.

F6. The method of any one of embodiments F1 to F5, wherein the attachment to the substrate comprises attachment to a linker.

F7. The method of any one of embodiments F1 to F6, where the attachment to the substrate comprises a binding molecule that specifically binds the binding agent.

F8. The method of any one of embodiments F1 to F7, wherein the system comprises a first volume and a second volume, and the channel separates the first volume and the second volume.

F9. The method of embodiment F8, wherein the pressure differential comprises a difference in pressure between the first volume and the second volume.

F10. The method of any one of embodiments F1 to F9, wherein the assessing the interaction comprises a current rectification measurement, an impedance based measurement, a coulter-counter technique or combination thereof.

F11. The method of any one of embodiments F1 to F10, wherein the assessing of the interaction between the analyte and the binding agents is a current rectification measurement.

F12. The method of any one of embodiments F1 to F11, wherein inducing a pressure differential across the channel comprises applying a positive pressure across the channel.

F13. The method of any one of embodiments F1 to F12, wherein inducing a pressure differential across the channel comprises applying a negative pressure across the channel.

F14. The method of any one of embodiments F1 to F13, wherein altering the interaction between the analyte and binding agents reduces a limit of detection of the analyte.

F15. The method of embodiment F14, wherein the limit of detection of the analyte is reduced by a factor of at least 1.1.

F16. The method of embodiment F14, wherein the limit of detection of the analyte is reduced by a factor of at least 10.

F17. The method of embodiment F14, wherein the limit of detection of the analyte is reduced by a factor of at least 100.

F18. The method of embodiment F14, wherein the limit of detection of the analyte is reduced by a factor of at least 1,000.

F19. The method of embodiment F14, wherein the limit of detection of the analyte is reduced by a factor of at least 10,000.

F20. The method of embodiment F14, wherein the limit of detection of the analyte is reduced by a factor of at least 100,000.

F21. The method of embodiment F14, wherein the limit of detection of the analyte is reduced by a factor of at least 1,000,000.

F22. The method of any one of embodiments F1 to F21, wherein altering the interaction between the analyte and binding agents reduces a measurement time.

F23. The method of embodiment F22, wherein the measurement time is reduced by a factor of at least 1.1.

F24. The method of embodiment F22, wherein the measurement time is reduced by a factor of at least 10.

F25. The method of embodiment F22, wherein the measurement time is reduced by a factor of at least 100.

F26. The method of embodiment F22, wherein the measurement time is reduced by a factor of at least 1,000.

F27. The method of embodiment F22, wherein the measurement time is reduced by a factor of at least 10,000.

F28. The method of embodiment F22, wherein the measurement time is reduced by a factor of at least 100,000.

F29. The method of embodiment F22, wherein the measurement time is reduced by a factor of at least 1,000,000.

F30. The method of any one of embodiments F1 to F29, wherein altering the interaction between the analyte and binding agents enables detection of a lower concentration of analyte in the same measurement time as a higher concentration of analyte.

F31. The method of embodiment F30, wherein the lower concentration of analyte is lower by at least a factor 1.1 than the higher concentration of analyte.

F32. The method of embodiment F30, wherein the lower concentration of analyte is lower by at least a factor of 10 than the higher concentration of analyte.

F33. The method of embodiment F30, wherein the lower concentration of analyte is lower by at least a factor of 100 than the higher concentration of analyte.

F34. The method of embodiment F30, wherein the lower concentration of analyte is lower by at least a factor of 1,000 than the higher concentration of analyte.

F35. The method of embodiment F30, wherein the lower concentration of analyte is lower by at least a factor of 10,000 than the higher concentration of analyte.

F36. The method of embodiment F30, wherein the lower concentration of analyte is lower by at least a factor of 100,000 than the higher concentration of analyte.

F37. The method of embodiment F30, wherein the lower concentration of analyte is lower by at least a factor of 1,000,000 than the higher concentration of analyte.

F38. The method of any one of embodiments F1 to F37, wherein the substrate comprises glass.

F39. The method of any one of embodiments F1 to F38, wherein the substrate comprises quartz.

F40. The method of any one of embodiments F1 to F39, wherein the substrate comprises metal.

F41. The method of any one of embodiments F1 to F40, wherein the substrate comprises gold.

F42 The method of any one of embodiments F1 to F41, wherein the substrate comprises plastic.

F43. The method of any one of embodiments F1 to F42, wherein the substrate and the channel comprises a coating.

F44. The method of embodiment F43, wherein the coating comprises gold, silicon nitride, grapheme and combinations thereof.

F45. The method of any one of embodiments F1 to F44, wherein the analyte is chosen from an antibody, antibody fragment, reduced antibody, chemically modified antibody, antibody receptor, hapten, anti-hapten, protein, cleaved protein, polypeptide, peptide, peptide analog, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound, or combinations thereof.

F46. The method of any one of embodiments F1 to F45, wherein the analyte is an antibody.

F47. The method of any one of embodiments F1 to F45, wherein the analyte is an antigen.

F48. The method of any one of embodiments F1 to F45, wherein the analyte is a protein.

F49. The method of any one of embodiments F1 to F45, wherein the analyte is a cleaved protein.

F50. The method of any one of embodiments F1 to F49, wherein the binding agent is chosen from an antibody, antibody fragment, reduced antibody, chemically modified antibody, antibody receptor, hapten, anti-hapten, protein, cleaved protein, polypeptide, peptide, peptide analog, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound or combinations thereof.

F51. The method of any one of embodiments F1 to F50, wherein the binding agent is an antibody.

F52. The method of any one of embodiments F1 to F50, wherein the binding agent is an antigen.

F53. The method of any one of embodiments F1 to F50, wherein the binding agent is a protein.

F54. The method of any one of embodiments F1 to F50, wherein the binding agent is a cleaved protein.

G1. A device, comprising:
a substrate comprising a channel and a binding agent in association with the substrate;
a component configured to detect an interaction between an analyte and the binding agent; and
a component configured to apply or maintain a pressure differential across the channel in the device.

G2. The device of embodiment G1, wherein the binding agent is attached to the channel.

G3. The device of embodiment G1 or G2, wherein the attachment to the substrate comprises a covalent attachment.

G3.1. The device of embodiment G1 or G2, wherein the attachment to the substrate comprises a non-covalent attachment.

G4. The device of any one of embodiments G1 to G3.1, wherein the attachment to the substrate comprises attachment to a linker.

G5. The device of any one of embodiments G1 to G4, where the attachment to the substrate comprises a binding molecule that specifically binds the binding agent.

G6. The device of any one of embodiments G1 to G5, wherein the device comprises a first volume and a second volume, and the channel separates the first volume and the second volume.

G7. The device of embodiment G6, wherein the pressure differential comprises a difference in pressure between the first volume and the second volume.

G8. The device of any one of embodiments G1 to G7, wherein the component configured to detect an interaction is configured to detect a change in current, impedance, resistance, ion current rectification or electrical potential difference.

G9. The device of any one of embodiments G1 to G8, wherein the component configured to detect an interaction is configured for a current rectification measurement, an impedance based measurement, a coulter-counter technique or combination thereof.

G10. The device of any one of embodiments G1 to G9, wherein the component configured to detect an interaction between the analyte and the binding agents is configured for a current rectification measurement.

G11. The device of any one of embodiments G1 to G10, wherein the component configured to apply or maintain a pressure differential is configured to apply a positive pressure across the channel.

G12. The device of any one of embodiments G1 to G11, wherein the component configured to apply or maintain a pressure differential is configured to apply a negative pressure across the channel.

G13. The device of any one of embodiments G1 to G12, wherein the substrate comprises glass.

G14. The device of any one of embodiments G1 to G13, wherein the substrate comprises quartz.

G15. The device of any one of embodiments G1 to G14, wherein the substrate comprises metal.

G16. The device of any one of embodiments G1 to G15, wherein the substrate comprises gold.

G17. The device of any one of embodiments G1 to G16, wherein the substrate and the channel comprises a coating.

G18. The device of embodiment G17, wherein the coating comprises gold.

G19. The device of any one of embodiments G1 to G18, wherein the analyte is chosen from an antibody, antibody fragment, reduced antibody, chemically modified antibody, antibody receptor, hapten, anti-hapten, protein, cleaved protein, polypeptide, peptide, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound, or combinations thereof.

G20. The device of any one of embodiments G1 to G19, wherein the analyte is an antibody.

G21. The device of any one of embodiments G1 to G19, wherein the analyte is an antigen.

G22. The device of any one of embodiments G1 to G19, wherein the analyte is a protein.

G23. The device of any one of embodiments G1 to G19, wherein the analyte is a cleaved protein.

G24. The device of any one of embodiments G1 to G23, wherein the binding agent is chosen from an antibody, antibody fragment, reduced antibody, chemically modified antibody, antibody receptor, hapten, anti-hapten, protein, cleaved protein, polypeptide, peptide, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound or combinations thereof.

G25. The device of any one of embodiments G1 to G24, wherein the binding agent is an antibody.

G26. The device of any one of embodiments G1 to G24, wherein the binding agent is an antigen.

G27. The device of any one of embodiments G1 to G24, wherein the binding agent is a protein.

G28. The device of any one of embodiments G1 to G27, wherein the binding agent is a cleaved protein.

DRAWING ELEMENTS

Provided hereafter is a listing of some elements shown in the drawings.

| Item Name and/or Description | Call Out/ Reference Number |
|---|---|
| First Electrolyte Volume | 10 |
| Second Electrolyte Volume | 12 |
| Third Electrolyte Volume | 13 |
| Channel | 14 |
| Housing | 16 |
| Housing interior substrate | 17 |
| First Electrode | 20 |
| Second Electrode | 22 |
| Third Electrode | 23 |
| Internal Probe | 25 |
| Lipid Bilayer | 30 |
| Encapsulated Lipid Bilayer | 30' |
| First Substrate | 34 |
| Second Substrate | 35 |
| Linker | 36 |
| Substrate Support | 37 |
| Aperture | 40 |
| Analyte | 41 |
| Substrate of Channel | 42 |
| Second Chamber | 43 |
| GNM Substrate | 50 |
| Light or Laser Source | 52 |
| Detector | 54 |
| Electromagnetic Radiation | 60 |
| Binding Agent | 70 |
| Interface of first lipid droplet and second lipid droplet | 71 |
| First lipid droplet | 72 |
| Second lipid droplet | 73 |
| Assay Molecule (e.g., a toxin) | 75 |
| Modified Assay Molecule - Pore forming portion | 80 |
| Modified Assay Molecule - Enzyme Portion | 82 |
| Target Molecule | 85 |
| Oil or Lipid | 94 |
| Modified Target Molecule | 100 |
| Nanodisk Electrode | 103 |
| Cyano-silane | 105 |
| Pt | 106 |
| Aperture | 109 |
| Linker | 110 |
| Antibody | 111 |

What is claimed is:

1. A method for assessing an interaction between an analyte and a binding agent in a system, comprising:
    interacting an analyte with a binding agent attached to a glass nanopore membrane of the system, wherein the system comprises a first volume and a second volume, the first volume and/or the second volume are sealed and the glass nanopore membrane comprises a channel separating the first volume and the second volume;
    maintaining a pressure differential between the first volume and the second volume for a measurement time; and
    assessing an interaction between the analyte and the binding agent, wherein the pressure differential between the first volume and the second volume reduces a limit of detection of the analyte for the measurement time relative to the limit of detection of the analyte for the measurement time in the absence of the pressure differential.

2. The method of claim 1, wherein the binding agent is attached to the channel.

3. The method of claim 1, wherein the attachment to the glass nanopore membrane comprises a covalent attachment.

4. The method of claim 1, wherein the attachment to the glass nanopore membrane comprises a non-covalent attachment.

5. The method of claim 1, wherein the attachment to the glass nanopore membrane comprises attachment to a linker.

6. The method of claim 1, where the attachment to the glass nanopore membrane comprises a binding molecule that specifically binds the binding agent.

7. The method of claim 1, wherein the assessing the interaction comprises a current rectification measurement, an impedance based measurement, a coulter-counter technique or combination thereof.

8. The method of claim 7, wherein the assessing the interaction comprises a current rectification measurement.

9. The method of claim 1, wherein maintaining a pressure differential comprises applying a positive pressure to the first and/or second volume.

10. The method of claim 1, wherein the pressure differential across the channel comprises applying a negative pressure across the channel.

11. The method of claim 1, wherein the limit of detection of the analyte is reduced by a factor of at least 100.

12. The method of claim 1, wherein altering the interaction between the analyte and binding agents reduces a measurement time.

13. The method of claim 1, wherein altering the interaction between the analyte and binding agents enables detection of a lower concentration of analyte in the same measurement time as a higher concentration of analyte.

14. The method of claim 1, wherein the glass nanopore membrane comprises a coating.

15. The method of claim 14, wherein the coating comprises gold, silicon nitride, grapheme and combinations thereof.

16. The method of claim 1, wherein the analyte is chosen from an antibody, antibody fragment, reduced antibody, chemically modified antibody, antibody receptor, hapten, anti-hapten, protein, cleaved protein, polypeptide, peptide, peptide analog, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound, or combinations thereof.

17. The method of claim 16, wherein the analyte comrpises an antigen.

18. The method of claim 1, wherein the binding agent is chosen from an antibody, antibody fragment, reduced antibody, chemically modified antibody, antibody receptor, hapten, anti-hapten, protein, cleaved protein, polypeptide, peptide, peptide analog, nucleic acid, a nucleotide, a nucleotide analog or derivative, an alkyl moiety, an alkanoyl moiety, an alkanoic acid or alkanoate moiety, a glyceryl moiety, a phosphoryl moiety, a glycosyl moiety, an ubiquitin moiety, lectin, aptamer, receptor, ligand, metal ion, a pathogen, bacterium, anthrax, virus, biomarker, chemical contaminant, organic contaminant, drug, toxin, ricin, chemical compound or combinations thereof.

19. The method of claim 18, wherein the binding agent comprises an antibody.

20. The method of claim 1, wherein the pressure differential is an optimal pressure differential at which the limit of detection of the analyte is the minimum for the measurement time.

21. The method of claim 1, wherein the pressure differential is an optimal pressure differential at which the lowest concentration of analyte is detected for the measurement time.

22. The method of claim 1, wherein the limit of detection of the analyte is reduced by a factor of at least 1,000.

23. The method of claim 1, wherein the limit of detection of the analyte is reduced by a factor of at least 10,000.

24. The method of claim 1, wherein the limit of detection of the analyte is reduced by a factor of at least 100,000.

25. The method of claim 1, wherein the limit of detection of the analyte is reduced by a factor of at least 1,000,000.

* * * * *